(12) United States Patent
Salmon et al.

(10) Patent No.: US 12,214,124 B2
(45) Date of Patent: Feb. 4, 2025

(54) SUPPORT FOR A BREATHING ASSISTANCE APPARATUS AND/OR ACCESSORIES

(71) Applicant: Fisher & Paykel Healthcare Limited, Auckland (NZ)

(72) Inventors: Andrew Paul Maxwell Salmon, Auckland (NZ); Kevin Peter O'Donnell, Auckland (NZ); Andre Van Schalkwyk, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 997 days.

(21) Appl. No.: 17/272,167

(22) PCT Filed: Aug. 28, 2019

(86) PCT No.: PCT/IB2019/057226
§ 371 (c)(1),
(2) Date: Feb. 26, 2021

(87) PCT Pub. No.: WO2020/049411
PCT Pub. Date: Mar. 12, 2020

(65) Prior Publication Data
US 2021/0205553 A1  Jul. 8, 2021

Related U.S. Application Data

(60) Provisional application No. 62/855,243, filed on May 31, 2019, provisional application No. 62/726,717, filed on Sep. 4, 2018.

(51) Int. Cl.
*A61M 16/06* (2006.01)
*A61M 16/00* (2006.01)
(Continued)

(52) U.S. Cl.
CPC ........ *A61M 16/0003* (2014.02); *A61M 16/06* (2013.01); *A61M 16/0875* (2013.01);
(Continued)

(58) Field of Classification Search
CPC .............. A61M 16/0003; A61M 16/06; A61M 16/0666; A61M 16/0683; A61M 16/0875;
(Continued)

(56) References Cited

U.S. PATENT DOCUMENTS 2,508,909 A * 5/1950 Evans ................ B65D 5/46024
229/120.04
3,820,657 A * 6/1974 Klygis et al. ........ B65D 71/004
206/174
(Continued)

FOREIGN PATENT DOCUMENTS

CN    20289768 U    4/2013
CN    205172411 U   4/2016
(Continued)

OTHER PUBLICATIONS

International Search Report and Written Opinion received in Application No. PCT/IB2019/057226, dated Dec. 20, 2019.
(Continued)

*Primary Examiner* — Nkeisha Smith
(74) *Attorney, Agent, or Firm* — VIA LLP

(57) ABSTRACT

A support apparatus for a breathing assistance apparatus has a base, a mount, and a handle. The mount is configured to releasably couple the support apparatus with the breathing assistance apparatus by lowering the breathing assistance apparatus relative to the mount. The handle is configured to enable the support apparatus and a releasably coupled breathing assistance apparatus to be lifted and carried by a user.

17 Claims, 41 Drawing Sheets

(51) Int. Cl.
*A61M 16/08* (2006.01)
*A61M 16/16* (2006.01)

(52) U.S. Cl.
CPC ..... *A61M 16/162* (2013.01); *A61M 2209/082* (2013.01); *A61M 2209/084* (2013.01)

(58) Field of Classification Search
CPC .............. A61M 16/1621; A61M 16/16; A61M 2209/082; A61M 2209/084; A61M 2209/08; A61M 2209/086; A61B 50/20; A61B 50/24; F16B 2200/30
See application file for complete search history.

(56) References Cited

U.S. PATENT DOCUMENTS

| | | | |
|---|---|---|---|
| 3,915,164 A | 10/1975 | Bird | |
| 4,470,503 A * | 9/1984 | Stone | B65D 71/125 206/199 |
| 4,515,283 A | 5/1985 | Suzuki | |
| 4,926,856 A | 5/1990 | Cambio, Jr. et al. | |
| 4,955,877 A | 9/1990 | Kurtz et al. | |
| 5,400,901 A * | 3/1995 | Harrelson | B65D 71/0048 206/196 |
| 5,759,149 A * | 6/1998 | Goldberg | F24F 11/523 600/22 |
| 5,967,319 A * | 10/1999 | White, Jr. | B65D 71/0011 206/428 |
| 6,427,984 B1 | 8/2002 | Mulvaney et al. | |
| 6,581,823 B1 * | 6/2003 | De Beck | B65D 5/6664 229/117.14 |
| 6,629,927 B1 | 10/2003 | Mesaros et al. | |
| 6,750,556 B2 | 6/2004 | Sodemann et al. | |
| 7,677,246 B2 | 3/2010 | Kepler et al. | |
| 7,942,380 B2 * | 5/2011 | Bertinetti | A61M 16/0057 248/682 |
| 8,316,848 B2 | 11/2012 | Kwok et al. | |
| 8,356,593 B2 | 1/2013 | Cortez, Jr. et al. | |
| 8,540,196 B1 | 9/2013 | Hodson | |
| 8,814,107 B2 | 8/2014 | Hampe et al. | |
| 9,072,543 B2 | 7/2015 | Miller et al. | |
| 9,182,062 B2 | 11/2015 | Kwok et al. | |
| 9,474,848 B2 | 10/2016 | Williams et al. | |
| 9,872,703 B2 | 1/2018 | Miller et al. | |
| 10,058,666 B2 | 8/2018 | Kwok et al. | |
| 10,342,936 B2 | 7/2019 | Von Hollen | |
| 10,507,294 B2 | 12/2019 | Mahadevan et al. | |
| 10,773,035 B2 * | 9/2020 | Klinger | A61F 5/56 |
| 11,116,922 B2 * | 9/2021 | Salmon | A61M 16/0666 |
| 11,806,477 B1 * | 11/2023 | Adams | A61G 7/05 |
| 2002/0043595 A1 | 4/2002 | Bridgers | |
| 2005/0275178 A1 | 12/2005 | Huesdash et al. | |
| 2006/0144396 A1 | 7/2006 | DeVries et al. | |
| 2007/0045152 A1 | 3/2007 | Kwok et al. | |
| 2009/0039210 A1 | 2/2009 | Yates et al. | |
| 2010/0052293 A1 | 3/2010 | Brooks et al. | |
| 2010/0218764 A1 | 9/2010 | Kwok et al. | |
| 2010/0236552 A1 * | 9/2010 | Kwok | F16L 31/00 128/204.21 |
| 2011/0203587 A1 * | 8/2011 | Bertinetti | A61M 16/021 280/47.35 |
| 2014/0083524 A1 | 3/2014 | Huang | |
| 2016/0317392 A1 * | 11/2016 | Harris | F16M 11/046 |
| 2017/0197050 A1 * | 7/2017 | Reinburg | F16M 11/06 |
| 2017/0203072 A1 * | 7/2017 | Tonning | A61G 12/002 |
| 2018/0132894 A1 | 5/2018 | Miller et al. | |
| 2018/0147374 A1 | 5/2018 | Salmon | |
| 2018/0272086 A1 * | 9/2018 | Klinger | A61M 5/1415 |
| 2019/0001089 A1 | 1/2019 | Hoysan | |
| 2019/0134331 A1 * | 5/2019 | Meyer | A61M 16/208 |
| 2020/0316332 A1 | 10/2020 | Bath et al. | |
| 2022/0090741 A1 * | 3/2022 | Schaub | A61M 16/101 |

FOREIGN PATENT DOCUMENTS

| | | |
|---|---|---|
| DE | 10323754 | 12/2004 |
| DE | 102007026565 | 12/2007 |
| FR | 2901998 | 12/2007 |
| JP | 2016-135200 A | 7/2016 |
| WO | WO 2002/092157 A1 | 11/2002 |
| WO | WO 2004/084981 | 10/2004 |
| WO | WO 2004/112529 A1 | 12/2004 |
| WO | WO 2007/019624 | 2/2007 |
| WO | WO 2007/045905 A1 | 4/2007 |
| WO | WO 2010/039051 A2 | 4/2010 |
| WO | WO 2015/068687 A1 | 5/2015 |

OTHER PUBLICATIONS

"New Power Cord for Respironics REMstar Plus, Pro, and Auto Machines," Amazon.com (Year: 2020).
"RespLabs CPAP Hose, Black-Out Tubing," Amazon.com (Year: 2020).
Chinese Patent Office, First Office Action, Application No. 201721633735.3, dated Apr. 4, 2019, in 5 pages.
Fisher & Paykel Healthcare Limited, myAIRVO Compact Stand (900PT400) User Instructions (revision B), 2010, in 2 pages.

* cited by examiner

SUPPORT FOR A BREATHING ASSISTANCE APPARATUS AND/OR ACCESSORIES

TECHNICAL FIELD

The present invention relates to a support apparatus for a breathing assistance apparatus and/or for one or more accessories of such an apparatus.

BACKGROUND ART

Breathing assistance apparatuses are used in various environments such as hospital, medical facility, residential care, or home environments to deliver a flow of gas to users or patients.

The breathing assistance apparatuses typically have one or more accessories such as a breathing conduit and a patient interface such as a cannula for delivering gases to a patient. The conduit is often a significant length to enable gases to be delivered from the housing of the breathing assistance apparatus to the patient who can be positioned a reasonable distance away from the apparatus. For example, the apparatus may be placed on a floor or other support surface, and the patient may be in a bed. Depending on the configuration of the breathing assistance apparatus, the apparatus may have additional accessories such as a flexible liquid bag that delivers liquid to a humidifier liquid chamber via one or more tubes.

For home use, a breathing assistance apparatus may typically be kept on the floor because the apparatus may be large and noisy. Additionally, the apparatus is likely to be kept on the floor when the apparatus is not being used, so it can be positioned out of the way. The floor environment can be dusty, increasing the likelihood of dust and particulate ingress into the breathing assistance apparatus and potentially into the gas flow. Because the apparatus may have gases inlet(s) near the bottom of the apparatus, there may be a perception that the apparatus should not be positioned on the floor. Generally, breathing assistance apparatuses do not provide adequate storage for the patient interface such as a cannula when it is not being used, meaning that the used patient interface such as a cannula needs to be placed on a support surface such as a bedside table when it is not being used. Additionally, the conduit can present a tripping hazard. Similar issues may be encountered in a transport situation; e.g. helicopter or ambulance use.

Support apparatuses for breathing assistance apparatuses may only be designed for use with a single breathing assistance apparatus. That means that a user would need to buy multiple support apparatuses for use with different breathing assistance apparatuses or when they change their breathing assistance apparatus.

While a support apparatus may act as a stand to support the breathing assistance apparatus, it may not be suitable for a user to easily carry the breathing assistance apparatus via the support apparatus.

While a support apparatus may provide support for one or more accessories of a breathing assistance apparatus, difficulties can be encountered when a long accessory such as a conduit or power cord is to be supported.

Breathing assistance apparatuses may be susceptible to contamination, particularly if they are stored for an extended period of time when not in use.

SUMMARY

Accordingly, it would be desirable to provide a support apparatus for a breathing assistance apparatus that can be used to support more than one breathing assistance apparatus.

Alternatively, it would be desirable to provide a shroud for a support apparatus for a breathing assistance apparatus that can cover a substantial part of a support apparatus and breathing assistance apparatus, to reduce contamination of the breathing assistance apparatus.

Alternatively, it would be desirable to provide a support apparatus for a breathing assistance apparatus and/or accessory that can be made compact for storage or transport.

Alternatively, it would be desirable to provide a support apparatus for a breathing assistance apparatus and/or accessory that can provide enhanced support of a long accessory.

Thus, in accordance with certain features, aspects and advantages of at least one of the embodiments disclosed herein, a support apparatus for a breathing assistance apparatus is disclosed, the support apparatus comprising:
  a base;
  an upstanding component;
  a first mount that is configured to releasably couple the support apparatus with a mounting feature of a first breathing assistance apparatus; and
  a second mount that has a different configuration from the first mount and that is configured to releasably couple the support apparatus with a mounting feature of a second breathing assistance apparatus, wherein the second breathing assistance apparatus has a different configuration from the first breathing assistance apparatus.

In some configurations, the first mount and the second mount are configured so that only one of the first breathing assistance apparatus and the second breathing assistance apparatus can be releasably coupled to the support apparatus at a time.

In some configurations, the first mount is configured to releasably couple with the first breathing assistance apparatus by moving the first breathing assistance apparatus in a generally vertical direction relative to the first mount.

In some configurations, the first mount comprises a recess that is configured to engage with a tongue on the first breathing assistance apparatus.

In some configurations, the first mount is on the upstanding component.

In some configurations, the first mount is configured to support the first breathing assistance apparatus such that an underside of the first breathing assistance apparatus is positioned with a spacing above the base.

In some configurations, the support apparatus comprises a support member spaced from the first mount to assist with supporting the first breathing assistance apparatus when the first breathing assistance apparatus is releasably coupled to the support apparatus.

In some configurations, the upstanding component comprises the support member.

In some configurations, the support member is provided elsewhere on the support apparatus.

In some configurations, the second mount is on the base.

In some configurations, the second mount comprises one or more upstanding projections, wherein the projection(s) is/are configured to engage with complementary recess(es) in an underside of the second breathing assistance apparatuses.

In some configurations, the first mount and the support member are configured to be in close proximity to, or contact with, the second breathing assistance apparatus when the second breathing assistance apparatus is releasably coupled with the second mount.

In some configurations, the first mount and a portion of the upstanding component are configured to be in close proximity to, or contact with, the second breathing assistance apparatus when the second breathing assistance apparatus is releasably coupled with the second mount.

In some configurations, the upstanding component is removably coupled to the base. In some alternative configurations, the upstanding component may be integrally formed with the base.

Additionally, in accordance with certain features, aspects and advantages of at least one of the embodiments disclosed herein, the combination of the support apparatus and a first breathing assistance apparatus releasably coupled to the first mount is disclosed.

In some configurations, the first breathing assistance apparatus cannot couple to the second mount.

Additionally, in accordance with certain features, aspects and advantages of at least one of the embodiments disclosed herein, the combination of the support apparatus and a second breathing assistance apparatus releasably coupled to the second mount is disclosed.

In some configurations, the second breathing assistance apparatus cannot couple to the first mount.

Additionally, in accordance with certain features, aspects and advantages of at least one of the embodiments disclosed herein, the combination of the support apparatus, a first or second breathing assistance apparatus, and a liquid container for holding liquid and supplying liquid to a humidifier liquid chamber of the breathing assistance apparatus is disclosed.

Additionally, in accordance with certain features, aspects and advantages of at least one of the embodiments disclosed herein, a support apparatus for a breathing assistance apparatus is disclosed, the support apparatus comprising:
a base;
a mount that is configured to releasably couple the support apparatus with a breathing assistance apparatus by lowering the breathing assistance apparatus relative to the mount; and
a handle that is configured to enable the support apparatus and a releasably coupled breathing assistance apparatus to be lifted and carried by a user.

In some configurations, the handle is located higher than the mount.

In some configurations, the handle has a centre, and the centre of the handle is substantially aligned with a centre of mass of the support apparatus.

In some configurations, the handle is located higher than the centre of mass of the support apparatus.

In some configurations, the mount is configured so that a centre of mass of a releasably coupled breathing assistance apparatus is substantially aligned or coincident with the centre of mass of the support apparatus.

In some configurations, the support apparatus is configured to support the releasably coupled breathing assistance apparatus substantially evenly about the centre of mass of the breathing assistance apparatus.

In some configurations, the support apparatus comprises a support member spaced from the mount to assist with supporting the first breathing assistance apparatus.

In some configurations, the mount is configured to support a first side of the breathing assistance apparatus, and the support member is configured to support a second, opposite side of the breathing assistance apparatus.

In some configurations, the mount, and optionally the support member, is/are configured to support the breathing assistance apparatus such that an underside of the breathing assistance apparatus is positioned with a spacing above the base.

In some configurations, the support apparatus comprises a first upstanding member at or adjacent a first side of the support apparatus, and a second upstanding member at or adjacent a second side of the support apparatus, wherein the breathing assistance apparatus is configured to be positioned between the first upstanding member and the second upstanding member when the breathing assistance apparatus is removably coupled to the mount.

In some configurations, an upper transverse connecting member extends between and connects upper ends of the first upstanding member and the second upstanding member.

In some configurations, the upper transverse connecting member forms the handle.

Additionally, in accordance with certain features, aspects and advantages of at least one of the embodiments disclosed herein, the combination of the support apparatus, a breathing assistance apparatus, and a liquid container for holding liquid and supplying liquid to a humidifier liquid chamber of the breathing assistance apparatus is disclosed.

Additionally, in accordance with certain features, aspects and advantages of at least one of the embodiments disclosed herein, a support apparatus for a breathing apparatus is disclosed, the support apparatus comprising:
an arm having a first end and a second end;
a mount at or adjacent the first end of the arm and that is configured to releasably couple the support apparatus with a breathing assistance apparatus;
and a support member at or adjacent the second end of the arm and that is configured to assist with supporting the breathing assistance apparatus.

In some configurations, the arm comprises a first upstanding member corresponding to the first end of the arm and a second upstanding member corresponding to the second end of the arm.

In some configurations, an upper transverse connecting member extends between and connects upper ends of the first upstanding member and the second upstanding member.

In some configurations, the upper transverse connecting member forms a handle configured to enable the support apparatus and a releasably coupled breathing assistance apparatus to be lifted and carried by a user.

In some configurations, the arm comprises at least one mechanical feature for holding an accessory of a breathing assistance apparatus, and the at least one mechanical feature has a shape that is complementary to the shape of the accessory.

In some configurations, the support apparatus comprises a plurality of the mechanical features, and the mechanical features are configured to hold a conduit and a patient interface.

In some configurations, the support apparatus further comprises an accessory support extension that is configured to couple to at least one of the mechanical features.

In some configurations, a lower end of the accessory support extension is configured to couple to said at least one of the mechanical features and an upper end of the accessory support extension is configured to support the accessory.

In some configurations, the support apparatus further comprises a base, wherein the arm is supported by the base.

In some configurations, the arm is removably coupled to the base.

In some configurations, the arm extends upwardly from a periphery of the base.

Additionally, in accordance with certain features, aspects and advantages of at least one of the embodiments disclosed herein, the combination of the support apparatus, a breathing assistance apparatus, and a liquid container for holding liquid and supplying liquid to a humidifier liquid chamber of the breathing assistance apparatus is disclosed.

Additionally, in accordance with certain features, aspects and advantages of at least one of the embodiments disclosed herein, a support apparatus for a breathing apparatus is disclosed, the support apparatus comprising:
- a mount that is configured to releasably couple the support apparatus with a breathing assistance apparatus;
- a first component comprising a first connector; and
- a second component comprising a second connector;
- wherein the first connector is removably engageable with the second connector by moving the first component and second component towards each other in a first direction, and wherein one of the connectors comprises a release member that is movable in a second direction that is transverse to the first direction, wherein the first connector and the second connector are configured such that the first connector cannot be disengaged from the second connector by pulling the first component away from the second component, without also moving the release member in the second direction.

In some configurations, said one of the connectors comprises a resilient finger, and the release member comprises a protrusion that extends from the finger.

In some configurations, the protrusion extends from the finger at or adjacent a free end of the finger.

In some configurations, the protrusion is configured to engage against an edge of the other one of the connectors, to prevent disengagement of the first connector from the second connector.

In some configurations, said other one of the connectors comprises an aperture that is complementary to the shape of the release member, wherein the protrusion is received in the aperture when the first connector and the second connector are engaged.

In some configurations, the edge and the release member are configured such that the release member can clear the edge by moving the release member in the second direction into an interior of said other one of the connectors.

In some configurations, the second direction is toward a centre of the support apparatus or is away from a centre of the support apparatus.

In some configurations, said one of the connectors comprises a locating feature to provide axial alignment of the first component and the second component.

In some configurations, the locating feature comprises an enlarged region at a base of the respective connector.

In some configurations, the locating feature comprises a tab that is configured to be received in a complementary recess in said other one of the connectors.

In some configurations, the first component comprises a base of the support apparatus and the second component comprises an upstanding component of the support apparatus.

In some configurations, the first component comprises an upstanding member of the support apparatus and the second component comprises another upstanding component of the support apparatus.

In some configurations, the mount is part of the first component or second component.

Additionally, in accordance with certain features, aspects and advantages of at least one of the embodiments disclosed herein, the combination of the support apparatus, a breathing assistance apparatus, and a liquid container for holding liquid and supplying liquid to a humidifier liquid chamber of the breathing assistance apparatus is disclosed.

Additionally, in accordance with certain features, aspects and advantages of at least one of the embodiments disclosed herein, a support apparatus for a breathing apparatus is disclosed, the support apparatus comprising:
- a base;
- an arm having a first end removably coupled to the base at a first location on the base, a second end removably coupled to the base at a second location on the base, the arm extending upwardly from the first and the second end so that the base and the arm form a general loop shape, and at least one coupling arrangement in the arm between the first end and the second end, the coupling arrangement configured to enable the arm to be disassembled.

In some configurations, the arm comprises two said coupling arrangements so that the arm can be disassembled into three parts.

In some configurations, the arm comprises a first upstanding member comprising the first end, a second upstanding member comprising the second end, and an upper transverse connecting member, a first coupling arrangement that removably couples the first upstanding member to the upper transverse connecting member, and a second coupling arrangement that removably couples the second upstanding member to the upper transverse connecting member.

In some configurations, the first coupling arrangement comprises a first connector on the first upstanding member that is removably engageable with a complementary second connector on the upper transverse connecting member, and the second coupling arrangement comprises a third connector on the second upstanding member that is removably engageable with a complementary fourth connector on the upper transverse connecting member.

In some configurations, the first connector is engageable with the second connector by pushing the first upstanding member and the upper transverse connecting member together, and the third connector is engageable with the fourth connector by pushing the second upstanding member and the upper transverse connecting member together.

In some configurations, the first connector cannot be disengaged from the second connector, and the third connector cannot be disengaged from the fourth connector, solely by pulling the upper transverse connecting member away from the first component and the second component.

In some configurations, the first connector is different from the third connector, and the second connector is different from the fourth connector, so that the first connector cannot engage with the fourth connector and so that the second connector cannot engage with the third connector.

In some configurations, the first connector is the same as the third connector, and the second connector is the same as the fourth connector, so that the first connector can engage with the fourth connector and so that the second connector can engage with the third connector.

In some configurations, the fifth connector is the same as the seventh connector, and the sixth connector is the same as the eighth connector, so that the fifth connector can engage with the eighth connector and so that the seventh connector can engage with the sixth connector.

In some configurations, the support apparatus comprises a third coupling arrangement that removably couples the first end of the arm to the base and a fourth coupling arrangement that removably couples the second end of the arm to the base, wherein the third coupling arrangement comprises a fifth connector on the base that is removably engageable with a sixth connector on the arm, and wherein the fourth coupling arrangement comprises a seventh connector on the base that is removably engageable with a complementary eighth connector on the arm.

In some configurations, the fifth connector is engageable with the sixth connector, and the seventh connector is engageable with the eighth connector, by pushing the arm and the base together.

In some configurations, the fifth connector cannot be disengaged from the sixth connector, and the seventh connector cannot be disengaged from the eighth connector, solely by pulling the arm away from the base.

In some configurations, the fifth connector is different from the seventh connector, and the sixth connector is different from the eighth connector, so that the fifth connector cannot engage with the eighth connector and so that the seventh connector cannot engage with the sixth connector.

In some configurations, the fifth connector is the same as the seventh connector, and the sixth connector is the same as the eighth connector, so that the fifth connector can engage with the eighth connector and so that the seventh connector can engage with the sixth connector.

In some configurations, the connectors of the first and second coupling arrangements cannot be engaged with the connectors of the third and fourth coupling arrangements.

Additionally, in accordance with certain features, aspects and advantages of at least one of the embodiments disclosed herein, the combination of the support apparatus, a first or second breathing assistance apparatus, and a liquid container for holding liquid and supplying liquid to a humidifier liquid chamber of the breathing assistance apparatus is disclosed.

Additionally, in accordance with certain features, aspects and advantages of at least one of the embodiments disclosed herein, a support apparatus for supporting an accessory of a breathing assistance apparatus, such as a conduit and/or patient interface, is disclosed, the support apparatus comprising:
 a mount to couple with a breathing assistance apparatus; and
 a lower upstanding member extending upwardly from the mount, an intermediate connecting portion at an upper end of the lower upstanding member, and an upper upstanding member extending upwardly from the intermediate connecting portion, wherein the upper upstanding member is offset from the lower upstanding member and is substantially parallel to the lower upstanding member.

In some configurations, the support apparatus comprises a mechanical feature on the upper upstanding member for holding an accessory of a breathing assistance apparatus, and wherein the at least one mechanical feature has a shape that is complementary to the shape of the accessory.

In some configurations, the mechanical feature is positioned substantially directly above the lower upstanding member.

In some configurations, the support apparatus further comprises an accessory support extension that is configured to couple to the mechanical feature.

In some configurations, the support apparatus comprises a second lower upstanding member, a second intermediate connecting portion at an upper end of the second lower upstanding member, and a second upper upstanding member extending upwardly from the second intermediate connecting portion, wherein the second upper upstanding member is offset from the second lower upstanding member, wherein the second upper upstanding member is substantially parallel to the second upstanding member.

In some configurations, the support apparatus comprises a base that is configured to rest on a support surface, and the lower upstanding member and the upper upstanding member are configured to extend in a substantially vertical direction when the base is resting on a support surface.

In some configurations, the second lower upstanding member and the second upper upstanding member are configured to extend in a substantially vertical direction when the base is resting on a support surface.

Additionally, in accordance with certain features, aspects and advantages of at least one of the embodiments disclosed herein, the combination of the support apparatus, a breathing assistance apparatus, and a liquid container for holding liquid and supplying liquid to a humidifier liquid chamber of the breathing assistance apparatus is disclosed.

Additionally, in accordance with certain features, aspects and advantages of at least one of the embodiments disclosed herein, a support apparatus for a breathing assistance apparatus is disclosed, the support apparatus comprising:
 a base having ends and a transverse outer dimension;
 a mount that is configured to releasably couple the support apparatus with a breathing assistance apparatus;
 and an upstanding component that extends upwardly from the base from a location that is spaced from the ends of the base, the upstanding component comprising a transversely extending handle that is configured to enable the support apparatus and a releasably coupled breathing assistance apparatus to be lifted and carried by a user, wherein the handle has a length that is shorter than the transverse outer dimension of the base.

In some configurations, the upstanding component comprises a first upstanding member that comprises a first end at or adjacent to a first side of the base, and a second upstanding member that comprises a second end at or adjacent an opposite second side of the base.

In some configurations, the upstanding component comprises an upper transverse connecting member that extends between and connects upper ends of the first upstanding member and the second upstanding member, wherein the upper transverse connecting member forms the handle.

In some configurations, each side of the upstanding component comprises a lower upstanding member extending upwardly from the base, an intermediate connecting portion at an upper end of the lower upstanding member, and an upper upstanding member extending upwardly from the intermediate connecting portion, wherein the upper upstanding member is offset from the lower upstanding member.

In some configurations, the upper upstanding members are spaced closer together than the lower upstanding members.

In some configurations, the lower upstanding members are removably coupled to the base.

In some configurations, wherein the handle extends between and connects upper ends of the upper upstanding members.

In some configurations, the base is configured to rest on a support surface, and wherein the handle is substantially parallel to the base.

In some configurations, the upstanding component is configured to extend in a substantially vertical direction when the base is resting on a support surface.

Additionally, in accordance with certain features, aspects and advantages of at least one of the embodiments disclosed herein, the combination of the support apparatus, a breathing assistance apparatus, and a liquid container for holding liquid and supplying liquid to a humidifier liquid chamber of the breathing assistance apparatus is disclosed.

Additionally, in accordance with certain features, aspects and advantages of at least one of the embodiments disclosed herein, a support apparatus for supporting an accessory of a breathing assistance apparatus, such as a conduit and/or patient interface, is disclosed, the support apparatus comprising:

a mount that is configured to releasably couple the support apparatus with a breathing assistance apparatus;

an upstanding component extending upwardly from the mount, the upstanding component comprising a handle, the handle configured to enable the support apparatus and a releasably coupled breathing assistance apparatus to be lifted and carried by a user;

a first mechanical feature on the upstanding component, the first mechanical feature extending in a first direction;

a second mechanical feature on the upstanding component, the second mechanical feature extending in a second direction that is substantially opposite to the first direction;

wherein the first and second mechanical features are configured so that an accessory of a breathing assistance apparatus can be wrapped around the first and second mechanical features in a loop.

In some configurations, the first mechanical feature extends upwardly so that an accessory of a breathing assistance apparatus can be hung from the first mechanical feature without using the second mechanical feature.

In some configurations, at least one of the mechanical features comprises a base portion that extends from the upstanding component, and a distal support portion that is configured to support the accessory between the distal support portion and the upstanding component, wherein a length of the distal support portion is at least 1.5 times a width of a slot formed between the distal support portion and the upstanding component.

In some configurations, the support apparatus further comprises an accessory support extension that is configured to couple to the first mechanical feature.

Additionally, in accordance with certain features, aspects and advantages of at least one of the embodiments disclosed herein, the combination of the support apparatus, a breathing assistance apparatus, and a liquid container for holding liquid and supplying liquid to a humidifier liquid chamber of the breathing assistance apparatus is disclosed.

Additionally, in accordance with certain features, aspects and advantages of at least one of the embodiments disclosed herein, the combination of a support apparatus and a removable shroud is disclosed, the combination comprising:

a support apparatus for a breathing assistance apparatus comprising:

a base;

a mount that is configured to releasably couple the support apparatus with a breathing assistance apparatus;

a handle that is configured to enable the support apparatus and a releasably coupled breathing assistance apparatus to be lifted and carried by a user; and a removable shroud that is arranged to cover a substantial part of the support apparatus and a releasably coupled breathing assistance apparatus, wherein the shroud comprises an opening through which the handle can pass as the cover is placed on the support apparatus, such that the handle is accessible from an exterior of the shroud.

In some configurations, the shroud is flexible.

In some configurations, the shroud comprises a plastic, fabric, or textile material.

In some configurations, the shroud comprises at least one tab to substantially cover the opening when the cover is in place on the support apparatus.

In some configurations, the shroud comprises two opposed tabs to substantially cover the opening when the cover is in place on the support apparatus.

In some configurations, the tab(s) is/are flexible.

In some configurations, the shroud comprises a fastening arrangement to releasably fasten the tab(s) in position to substantially cover the opening.

In some configurations, the shroud comprises two opposed tabs, and wherein the fastening mechanism comprises a hook and loop fastener on the tabs.

In some configurations, the combination further comprises a breathing assistance apparatus and a liquid container for holding liquid and supplying liquid to a humidifier liquid chamber of the breathing assistance apparatus.

Additionally, in accordance with certain features, aspects and advantages of at least one of the embodiments disclosed herein, a container for holding liquid is disclosed, the container comprising:

a body for holding liquid, wherein the body has a fixed shape, whether or not the container is holding liquid;

a first engagement feature, the first engagement feature configured to engage with a complementary second engagement feature of a support apparatus to couple the container with the support apparatus, wherein either the first engagement feature comprises a slot or recess to engage with a support portion of the second engagement feature that extends in a first, upward direction, or alternatively the first engagement feature comprises a support portion that extends in a second, downward direction to engage with a slot or recess of the second engagement feature.

In some configurations, the container is configured to couple with the support apparatus by moving the container downwardly relative to the support apparatus.

In some configurations, the body is made of a rigid material.

In some configurations, the container comprises a plurality of first engagement features to engage with a plurality of complementary second engagement features of the support apparatus.

In some configurations, either the first engagement features comprise slots or recesses to engage with respective support portions of the second engagement features that extend in an upward direction from respective portions of the support apparatus; the first engagement features comprise support portions that extend in a downward direction to engage with respective slots or recesses of the second engagement features; or one first engagement feature comprises a slot or recess to engage with a support portion of one second engagement feature that extends in an upward direction and another first engagement feature comprises a support portion that extends in a downward direction to engage with a slot or recess of another second engagement feature.

In some configurations, the first engagement features are located at or adjacent opposite sides of the body.

In some configurations, the container has a liquid outlet.

In some configurations, the liquid outlet comprises, or is configured to connect to, a liquid conduit adapter.

In some configurations, the liquid conduit adapter is configured to connect to a liquid conduit of a humidifier liquid chamber.

In some configurations, the liquid conduit adapter is configured to connect to a spike connector of the liquid conduit.

In some configurations, the body has a base, and the liquid outlet is located at the base of the body.

In some configurations, the liquid outlet is located at or adjacent a side of the body.

In some configurations, the liquid outlet is located at or adjacent a rear of the body.

In some configurations, the liquid outlet is angled towards the side of the body.

In some configurations, a portion of the base of the body is sloped.

In some configurations, the liquid outlet is located at or adjacent a bottom of the sloped portion.

Additionally, in accordance with certain features, aspects and advantages of at least one of the embodiments disclosed herein, the combination of a support apparatus, a breathing assistance apparatus, and the container is disclosed, the combination comprising:
- a support apparatus for a breathing assistance apparatus, the support apparatus comprising one or more second engagement feature;
- a breathing assistance apparatus having a display, the breathing assistance apparatus coupled with the support apparatus; and
- the container coupled with the support apparatus, wherein a spacing is provided between the base of the body and the display of the breathing assistance apparatus, and wherein the sloped portion is configured to minimise or avoid obstruction of the display by the container.

In some configurations, the body comprises an upper housing and a lower housing, wherein the upper housing and lower housing are coupled together.

In some configurations, the first engagement feature(s) is/are located on the lower housing.

In some configurations, the container comprises a liquid refilling aperture.

In some configurations, the liquid refilling aperture is located at a top of the body.

In some configurations, the liquid refilling aperture has a tapered shape in which an entrance of the liquid refilling aperture has a larger dimension than an exit of the liquid refilling aperture.

In some configurations, the container comprises a lid to engage with the liquid refilling aperture.

In some configurations, the lid substantially seals the liquid refilling aperture when the lid is engaged with the liquid refilling aperture.

In some configurations, the lid is connected to or connectable to the body.

In some configurations, the lid is biased into engagement with the liquid refilling aperture.

In some configurations, the container comprises an auxiliary aperture.

In some configurations, the auxiliary aperture is located above any liquid volume in the container.

In some configurations, the auxiliary aperture is configured to allow ambient air to enter the container while liquid is exiting the container.

Additionally, in accordance with certain features, aspects and advantages of at least one of the embodiments disclosed herein, a container for holding liquid and for coupling to a support apparatus having two upstanding members, an upper transverse connecting member that extends between and connects upper ends of the two upstanding members, and second engagement features on the upstanding members that are located below the upper transverse connecting member is disclosed, the container comprising:
- a body for holding liquid;
- a plurality of first engagement features, the plurality of first engagement features configured to engage with the second engagement features on the upstanding members of the support apparatus to couple the container with the support apparatus.

In some configurations, the upper transverse connecting member forms a handle.

In some configurations, the engagement features are configured so that a space is provided between the upper transverse connecting member and the container when the container is coupled to the support apparatus.

In some configurations, the container is configured to couple with the support apparatus by moving the container downwardly relative to the support apparatus.

In some configurations, the container is configured to initially be moved horizontally relative to the support apparatus until the first engagement features are located above the second engagement features, and then be moved downwardly relative to the support apparatus to couple the container to the support apparatus.

In some configurations, the body has a fixed shape, whether or not the container is holding liquid.

In some configurations, the body is made of a rigid material.

In some configurations, either the first engagement features comprise slots or recesses to engage with respective support portions of the second engagement features that extend in an upward direction from respective portions of the support apparatus; the first engagement features comprise support portions that extend in a downward direction to engage with respective slots or recesses of the second engagement features; or one first engagement feature comprises a slot or recess to engage with a support portion of one second engagement feature that extends in an upward direction and another first engagement feature comprises a support portion that extends in a downward direction to engage with a slot or recess of another second engagement feature.

In some configurations, the first engagement features are located at or adjacent opposite sides of the body.

In some configurations, the container has a liquid outlet.

In some configurations, the liquid outlet comprises, or is configured to connect to, a liquid conduit adapter.

In some configurations, the liquid conduit adapter is configured to connect to a liquid conduit of a humidifier liquid chamber.

In some configurations, the liquid conduit adapter is configured to connect to a spike connector of the liquid conduit.

In some configurations, the body has a base, and the liquid outlet is located at the base of the body.

In some configurations, the liquid outlet is located at or adjacent a side of the body.

In some configurations, the liquid outlet is located at or adjacent a rear of the body.

In some configurations, the liquid outlet is angled towards the side of the body.

In some configurations, a portion of the base of the body is sloped.

In some configurations, the liquid outlet is located at or adjacent a bottom of the sloped portion.

Additionally, in accordance with certain features, aspects and advantages of at least one of the embodiments disclosed herein, the combination of a support apparatus, a breathing assistance apparatus, and the container disclosed, the combination comprising:
- a support apparatus for a breathing assistance apparatus, the support apparatus comprising one or more second engagement feature;
- a breathing assistance apparatus having a display, the breathing assistance apparatus coupled with the support apparatus;
- and the container coupled with the support apparatus, wherein a spacing is provided between the base of the body and the display of the breathing assistance apparatus, and wherein the sloped portion is configured to minimise or avoid obstruction of the display by the container.

In some configurations, the body comprises an upper housing and a lower housing, wherein the upper housing and lower housing are coupled together.

In some configurations, the first engagement features are located on the lower housing.

In some configurations, the container comprises a liquid refilling aperture.

In some configurations, the liquid refilling aperture is located at a top of the body.

In some configurations, the liquid refilling aperture has a tapered shape in which an entrance of the liquid refilling aperture has a larger dimension than an exit of the liquid refilling aperture.

In some configurations, the container comprises a lid to engage with the liquid refilling aperture.

In some configurations, the lid substantially seals the liquid refilling aperture when the lid is engaged with the liquid refilling aperture.

In some configurations, the lid is connected to or connectable to the body.

In some configurations, the lid is biased into engagement with the liquid refilling aperture.

In some configurations, the container comprises an auxiliary aperture.

In some configurations, the auxiliary aperture is located above any liquid volume in the container.

In some configurations, the auxiliary aperture is configured to allow ambient air to enter the container while liquid is exiting the container.

Additionally, in accordance with certain features, aspects and advantages of at least one of the embodiments disclosed herein, a container for holding liquid is disclosed, the container comprising:
- a body for holding liquid, the body comprising a base, wherein a portion of the base is sloped, and wherein the body has a fixed shape, whether or not the container is holding liquid;
- and a liquid outlet for supplying liquid to a humidifier liquid chamber, the liquid outlet located at the base of the body.

In some configurations, the body is made of a rigid material.

In some configurations, the liquid outlet is located at or adjacent a bottom of the sloped portion.

In some configurations, the liquid outlet is located at a bottom of the base of the body.

In some configurations, the container is configured to couple to a support apparatus.

In some configurations, the support apparatus is configured to couple with a breathing assistance apparatus having a display.

Additionally, in accordance with certain features, aspects and advantages of at least one of the embodiments disclosed herein, the combination of a support apparatus, a breathing assistance apparatus, and the container disclosed, the combination comprising:
- a support apparatus for a breathing assistance apparatus;
- a breathing assistance apparatus having a display, the breathing assistance apparatus coupled with the support apparatus;
- and the container coupled with the support apparatus, wherein a spacing is provided between the base of the body and the display of the breathing assistance apparatus, and wherein the sloped portion is configured to minimise or avoid obstruction of the display by the container.

In some configurations, the sloped portion is substantially planar and is oriented at an angle above horizontal and less than vertical.

In some configurations, a portion of the base is horizontal.

In some configurations, the liquid outlet is located at the horizontal portion of the base.

In some configurations, the liquid outlet comprises, or is configured to connect to, a liquid conduit adapter.

In some configurations, the liquid conduit adapter is configured to connect to a liquid conduit of a humidifier liquid chamber.

In some configurations, the liquid conduit adapter is configured to connect to a spike connector of the liquid conduit.

In some configurations, the liquid outlet is located at or adjacent a side of the container.

In some configurations, the liquid outlet is located at or adjacent a rear of the container.

In some configurations, the liquid outlet is angled towards the side of the container.

Additionally, in accordance with certain features, aspects and advantages of at least one of the embodiments disclosed herein, the combination of a support apparatus, a breathing assistance apparatus, a humidifier liquid chamber, and the container disclosed, the combination comprising:
- a support apparatus for a breathing assistance apparatus;
- a breathing assistance apparatus having a display, the breathing assistance apparatus coupled with the support apparatus;
- a humidifier liquid chamber;
- and the container coupled with the support apparatus, wherein a spacing is provided between the base of the body and the display of the breathing assistance apparatus, and wherein the sloped portion is configured to minimise or avoid obstruction of the display by the container, and wherein the container is configured to supply liquid to the humidifier liquid chamber from the liquid outlet of the container.

Additionally, in accordance with certain features, aspects and advantages of at least one of the embodiments disclosed herein, a container for holding liquid is disclosed, the container comprising:
- a body for holding liquid, wherein the body has a fixed shape, whether or not the container is holding liquid;
- a liquid outlet for supplying liquid to a humidifier liquid chamber;
- and a venting aperture that is configured to allow ambient air to enter the container while liquid is exiting the container.

In some configurations, the body is made of a rigid material.

In some configurations, the venting aperture is located above any liquid volume in the container.

In some configurations, the body has a base, and the liquid outlet is located at the base of the body.

In some configurations, the liquid outlet is located at or adjacent a side of the body.

In some configurations, the liquid outlet is located at or adjacent a rear of the body.

In some configurations, the liquid outlet is angled towards the side of the body.

In some configurations, a portion of the base of the body is sloped.

In some configurations, the liquid outlet is located at or adjacent a bottom of the sloped portion.

In some configurations, the container comprises a liquid refilling aperture.

In some configurations, the liquid refilling aperture is located at a top of the body.

In some configurations, the liquid refilling aperture has a tapered shape in which an entrance of the liquid refilling aperture has a larger dimension than an exit of the liquid refilling aperture.

In some configurations, the container comprises a lid to engage with the liquid refilling aperture.

In some configurations, the lid substantially seals the liquid refilling aperture when the lid is engaged with the liquid refilling aperture, and wherein the venting aperture is an auxiliary aperture in the body.

In some configurations, the auxiliary aperture is located in the lid.

In some configurations, the lid and the liquid refilling aperture are configured such that the venting aperture is provided by a space between the lid and the liquid refilling aperture when the lid is engaged with the liquid refilling aperture.

In some configurations, the lid is connected to or connectable to the body.

In some configurations, the lid is biased into engagement with the liquid refilling aperture.

In some configurations, the liquid outlet comprises, or is configured to connect to, a liquid conduit adapter.

In some configurations, the liquid conduit adapter is configured to connect to a liquid conduit of a liquid chamber.

In some configurations, the liquid conduit adapter is configured to connect to a spike connector of the liquid conduit.

Additionally, in accordance with certain features, aspects and advantages of at least one of the embodiments disclosed herein, the combination of a humidifier liquid chamber and the container is disclosed, the combination comprising:

a humidifier liquid chamber;

and the container that is configured to supply liquid to the humidifier liquid chamber from the liquid outlet of the container.

In some configurations, the humidifier liquid chamber is part or, or is associated with, a breathing assistance apparatus.

In some configurations, the liquid chamber is coupled to the support apparatus.

In some configurations, the breathing assistance apparatus is coupled to the support apparatus.

Additionally, in accordance with certain features, aspects and advantages of at least one of the embodiments disclosed herein, a container for holding liquid is disclosed, the container comprising:

a body for holding liquid;

a liquid outlet configured to be in liquid communication with a humidifier liquid chamber;

a liquid refilling aperture;

and a lid to engage with the liquid refilling aperture, wherein the lid is connected to or connectable to the body to be biased into engagement with the liquid refilling aperture.

In some configurations, the liquid refilling aperture is located at a top of the body.

In some configurations, the liquid refilling aperture has a tapered shape in which an entrance of the liquid refilling aperture has a larger dimension than an exit of the liquid refilling aperture.

In some configurations, the lid substantially seals the liquid refilling aperture when the lid is engaged with the liquid refilling aperture.

In some configurations, the container comprises an auxiliary aperture that is configured to allow ambient air to enter the container while liquid is exiting the container.

In some configurations, the auxiliary aperture is located above any liquid volume in the container.

In some configurations, the body has a base, and wherein the container comprises a liquid outlet located at the base of the body.

In some configurations, the liquid outlet is located at or adjacent a side of the body.

In some configurations, the liquid outlet is located at or adjacent a rear of the body.

In some configurations, the liquid outlet is angled towards the side of the body.

In some configurations, a portion of the base of the body is sloped.

In some configurations, the liquid outlet is located at or adjacent a bottom of the sloped portion.

In some configurations, the liquid outlet comprises, or is configured to connect to, a liquid conduit adapter.

In some configurations, the liquid conduit adapter is configured to connect to a liquid conduit of a liquid chamber.

In some configurations, the liquid conduit adapter is configured to connect to a spike connector of the liquid conduit.

Additionally, in accordance with certain features, aspects and advantages of at least one of the embodiments disclosed herein, the combination of a humidifier liquid chamber and the container is disclosed, the combination comprising:

a humidifier liquid chamber;

and the container that is configured to supply liquid to the humidifier liquid chamber from the liquid outlet of the container.

In some configurations, the humidifier liquid chamber is part or, or is associated with, a breathing assistance apparatus.

In some configurations, the liquid container is coupled to the support apparatus.

Additionally, in accordance with certain features, aspects and advantages of at least one of the embodiments disclosed herein, a tray for supporting a liquid container or liquid bag for supplying liquid to a humidifier liquid chamber is disclosed, the tray configured for coupling to a support apparatus having an upstanding member, an upper transverse member that extends from an upper end of the upstanding member, and a second engagement feature on the upstanding member that is located below the upper transverse member, the tray comprising:

a tray body for supporting the liquid container or liquid bag;

a first engagement feature, the first engagement feature configured to engage with the second engagement feature on the upstanding member of the support apparatus to couple the tray with the support apparatus.

In some configurations, the upper transverse member forms a handle.

In some configurations, the engagement features are configured so that a space is provided between the upper transverse member and the tray when the tray is coupled to the support apparatus.

In some configurations, the tray is configured to couple with the support apparatus by moving the tray downwardly relative to the support apparatus.

In some configurations, the tray is configured to initially be moved horizontally relative to the support apparatus until the first engagement feature is located above the second engagement feature, and then be moved downwardly relative to the support apparatus to couple the tray to the support apparatus.

In some configurations, the support apparatus comprises two upstanding members and second engagement features on the upstanding members, wherein the upper transverse member extends between and connects upper ends of the two upstanding members, and wherein the tray comprises a plurality of first engagement features configured to engage with the second engagement features on the upstanding members of the support apparatus to couple the tray with the support apparatus.

In some configurations, the first engagement features comprise slots or recesses to engage with respective support portions of the second engagement features that extend in an upward direction from respective portions of the support apparatus; the first engagement features comprise support portions that extend in a downward direction to engage with respective slots or recesses of the second engagement features; or one first engagement feature comprises a slot or recess to engage with a support portion of one second engagement feature that extends in an upward direction and another first engagement feature comprises a support portion that extends in a downward direction to engage with a slot or recess of another second engagement feature.

In some configurations, the first engagement features are located at or adjacent opposite sides of the tray body.

In some configurations, the tray comprises an upwardly projecting rim extending along at least part of the tray body, at or adjacent the periphery of the tray body.

In some configurations, the upwardly projecting rim extends around substantially the entire tray body.

Additionally, in accordance with certain features, aspects and advantages of at least one of the embodiments disclosed herein, the combination of a support apparatus, a breathing assistance apparatus, and the tray is disclosed, the combination comprising:

a support apparatus for a breathing assistance apparatus, the support apparatus comprising one or more second engagement feature;

a breathing assistance apparatus coupled with the support apparatus;

and the tray coupled with the support apparatus.

In some configurations, the combination comprises a liquid container or liquid bag supported by the tray.

Features from one or more embodiments or configurations may be combined with features of one or more other embodiments or configurations. Additionally, more than one embodiment may be used together during a process of respiratory support of a patient.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

It should be understood that alternative embodiments or configurations may comprise any or all combinations of two or more of the parts, elements or features illustrated, described or referred to in this specification.

This invention may also be said broadly to consist in the parts, elements and features referred to or indicated in the specification of the application, individually or collectively, and any or all combinations of any two or more said parts, elements or features.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth.

The term 'comprising' as used in this specification means 'consisting at least in part of'. When interpreting each statement in this specification that includes the term 'comprising', features other than that or those prefaced by the term may also be present. Related terms such as 'comprise' and 'comprises' are to be interpreted in the same manner.

As used herein the term '(s)' following a noun means the plural and/or singular form of that noun.

As used herein the term 'and/or' means 'and' or 'or', or where the context allows both.

The invention consists in the foregoing and also envisages constructions of which the following gives examples only.

BRIEF DESCRIPTION OF THE DRAWINGS

Specific embodiments and modifications thereof will become apparent to those skilled in the art from the detailed description herein having reference to the figures that follow, of which.

DETAILED DESCRIPTION OF SPECIFIC EMBODIMENTS

Figure 1:
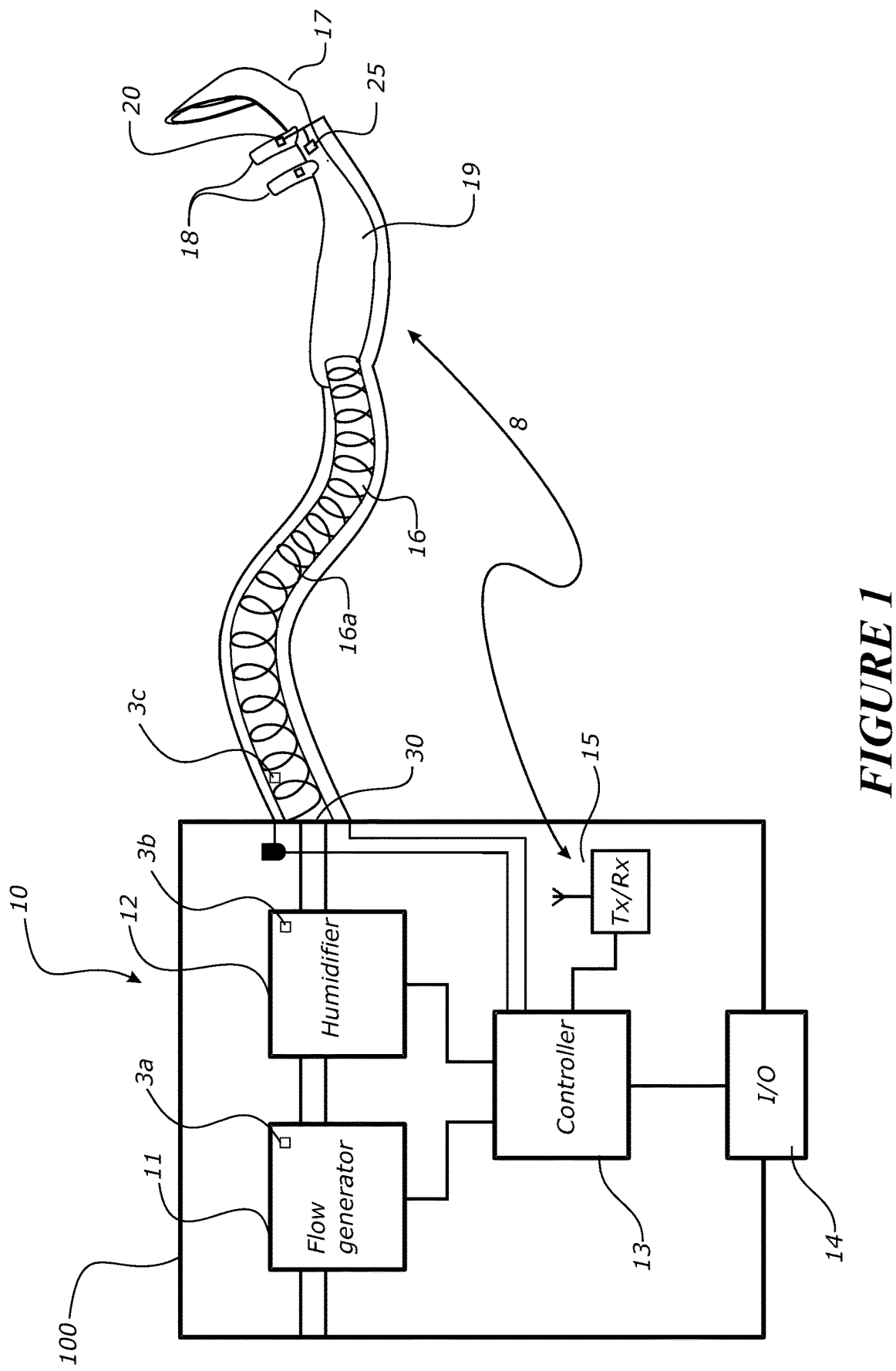
FIG. 1 shows in diagrammatic form a breathing assistance apparatus.

A breathing assistance apparatus 10 for delivering a flow of gas (which may contain one or more gases) to a patient is shown in FIG. 1.

The apparatus 10 could, for example, be a CPAP apparatus or a high flow apparatus. An exemplary CPAP apparatus is described in WO 2011/056080. The contents of that specification are incorporated herein in their entirety by way of reference.

A CPAP apparatus is a gases supply and optionally gases humidification apparatus. The apparatus is operable to provide respiratory assistance to patients or users who require a supply of gas (humidified or otherwise) at positive pressure for the treatment of diseases such as Obstructive Sleep Apnea (OSA), snoring, or Chronic Obstructive Pulmonary Disease (COPD) and the like. A CPAP apparatus would typically include a humidifier liquid chamber, so as to form a combined assisted breathing unit and humidifier.

CPAP apparatuses, when used with a humidifier, typically have a structure where gases at a required pressure are delivered from an assisted breathing unit or blower unit to a liquid chamber downstream from the blower. As the gases pass through the liquid chamber, they become saturated with liquid vapour (e.g. water vapour). A flexible tubular gases conduit delivers the gases to a user or patient downstream from the humidifier chamber.

A high flow apparatus may be used to deliver a high gas flow or high flow therapy to a patient to assist with breathing and/or treat breathing disorders including chronic obstructive pulmonary disease (COPD). A high flow apparatus includes a gases supply and typically includes a humidification apparatus.

The breathing assistance apparatuses typically have one or more accessories such as a breathing conduit and a patient interface such as a cannula or mask for delivering gases to a patient. The conduit enables gases to be delivered from the housing of the breathing assistance apparatus to the patient. For example, the apparatus may be placed on a floor or other support surface, and the patient may be in a bed. The breathing assistance apparatus may have a recess for receipt of a humidifier liquid chamber. The humidifier liquid chamber will receive liquid from, for example, a flexible liquid bag or a container as described herein that provides liquid to the humidifier liquid chamber via one more tubes. Alternatively, the humidifier liquid chamber can be removed and refilled as required. The recess will contain a heater plate to heat a liquid in the humidifier liquid chamber in use, to humidify gases passing through the liquid chamber. The humidified gases are then delivered to the patient.

In general terms, the apparatus 10 comprises a main housing 100 that contains a flow generator 11 in the form of a motor/impeller arrangement, a humidifier 12, a controller 13, and a user I/O interface 14 (comprising, for example, a display and input device(s) such as button(s), a touch screen, or the like). The controller 13 is configured or programmed to control the components of the apparatus, including: operating the flow generator 11 to create a flow of gas (gas flow) for delivery to a patient, operating the humidifier 12 to humidify and/or heat the generated gas flow, receive user input from the user interface 14 for reconfiguration and/or user-defined operation of the apparatus 10, and output information (for example on the display) to the user. The user could be a patient, healthcare professional, or anyone else interested in using the apparatus.

A patient breathing conduit 16 is coupled to a gas flow output 30 in the housing 100 of the breathing assistance apparatus 10, and is coupled to a patient interface 17 such as a nasal cannula with a manifold 19 and nasal prongs 18. Additionally, or alternatively, the patient breathing conduit 16 could be coupled to a face mask. Additionally or alternatively, the patient breathing conduit could be coupled to a nasal pillows mask, and/or a nasal mask, and/or a tracheostomy interface, or any other suitable type of patient interface. The gas flow, which may be humidified, that is generated by the breathing assistance apparatus 10 is delivered to the patient via the patient breathing conduit 16 through the patient interface 17. The patient breathing conduit 16 can have a heater wire 16*a* to heat gas flow passing through to the patient. The heater wire 16*a* is under the control of the controller 13. The patient breathing conduit 16 and/or patient interface 17 can be considered part of the breathing assistance apparatus 10, or alternatively peripheral to it. The breathing assistance apparatus 10, breathing conduit 16, and patient interface 17 may together form a breathing assistance system or, in some configurations, a flow therapy system.

General operation of an exemplary breathing assistance apparatus 10 will be known to those skilled in the art, and need not be described in detail here. However, in general terms, the controller 13 controls the flow generator 11 to generate a gas flow of the desired flow rate, controls one or more valves to control the mix of air and oxygen or other alternative gas, and/or controls the humidifier 12 to humidify the gas flow and/or heat the gas flow to an appropriate level. The gas flow is directed out through the patient breathing conduit 16 and patient interface 17 to the patient. The controller 13 can also control a heating element in the humidifier 12 and/or the heating element 16*a* in the patient breathing conduit 16 to heat the gas to a desired temperature that achieves a desired level of therapy and/or comfort for the patient. The controller 13 can be programmed with, or can determine, a suitable target temperature of the gas flow.

Operation sensors 3*a*, 3*b*, 3*c*, 20, and 25, such as flow, temperature, humidity, and/or pressure sensors, can be placed in various locations in the breathing assistance apparatus 10 and/or the patient breathing conduit 16 and/or cannula 17. Output from the sensors can be received by the controller 13, to assist it to operate the breathing assistance apparatus 10 in a manner that provides optimal therapy. In some configurations, providing optimal therapy includes meeting a patient's inspiratory flow. The apparatus 10 may have a transmitter and/or receiver 15 to enable the controller 13 to receive signals 8 from the sensors and/or to control the various components of the breathing assistance apparatus 10, including but not limited to the flow generator 11, humidifier 12, and heater wire 16*a*, or accessories or peripherals associated with the breathing assistance apparatus 10. Additionally, or alternatively, the transmitter and/or receiver 15 may deliver data to a remote server or enable remote control of the apparatus 10.

The breathing assistance apparatus 10 may be any suitable type of apparatus, but in some configurations may deliver a high gas flow or high flow therapy (of e.g. air, oxygen, other gas mixture, or some combination thereof) to a patient to assist with breathing and/or treat breathing disorders. In some configurations, the gas is or comprises oxygen. In some configurations, the gas comprises a blend of oxygen and ambient air. High flow therapy as discussed herein is intended to be given its typical ordinary meaning as understood by a person of skill in the art which generally refers to a respiratory assistance system delivering a targeted flow of humidified respiratory gases via an intentionally unsealed patient interface with flow rates generally intended to meet or exceed inspiratory flow of a patient. Typical patient interfaces include, but are not limited to, a nasal or tracheal patient interface. Typical flow rates for adults often range from, but are not limited to, about fifteen liters per minute (LPM) to about seventy liters per minute or greater. Typical flow rates for pediatric patients (such as neonates, infants and children) often range from, but are not limited to, about one liter per minute per kilogram of patient weight to about three liters per minute per kilogram of patient weight or greater. High flow therapy can also optionally include gas mixture compositions including supplemental oxygen and/or administration of therapeutic medicaments. High flow therapy is often referred to as nasal high flow (NHF), humidified high flow nasal cannula (HHFNC), high flow nasal oxygen (HFNO), high flow therapy (HFT), or tracheal high flow (THF), among other common names.

For example, in some configurations, for an adult patient 'high flow therapy' may refer to the delivery of gases to a patient at a flow rate of greater than or equal to about 10 liters per minute (10 LPM), such as between about 10 LPM and about 100 LPM, or between about 15 LPM and about 95 LPM, or between about 20 LPM and about 90 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. In some configurations, for a neonatal, infant, or child patient 'high flow therapy' may refer to the delivery of gases to a patient at a flow rate of greater than 1 LPM, such as between about 1 LPM and about 25 LPM, or between about 2 LPM and about 25 LPM, or between about 2 LPM and about 5 LPM, or between about 5 LPM and about 25 LPM, or between about 5 LPM and about 10 LPM, or between about 10 LPM and about 25 LPM, or between about 10 LPM and about 20 LPM, or between about 10 LPM and 15 LPM, or between about 20 LPM and 25 LPM. A high flow therapy apparatus with an adult patient, a neonatal, infant, or child patient, may, in some configurations, deliver gases to the patient at a flow rate of between about 1 LPM and about 100 LPM, or at a flow rate in any of the sub-ranges outlined above. Gases delivered may comprise a percentage of oxygen. In some configurations, the percentage of oxygen in the gases delivered may be between about 20% and about 100%, or between about 30% and about 100%, or between about 40% and about 100%, or between about 50% and about 100%, or between about 60% and about 100%, or between about 70% and about 100%, or between about 80% and about 100%, or between about 90% and about 100%, or about 100%, or 100%.

High flow therapy has been found effective in meeting or exceeding the patient's inspiratory flow, increasing oxygenation of the patient and/or reducing the work of breathing. Additionally, high flow therapy may generate a flushing effect in the nasopharynx such that the anatomical dead space of the upper airways is flushed by the high incoming gas flows. This creates a reservoir of fresh gas available for each and every breath, while minimising re-breathing of carbon dioxide, nitrogen, etc.

In one example for high flow therapy, an unsealed or non-sealing user interface, e.g. a nasal cannula, is used. For CPAP a sealed interface is typically used, e.g. a nasal mask, full face mask, or nasal pillows.

The patient interface may be a non-sealing interface to prevent barotrauma (e.g. tissue damage to the lungs or other organs of the respiratory system due to difference in pressure relative to the atmosphere). The patient interface may be a nasal cannula with a manifold and nasal prongs, and/or a face mask, and/or a nasal pillows mask, and/or a nasal mask, and/or a tracheostomy interface, or any other suitable type of patient interface.

As described below, the breathing assistance apparatus 10 has various features to assist with the functioning, use, and/or configuration of the apparatus 10.

Figure 2:
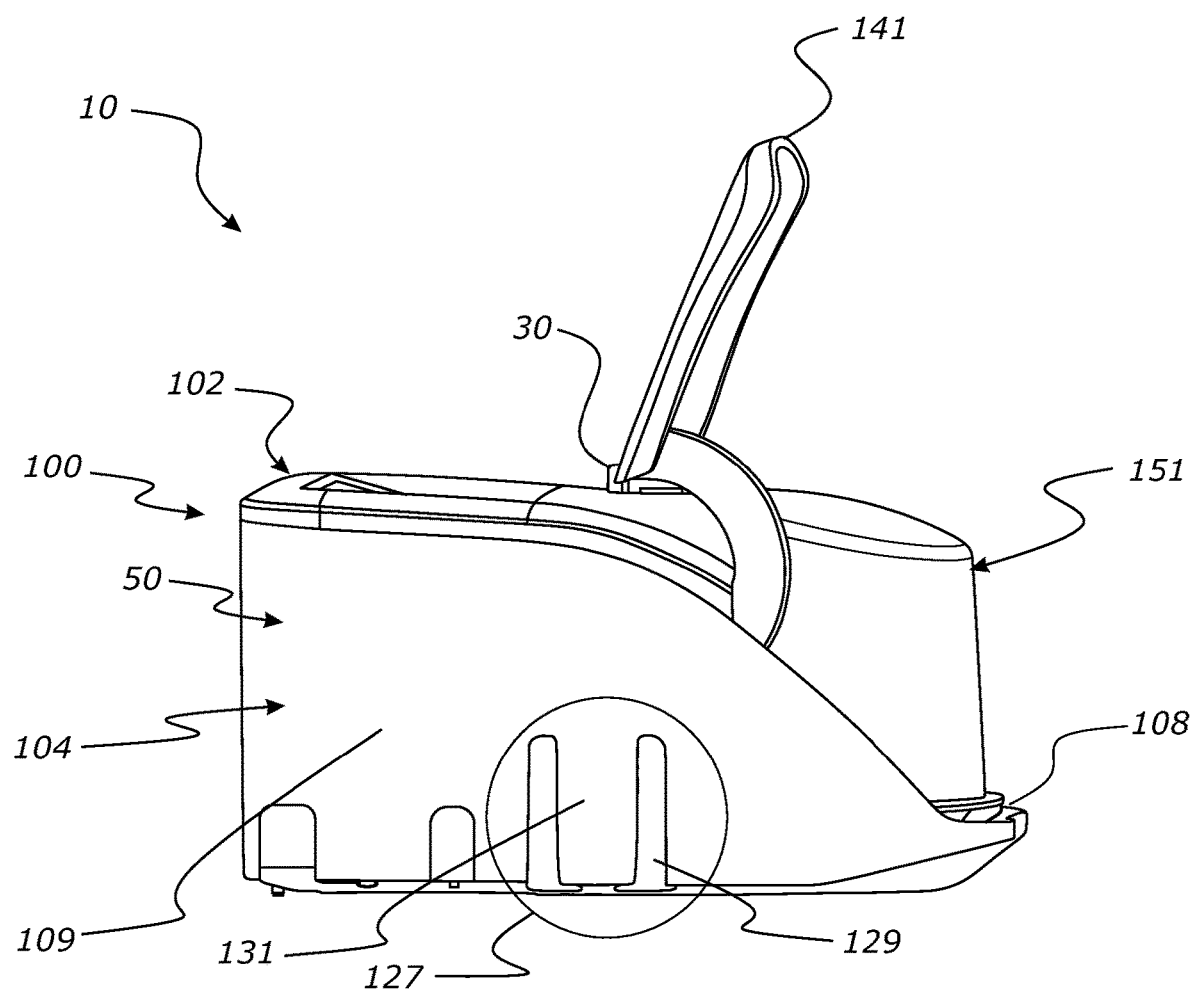
FIG. 2 is a left side view of a first configuration breathing assistance apparatus showing an exemplary location of an integral mount for coupling the first configuration breathing assistance apparatus with a support apparatus.

As shown in FIG. 2, a first configuration breathing assistance apparatus 10 comprises a breathing assistance apparatus base unit 50 having a main housing 100. The main housing 100 has a main housing upper chassis 102 and a main housing lower chassis 104.

The main housing 100 has a peripheral wall arrangement. The peripheral wall arrangement defines a recess that provides humidifier or liquid chamber bay 108 for receipt of a removable humidifier liquid chamber 151. The removable liquid chamber 151 contains a suitable liquid such as water for humidifying gases that will be delivered to a patient.

The apparatus 10 has a tiltable handle/lever 141 that enables a user to lift and carry the apparatus when in a raised position (FIG. 2), and that assists with maintaining the liquid chamber 151 in engagement with the housing 100 when in a lowered position.

In the form shown, the main housing lower chassis 104 peripheral wall arrangement comprises a substantially vertical left side outer wall 109 that is oriented in a front-to-rear direction of the main housing 100, a substantially vertical right side outer wall 111 (FIG. 3), and a substantially vertical rear outer wall 113 that extends between and connects the walls 109, 111. A bottom wall 115 extends between and connects the lower ends of walls 109, 111, 113, and forms a base of the apparatus and a substantially horizontal floor portion of the liquid chamber bay.

The floor portion of the liquid chamber bay 108 has a recess to receive a heater arrangement such as a heater plate or other suitable heating element(s) for heating liquid in the liquid chamber 151 for use during a humidification process.

The main housing lower chassis 104 is attachable to the upper chassis 102, either by suitable fasteners or integrated attachment features such as clips for example. When the main housing lower chassis 104 is attached to the main housing upper chassis 102, the walls of the upper and lower chassis engage with each other.

Figure 3:
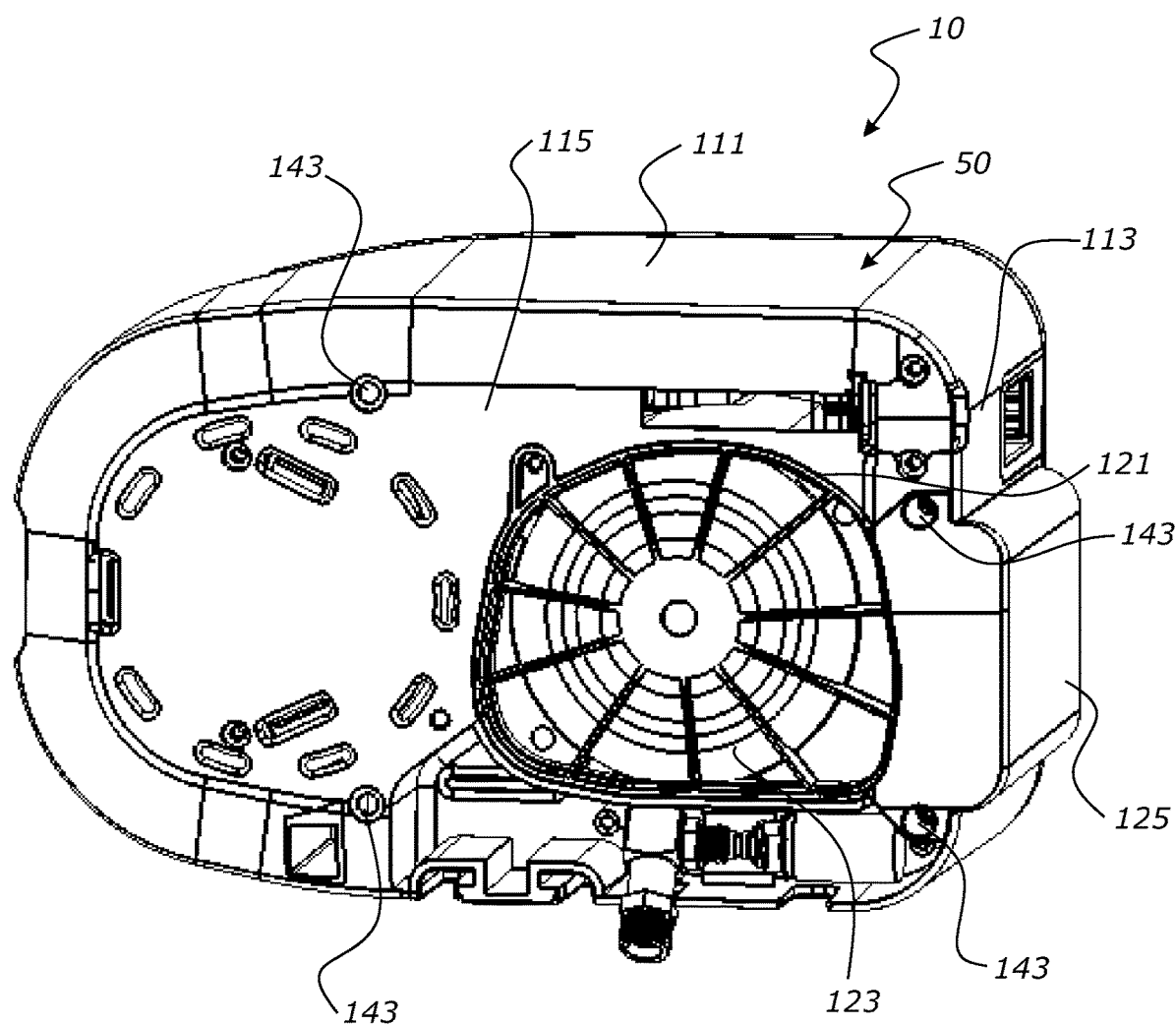
FIG. 3 is an underside perspective view of the first configuration breathing assistance apparatus.
Figure 4:
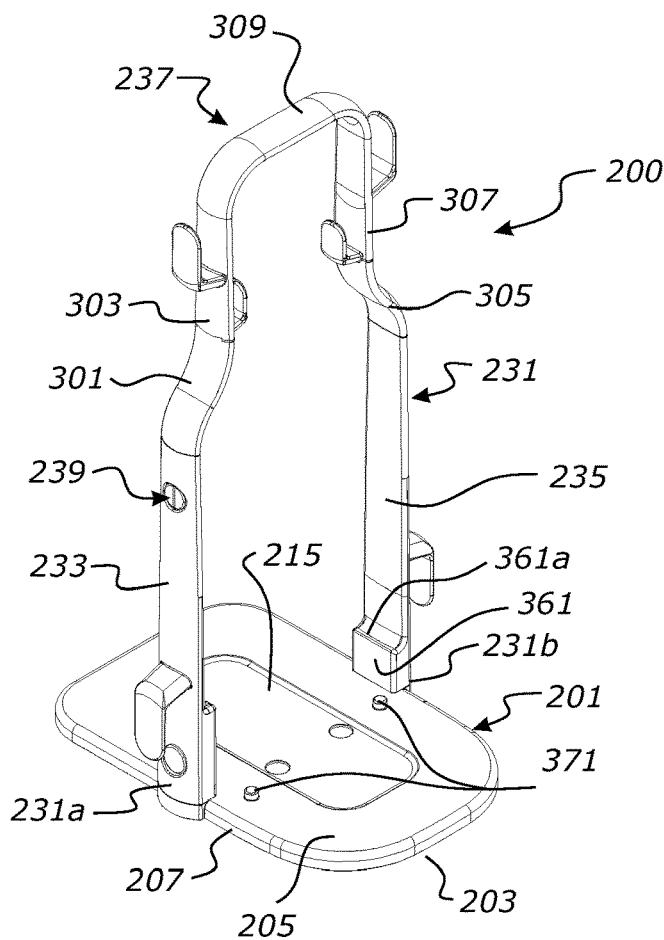
FIG. 4 is a left side/front overhead perspective view showing a support apparatus for the breathing assistance apparatus.
Figure 5:
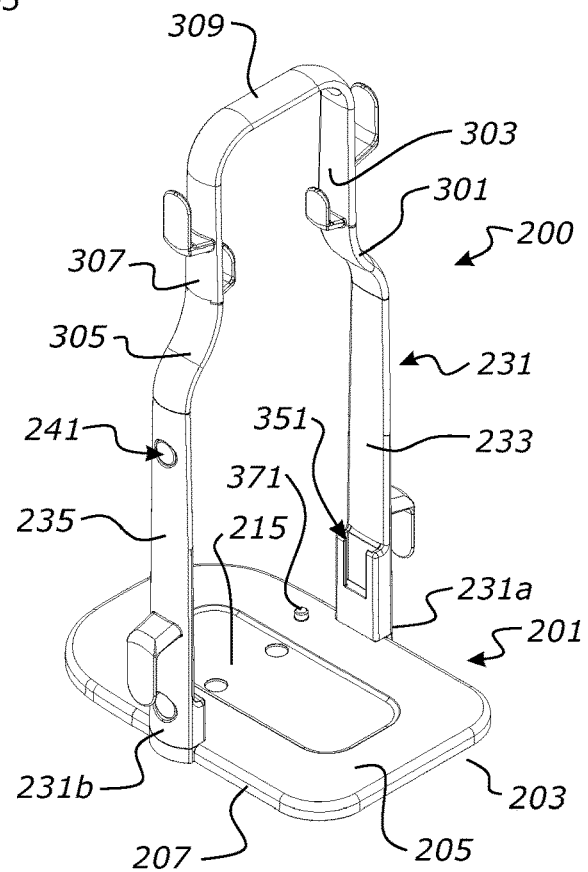
FIG. 5 as a right side/rear overhead perspective view showing the support apparatus.
Figure 6:
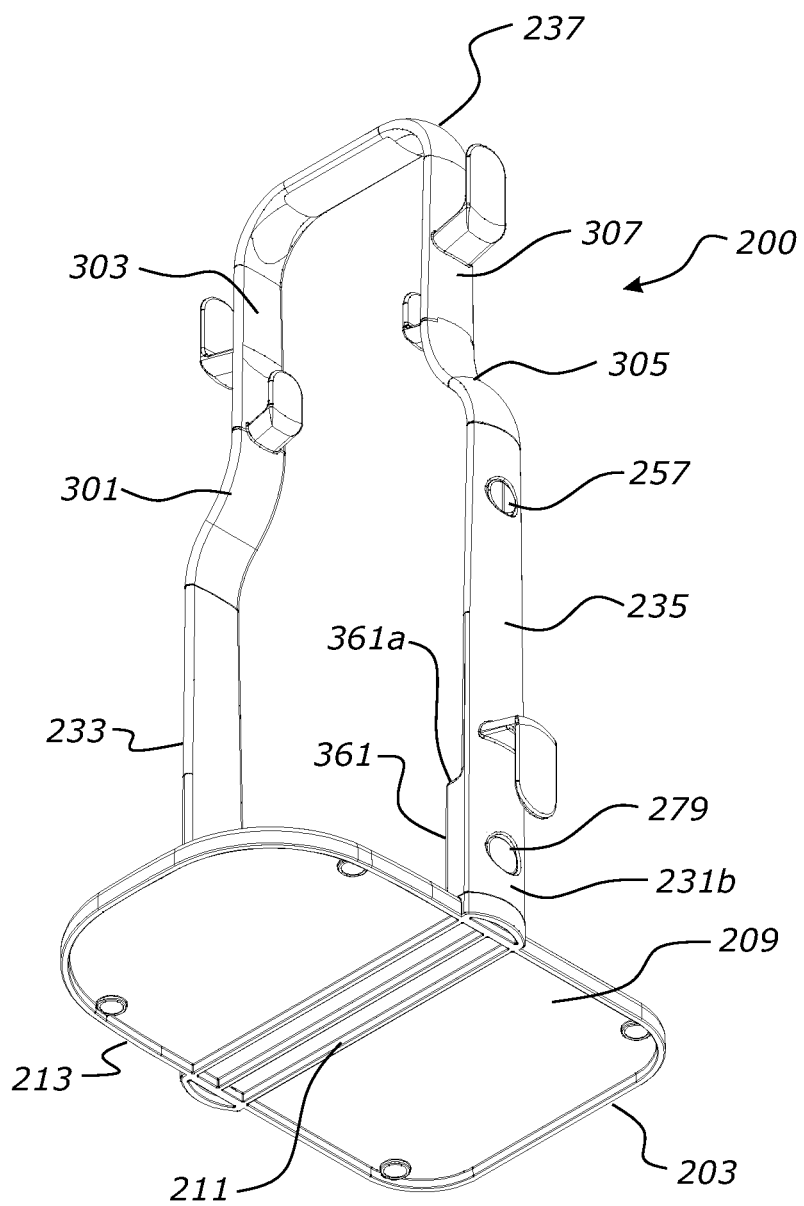
FIG. 6 is a right side/underside perspective view of the support apparatus.

As shown in FIG. 3, the lower chassis 104 has a motor recess 121 for receipt of a motor module which may be permanently inserted in the recess or may be removable from the recess. A recess opening is provided in the bottom wall 115 adjacent a rear edge thereof, for receipt of the removable motor module. FIG. 3 shows a base 123 of the motor module that covers the opening into the motor recess 121. The motor module comprises a motor that forms a blower to cause gas flow, and may comprise one or more sensors to sense properties of the gas passing through the motor module. The motor module may comprise sensor(s) to sense parameters of gases flowing through the motor module.

The motor module and main housing 100 of the apparatus 10 are provided with suitable tubes and/or gas flow passages to deliver gases from one or more gases inlets of the apparatus 10, to a gases inlet port of the liquid chamber 151 to humidify the gases. The gases are delivered from a gases outlet port of the liquid chamber 151 to the patient outlet port 30 and thereby to the patient via the patient breathing conduit 16 and patient interface 17.

In the form shown, the motor recess 121 comprises a recess opening in a bottom wall of the housing. Alternatively, the recess opening could be in a different part of the housing, such as a side, front, or top of the housing.

The apparatus 10 may have a battery 125 to provide power to the apparatus when there is a power outage or for portable use. The battery may be replaceable.

In the form shown, the battery is coupled to an exterior of the back wall of the apparatus main housing 100. This provides a large surface area to cool the battery and reduces the amount of heat entering the apparatus from the battery. Additionally, this configuration reduces the influence of heat generated by components of the apparatus on the battery, particularly when the battery is being charged. In an alternative configuration, the battery may be internally mounted in the main housing.

As shown in FIG. 2, the apparatus 10 has a mounting feature 127 for mounting the apparatus to a first mount 351 of the support apparatus 200 as will be described in more detail below with reference to FIGS. 4 to 31.

The mounting feature 127 may be integrally formed with part of the main housing of the apparatus 10. In the form shown, the mounting feature 127 is integrally formed with the left side wall 109 the lower chassis 104 of the housing. The mounting feature 127 could instead be integrally formed with any of the other walls of the housing, such as a rear wall, right side wall, or other wall.

The side of the apparatus corresponding to the mounting feature 127 comprises a recess 129. A downwardly projecting tongue 131 of the mounting feature 127 has an upper end that is integrally formed with the wall, and is positioned in the recess.

The main housing of the apparatus may be formed from any suitable material that will allow the mounting feature 127 to be integrally formed. For example, the case may be formed from polycarbonate.

The integral mounting feature 127 has greater impact strength compared to an additional, screwed in part. Strengthening of the mounting feature 127 may also be done by, for example, varying the wall thickness, ribbing, or varying internal geometries.

An alternative form breathing assistance apparatus 10 may be a standalone humidifier apparatus comprising a base unit 50 defining a main housing 100 and a humidifier 12.

The standalone humidifier apparatus can deliver heated and humidified gases for various medical procedures, including respiratory therapy, laparoscopy, and the like. These apparatuses can be configured to control temperature and/or humidity. The apparatuses can also include medical circuits comprising various components that can be used to transport heated and/or humidified gases to and/or from patients. For example, in some breathing circuits, gases inhaled by a patient are delivered from a heater-humidifier through an inspiratory tube or conduit. As another example, tubes can deliver humidified gas (commonly $CO_2$) into the abdominal cavity in insufflation circuits. This can help prevent desiccation or 'drying out' of the patient's internal organs, and can decrease the amount of time needed for recovery from surgery. Heater wires may extend inside of at least a portion of the tubing forming the circuit to prevent or at least reduce the likelihood of the formation of significant condensation.

A standalone humidifier apparatus would typically include a base unit 50 and a humidifier liquid chamber 151. The base unit 50 can comprise a heater plate 140. The liquid chamber 151 can be configured to hold a volume of a liquid, such as water. The heater plate can be configured to heat the volume of liquid held within the liquid chamber 151 to produce vapour.

The liquid chamber 151 is removable from the base unit to allow the liquid chamber to be more readily sterilized or disposed, or to re-fill the chamber with liquid. The body of the liquid chamber 151 can be formed from a non-conductive glass or plastics material but the liquid chamber can also include conductive components. For instance, the liquid chamber can include a highly heat-conductive base (for example, an aluminum base) contacting or associated with the heater plate on the heater base.

The base unit can also include electronic controls such as a master controller. In response to user-set humidity or temperature values input via a user interface and other inputs, the master controller determines when (or to what level) to energize the heater plate 140 to heat the liquid within the liquid chamber 151.

The standalone humidifier apparatus can include a flow generator to deliver gases to the liquid chamber. In some configurations, the flow generator can comprise a ventilator, blower, or any other suitable source of pressurized gases suitable for breathing or use in medical procedures. The flow generator may be positioned in the base unit 50.

Alternatively, the standalone humidifier apparatus may comprise just the base unit 50 and the liquid chamber 151, and may be used with a separate or remote flow generator. The base unit 50 may be configured to fluidly connect to the separate or remote flow generator.

Therefore, the flow generator that is used with a standalone humidifier apparatus may be a wall gases source, ventilator, blower, or gas tank for example.

A standalone humidifier apparatus can be used with breathing therapies, positive pressure apparatus, noninvasive ventilation, surgical procedures including but not limited to laparoscopy, and the like. Desirably, the humidifier apparatus can be adapted to supply humidity or vapour to a supply of gases. The humidifier apparatus can be used with continuous, variable, or bi-level PAP systems or other form of respiratory therapy. In some configurations, the humidifier apparatus can be integrated into a system that delivers any such types of therapy.

An exemplary standalone humidifier apparatus is described in WO 2015/038013. The contents of that specification are incorporated herein in their entirety by way of reference.

A second configuration breathing assistance apparatus 10' is shown in FIGS. 14-18A. Unless described below, the features and functionality of the second configuration breathing assistance apparatus 10' are as described above with reference to breathing assistance apparatus 10, and like reference numerals indicate like parts with the addition of a prime ('). In this configuration, the apparatus 10' is not provided with a mounting feature 127 for mounting with the first mount 351 of the support apparatus 200. Instead, the apparatus 10' is provided with a mounting feature 143' of a different configuration from mounting feature 127, to mount with a second mount 371 of the support apparatus 200, as will be described in more detail below with reference to FIGS. 14-18A.

The apparatus 10' is shown coupled to the breathing conduit 16'.

FIGS. 4 to 31 show exemplary configurations of a support apparatus 200 that can be used to support, hold and carry either apparatus 10, 10' and/or one or more accessories of the apparatus 10, 10', such as the conduit 16, 16', patient interface such as a cannula 17, a power cord 103 of the apparatus 10, 10', and/or tube(s) 101a from a liquid bag 101 or liquid container 600 for delivering liquid to the liquid chamber 151 for example. The accessories can be supported in any desired arrangement from the mechanical features 311, 313, 315 of the support apparatus, if the mechanical features do not have a configuration that is specific to a particular accessory.

The support apparatus 200 comprises a stand 201 and a holder 231 in the form of an upstanding arm component.

The stand 201 comprises a horizontally enlarged base 203 having a relatively small vertical dimension and relatively large horizontal dimensions. The base 203 comprises an upper surface 205 and a peripheral wall 207 that extends downwardly from the upper surface 205. The shape of the periphery of the upper surface 205 corresponds substantially to the shape of the housing of the first configuration breathing assistance apparatus 10 in plan view. While in the form shown the base 203 has a generally oblong shape in plan view, the shape of the base 203 may change depending on the shape of the housing of the breathing assistance apparatus 10, 10' that will be supported.

The footprint of the base 203 is larger than the footprint of each breathing assistance apparatus 10, 10' that is to be supported from the support apparatus 200. This provides a bumper to protect the breathing assistance apparatus 10, 10', as bumping the support apparatus 200 against other objects will then result in a collision with the base 203 as opposed to the breathing assistance apparatus 10, 10'. This is particularly important when the carrier and device are being carried, as being carried increases the risk of the carrier and device being bumped into another object.

A holder 231 extends upwardly from the base 203 from a location that is spaced from ends of the base 203. In the form shown, the ends of the holder 231 are centrally located along the sides of the base 203. However, the ends of the holder 203 could be positioned slightly towards one end of the base rather than being positioned at the centre of the sides. For example, the ends of the holder 231 can be positioned towards the front of the holder or towards the rear of the holder. By having the ends of the holder 231 spaced from the ends of the base 203, greater stability is provided when the holder 231 is used to lift the support apparatus 200.

The underside of the base 203 of the stand 201 comprises an under surface 209 and a plurality of strengthening ribs 211. The ribs 211 extend across the underside of the base in the region where the holder 231 connects to the base, to provide localised strength and rigidity to the base 203. Alternatively, the ribs could extend diagonally from one region where the holder 231 connects to the base, to an opposite corner of the base. A bottom edge 213 of the peripheral wall 207 is arranged to contact a support surface such as a floor, to support the support apparatus 200 on the floor. If the strengthening ribs 211 are of the same depth as the peripheral wall 207, the bottom edges of the strengthening ribs 211 will also contact the support surface. Other configurations of ribs may be provided.

The upper surface 205 of the base 203 surrounds a recess 215 for storage of one or more accessories of the breathing assistance apparatus 10. In the form shown, the recess 215 has a depth of a few millimetres. However, in different configurations, the upper surface 205 could be defined by one or more walls that extend(s) upwardly from a periphery of the recess 215, to provide a deeper recess. In other configurations, the recess 215 may not be provided, and the upper surface 205 of the base may be substantially planar.

In the form shown, the holder 231 comprises an upstanding arm component that has a first end 231a removably coupled to the base 201 at a first location on the base, a second end 231b removably coupled to the base at a second location on the base, the holder extending upwardly from the first end and second end so that the base and the holder form a general loop shape. Referring to FIGS. 4, 5, 23, 24, 30, and 31, the holder 231 has a first upstanding member 233 comprising the first end 231a, a second upstanding member 235 comprising the second end 231b, and an upper transverse connecting member 237 that extends between and connects upper ends of the first upstanding member 233 and the second upstanding member 235. The first upstanding member 233 extends upwardly from the first end 231a and upwardly from a first mount 351. The second upstanding member 235 extends upwardly from the second end 231b and upwardly from a support member 361. The transverse interconnecting member 237 is located higher than the first mount 351, the support member 361, and a second mount 371.

The first upstanding member 233, the second upstanding member 235, and the upper transverse connecting member 237 may be integrally formed. However, in the form shown, the first upstanding member 233, the second upstanding member 235, and the upper transverse connecting member 237 may be disassembled from each other to enable compact transport or storage of the support apparatus 200, while still providing the desired dimensions during use. The holder 231 comprises a first coupling arrangement 239 that removably couples the first upstanding member 233 to the upper transverse connecting member 237, and a second coupling arrangement 241 that removably couples the second upstanding member 235 to the upper transverse connecting member 237. This enables the holder 231 to be disassembled into three parts. In one configuration, the holder 231 may also disassemble from the base 203 so that the support apparatus 200 can disassemble into four components.

Referring to FIGS. 24-27, the first coupling arrangement 239 comprises a first connector 243 on the first upstanding member 233 that is removably engageable with a complementary second connector 245 on the upper transverse connecting member 237. The second coupling arrangement 241 comprises a third connector 247 on the second upstanding member 235 that is removably engageable with a complementary fourth connector 249 on the upper transverse connecting member 237. In the configuration shown, the second connector 245 and fourth connector 249 are male components, and the first connector 243 and third connector 247 are complementary female components. However, the male/female configuration of one or both of the coupling arrangements 239, 241 could be reversed. For example, one of the coupling arrangements 239, 241 could have the opposite male/female configuration to the other of the coupling arrangements 239, 341, so that the upper transverse connecting member 237 can only be mounted to the first and second upstanding members 233, 235 on one orientation.

The first connector 243 is engageable with the second connector 245 by pushing the first upstanding member 233 and the upper transverse connecting member 237 together, and the third connector 247 is engageable with the fourth connector 249 by pushing the second upstanding member 235 and the upper transverse connecting member 237 together; i.e. by pushing the upper transverse connecting member 237 downward toward the upstanding members 233, 235.

The coupling arrangements 239, 241 have retention features so that the first connector 243 cannot be disengaged from the second connector 245, and the third connector 247 cannot be disengaged from the fourth connector 249, solely by pulling the upper transverse connecting member 237 away from the first upstanding member 233 and the second upstanding member 235.

Figure 23:
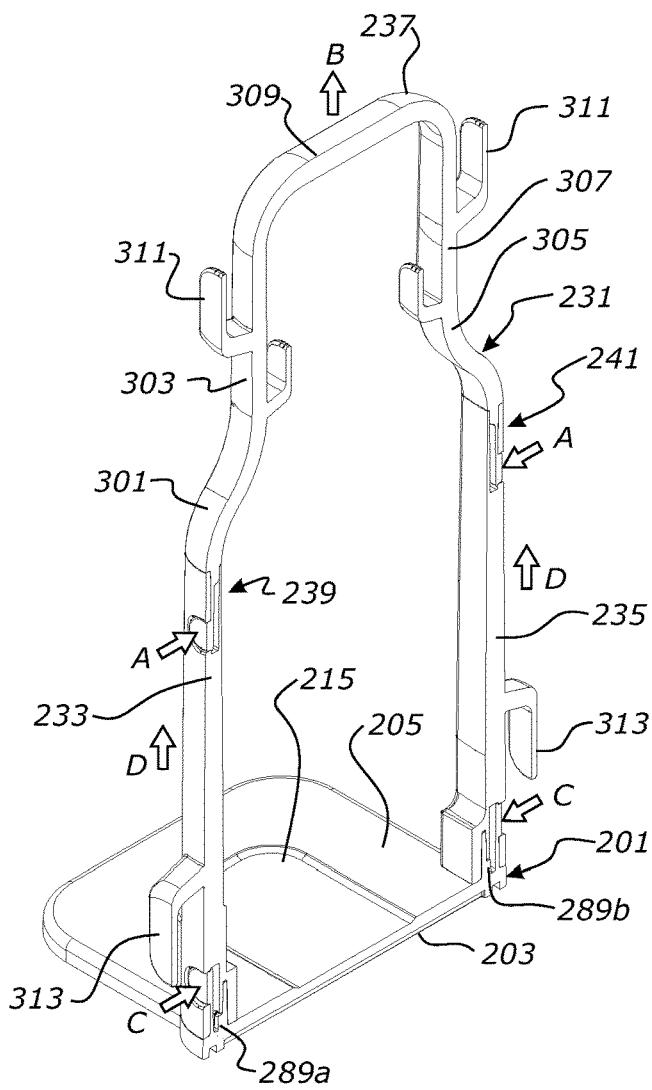
FIG. 23 is a right side/rear overhead perspective sectional view of the support apparatus, showing force directions to disassemble components of the support apparatus.
Figure 24:
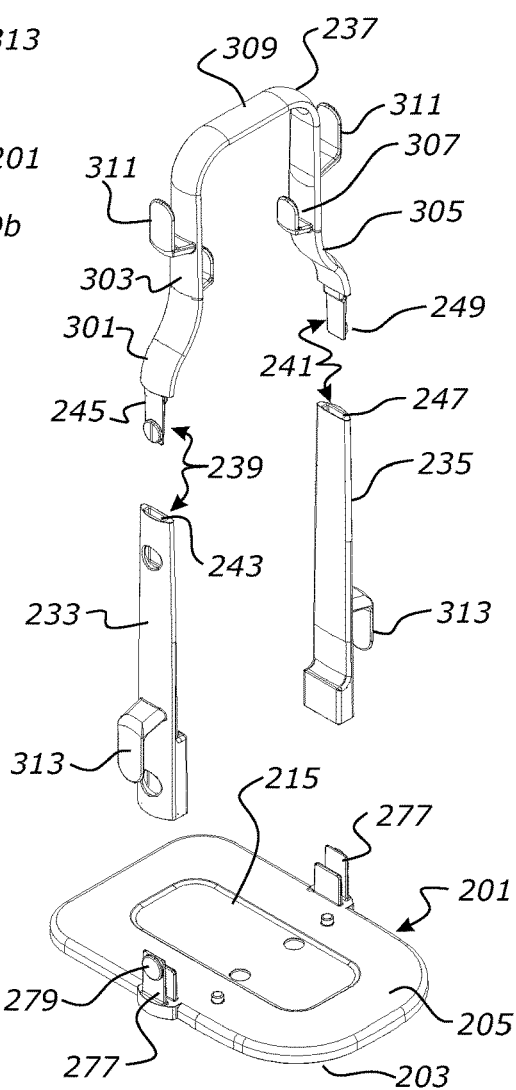
FIG. 24 is a left side/front overhead perspective view of the disassembled components of the support apparatus.
Figure 25:
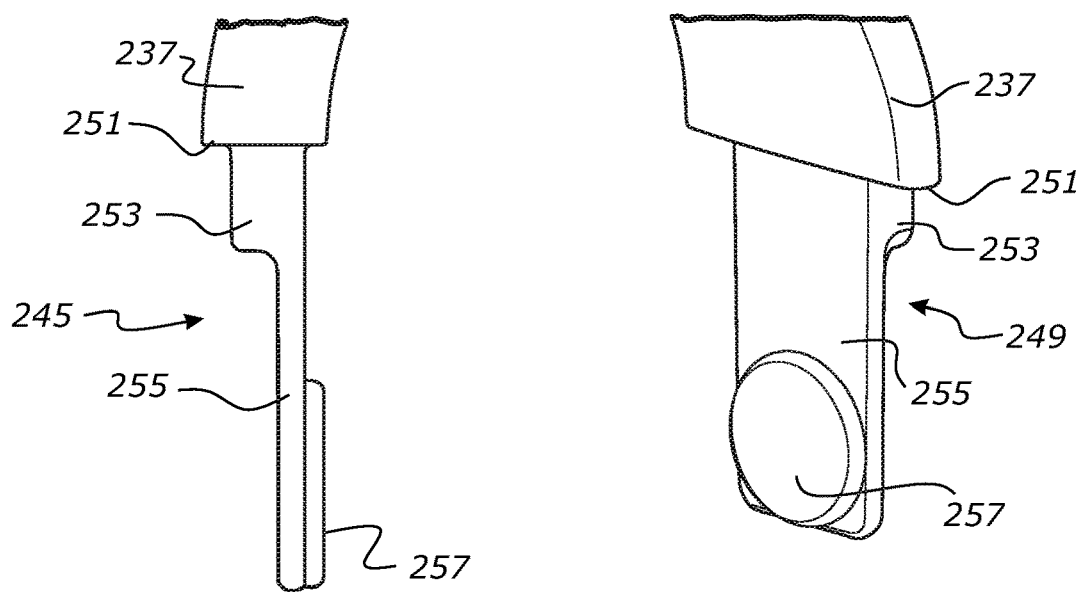
FIG. 25 is an external view of parts of first and second coupling arrangements of the support apparatus.
Figure 26:
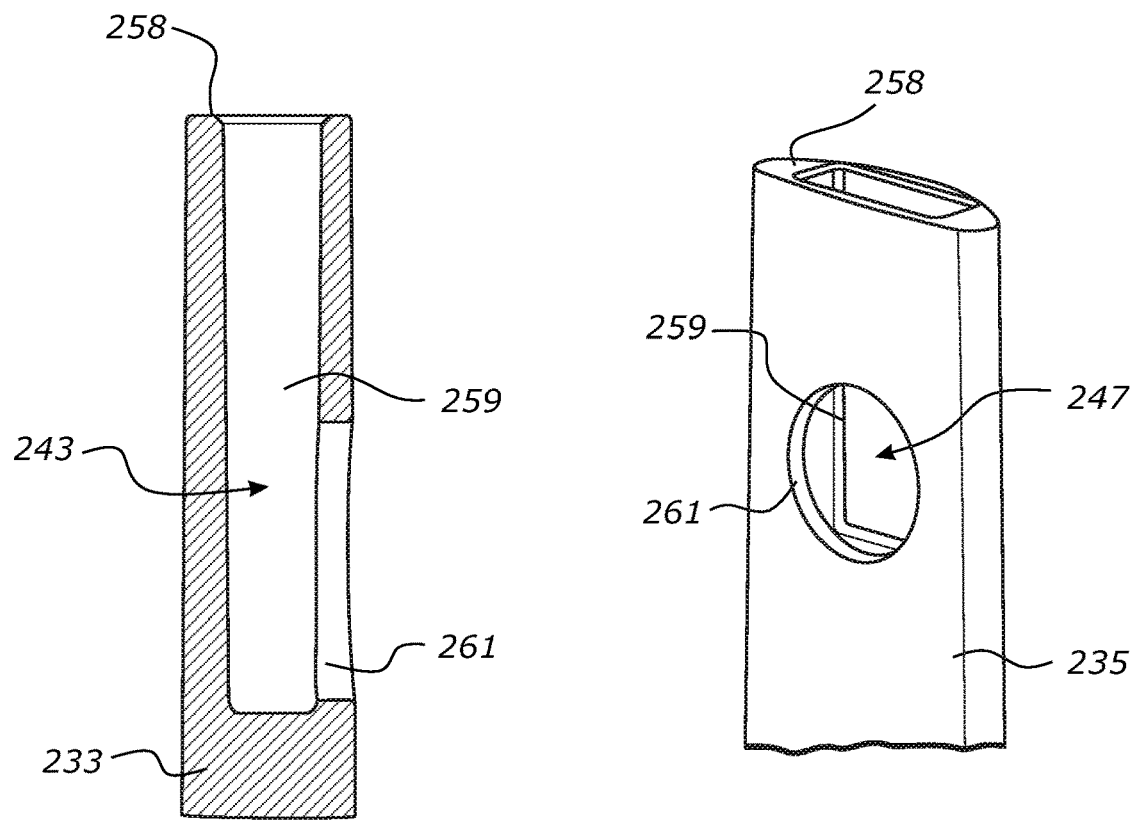
FIG. 26 is a sectional view (left side) and an external view (right side) of other parts of the first and second coupling arrangements.
Figure 27:
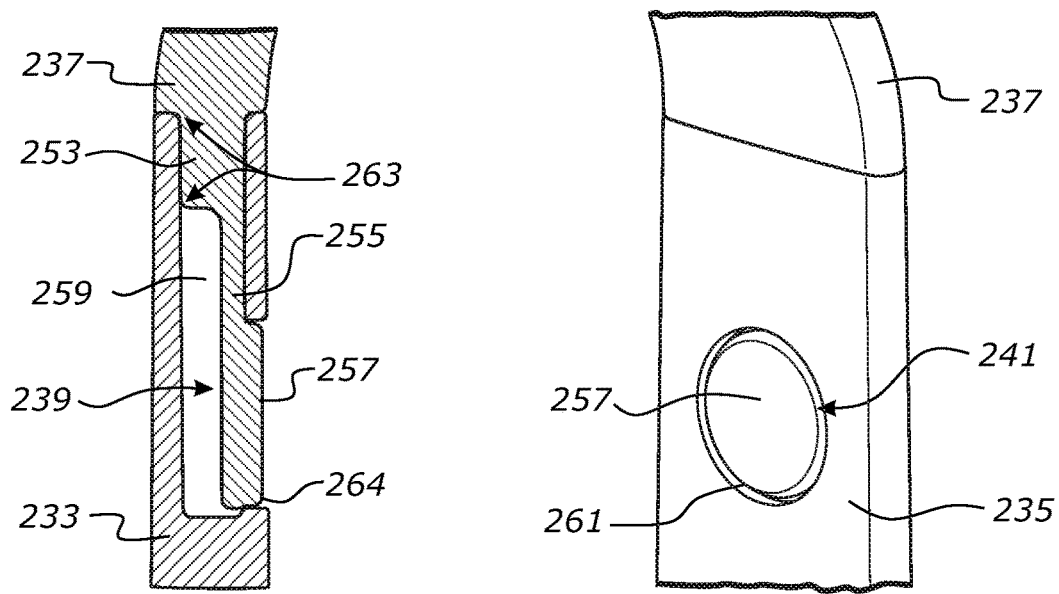
FIG. 27 is a sectional view (left side) and an external view (right side) of the assembled first and second coupling arrangements.
Figure 28:
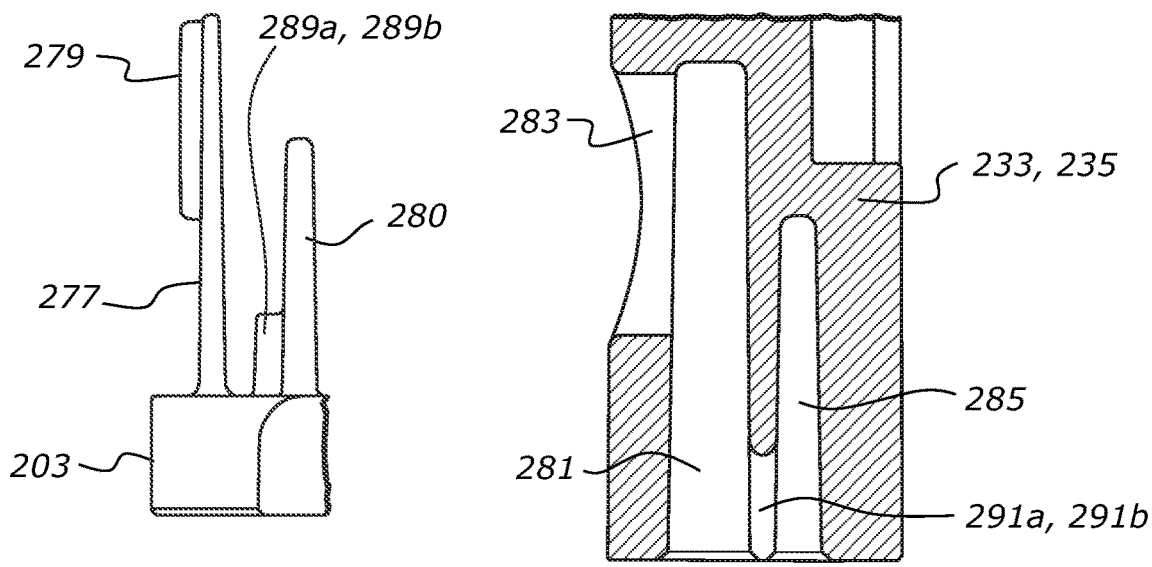
FIG. 28 is an external view (left side) and a sectional view (right side) of third and fourth coupling arrangements of the support apparatus.

Referring to FIG. 25, each of the second and fourth connectors 245, 249 comprises a flange 251 at its upper terminal end and internal connecting features beneath the flange 251. The connecting features comprise a locating feature 253 beneath the flange, and a resilient finger 255 beneath the locating feature 253. The enlarged locating feature 253 is provided at the base of the resilient finger 255. The resilient finger 255 extends downwardly in a longitudinal direction corresponding to a longitudinal direction of the respective upstanding member 233, 235. A release member in the form of a protrusion 257 is positioned at or adjacent a free lower end of the resilient finger 255. The protrusion extends from the resilient finger 255 in a direction that is transverse to the longitudinal direction of the resilient finger. In some configurations, the protrusion 257 may extend perpendicularly relative to the longitudinal direction of the resilient finger 255. In other configurations, the transverse direction is non-perpendicular to the longitudinal direction of the finger 255. As shown in FIGS. 25 to 27, the protrusions 257 may extend inwardly from the fingers towards a centre of the support apparatus 200. However, one or both of the protrusions could, instead, extend outwardly, in a forward direction, or in a rearward direction relative to the finger. For example, FIGS. 23 and 24 show the protrusions extending outwardly from the fingers.

Referring to FIGS. 26 and 27, the first and third connectors 243, 247 each comprise an upper terminal shoulder 258 at upper ends of the first and second upstanding members 233, 235. A recess 259 extends into the upstanding members 233, 235 from the shoulders 258. A transverse aperture 261 extends from the recess 259 through a wall of each upstanding member 233, 235. The transverse aperture 261 is positioned at or adjacent a lower end of the recess 259. The aperture 261 has a shape that is complementary to the shape of the protrusion 257.

FIG. 27 shows the connectors in an assembled configuration. During assembly, the tip of the resilient finger 255 is inserted into the recess 259. During insertion, the lower end of the locating feature 253 may require alignment with the recess 259. This can be aided by rounded lead in features 263 on the terminal ends of the locating feature 253 and the walls that define the recess. The outer surface of the locating feature 253 is complementary to the inner surface of the recess 259, such that mating the two features together results in axial alignment in the rest of the coupling arrangements and thereby the upstanding members. At this point the protrusion 257 on the resilient finger will contact the inner surface of the recess 259, causing the resilient finger to bend away from the side with the protrusion 257.

While the contact between the locating feature 253 and the recess 259 provides alignment in two directions, alignment in the third direction (i.e. insertion depth) can be provided by the contact between the flange 251 on the male connector and the shoulder 258 on the terminal end of the female connector. A user will push the two connectors together until these two features abut one another. At this point the protrusion 257 on the resilient finger 255 of the male connector will be aligned with the aperture 261 of the female connector. The resilient finger will then bend back into its original position, causing the protrusion 257 to engage with the aperture 261. A rounded lead in feature 264 around the edge of the protrusion 257 can aid in aligning the protrusion with the aperture 261. The protrusion 257 may have a slightly smaller diameter than the aperture 261 to accommodate manufacturing tolerances and to aid in connection. The finger 255 can be biased in the direction of the protrusion 257 to encourage engagement of the protrusion in the aperture 261.

Once the protrusions 257 are engaged with the apertures 261, attempting to pull the upper transverse connecting member 237 apart from the upstanding members 233, 235 will cause the edge of the protrusions 257 to catch on the edge of the apertures 261, thereby preventing disengagement of the coupling arrangements. This allows to support apparatus 200 and a coupled breathing assistance apparatus 10, 10' to be lifted and carried by the upper transverse connecting member 237 without the various components of the support apparatus becoming disengaged from each other. In order to disassemble the coupling arrangements 239, 241 of the support apparatus 200, the user must press on the exposed surface of the protrusions 257 in order to flex the resilient fingers to move the protrusions 257 in a second direction (arrow A in FIG. 23) that is transverse to the coupling direction of the connectors, into the interior recess 259 to clear the edge of the aperture 261 and disengage the protrusions 257 from the apertures 261, while simultaneously applying an upward force (arrow B in FIG. 23) to pull the components apart.

The release member and engagement edge may differ from the protrusion 257 and apertures 261 shown. For example, the protrusion may comprise a differently-shaped member that engages against a shoulder of the other connector.

As shown, the first connector 243 may be the same as the third connector 247, and the second connector 245 may be the same as the fourth connector 249, so that the first connector 243 can engage with the fourth connector 249 and so that the third connector 247 can engage with the second connector 245, so that the upper transverse connecting member 237 can couple to the upstanding members 233, 235 in two orientations. This configuration is suitable if the upper transverse connecting member 237 is symmetrical; i.e. it has the same shape and features on each side. Alternatively, the first connector 243 may be different from the third connector 247, and the second connector 245 may be different from the fourth connector 249, so that the first connector 243 cannot engage with the fourth connector 249 and so that the second connector 245 cannot engage with the third connector 247, so that that the upper transverse connecting member 237 can only couple to the upstanding members 233, 235 in a single orientation. This configuration is suitable if the features on the holder are asymmetrical. The shape and/or position of the connectors on one side of the support apparatus may differ from the shape and/or position of the connectors on the other side of the support apparatus. As one example, the protrusions 257 and apertures 261 on one side of the apparatus may have a different shape from those on the other side of the apparatus.

Instead of having two coupling arrangements 239, 241, the holder 231 may have a single coupling arrangement so that the holder 231 can be disassembled into two parts. For example, the single coupling arrangement may be positioned in the middle of the upper transverse connecting member 237.

The stand 201 is configured to support the holder 231 in an upstanding configuration from the base. The holder 231 may be permanently mounted to the base or integrally formed with the base, or may be removably coupled with the base.

In a removable configuration, referring to FIGS. 19-24 and 28, a third coupling arrangement 265 removably couples the first end 231a of the holder to the base 203 and a fourth coupling arrangement 267 removably couples the second end 231b of the holder to the base 203.

The third coupling arrangement 265 comprises a fifth connector 269 on the base that is removably engageable with a sixth connector 271 on the holder, and the fourth coupling arrangement 267 comprises a seventh connector 273 on the base that is removably engageable with a complementary eighth connector 275 on the arm. In the configuration shown, the fifth connector 269 and seventh connector 273 are male components, and the sixth connector 271 and eighth connector 275 are complementary female components. However, the male/female configuration of one or both of the coupling arrangements 265, 267 could be reversed.

The fifth connector 269 is engageable with the sixth connector 271, and the seventh connector 273 is engageable with the eighth connector 275, by pushing the holder and the base together; i.e. a downward movement of the first and second upstanding members 233, 235 of the holder relative to the base 203.

The coupling arrangements 265, 267 have retention features so that the fifth connector 269 cannot be disengaged from the sixth connector 271, and the seventh connector 273 cannot be disengaged from the eighth connector 275, solely by pulling the first and second upstanding members 233, 235 of the holder 231 away from the base 203.

The features, functioning, and options for the third and fourth coupling arrangements 265, 267 are similar to the first and second coupling arrangements 239, 241, unless described differently below. Referring to FIGS. 19-24 and 28, the male connectors 269, 273 each comprise an upstanding resilient finger 277 with a transversely extending protrusion 279 at or toward the free end of the finger. The fingers 277 are configured to insert into recesses 281 in the lower ends of the first and second upstanding members 233, 235. The protrusions 279 are configured to insert into apertures 283 that extend through walls from the recesses 281.

The male connectors 269, 273 also comprise locating features 280. These locating features 280 are separate upstanding tab members that are configured to insert into separate recesses 285 in the upstanding members 233, 235.

The locating features 280 may be located at a specified distance apart across the base 203, such the distance matches the outer dimension of the housing 100 of the first configuration breathing assistance apparatus 10. This allows the disassembled base 203 to be packed with the breathing assistance apparatus 10, with a tight fit of the breathing assistance apparatus between the two locating features 280.

If the holder 231 is symmetrical (i.e. it has the same shape and features on each side) or the base 203 is symmetrical so that the shape of a forward part of the base is the same as the shape of a rear part of the base 203, the coupling arrangements 265, 267 may be configured so that the fifth connector 269 is the same as the seventh connector 273, and the sixth connector 271 is the same as the eighth connector 275, so that the fifth connector 269 can engage with the eighth connector 275 and so that the seventh connector 273 can engage with the sixth connector 271, and so that the holder 231 can be mounted in two orientations relative to the base 203. However, in the form shown (and as described below), the holder 231 is asymmetrical and the base 203 is asymmetrical and has a footprint to substantially match the footprint of the breathing assistance apparatuses 10, 10'. The holder 231 has a first mount 351 on one side of the holder for coupling to and supporting the first configuration breathing assistance apparatus 10. Therefore, the coupling arrangements 265, 267 are advantageously configured so that the holder 231 can only be mounted to the base 203 in one orientation. In the form shown, the fifth connector 269 is different from the seventh connector 273 and the sixth connector 271 is different from the eighth connector 275, so that the fifth connector 269 cannot engage with the eighth connector 275 and so that the seventh connector 273 cannot engage with the sixth connector 271. This prevents the holder 231 from being assembled incorrectly relative to the base 203, which in turn ensures the mount 351 is on the correct side of the base. The mount being on the correct side of the base results in the breathing assistance apparatus 10 being correctly aligned with the base 203 when the breathing assistance apparatus 10 is releasably coupled to the support apparatus 200.

In the form shown, each male connector 269, 273 comprises a rib 289a, 289b that extends transversely, and in one configuration perpendicularly, from the locating feature 280. The ribs 289a, 289b may extend towards the resilient fingers 277 or away from the resilient fingers 277. Similarly, each female connector 271, 275 has a slot 291a, 291b that passes through the wall that separates the two apertures 281, 285. The ribs 289a, 289b and slots 291a, 291b are configured to be complementary in shape, such that the two features engage when the upstanding members 233, 235 are connected to the base 203.

The position of the ribs 289a, 289b are different on each male connector, and the position of the slots 291a, 291b are different on each female connector, such that each upstanding member 233, 235 can only connect to a connector on one specific side of the base 203. In the configuration shown, the two male connectors (as well as the two female connectors) are mirror images of each other, such that the position of the rib/slot is reversed on the two sides. The ribs and slots are closer to a front CF of the coupling arrangement than to a rear CR of the coupling arrangement. Alternatively, the ribs and slots may be closer to a rear of the coupling arrangement than to a front of the coupling arrangement. Different configurations can be used.

Figure 19:
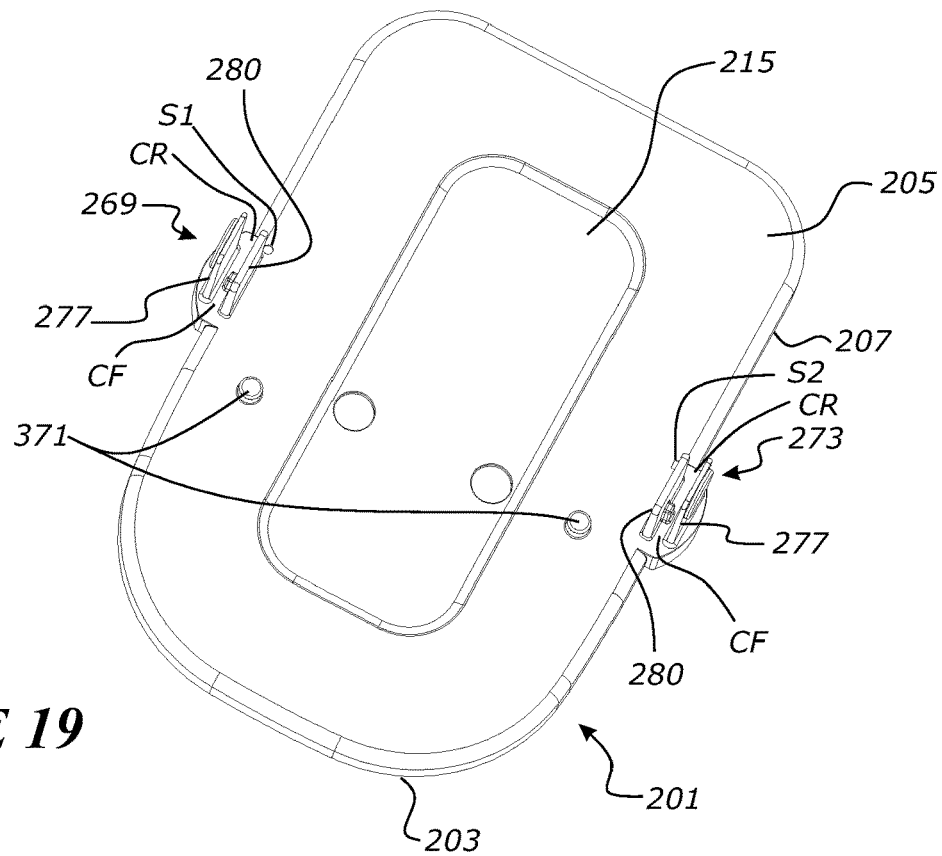
FIG. 19 is a right side/front overhead perspective view of a base of the support apparatus.
Figure 20:
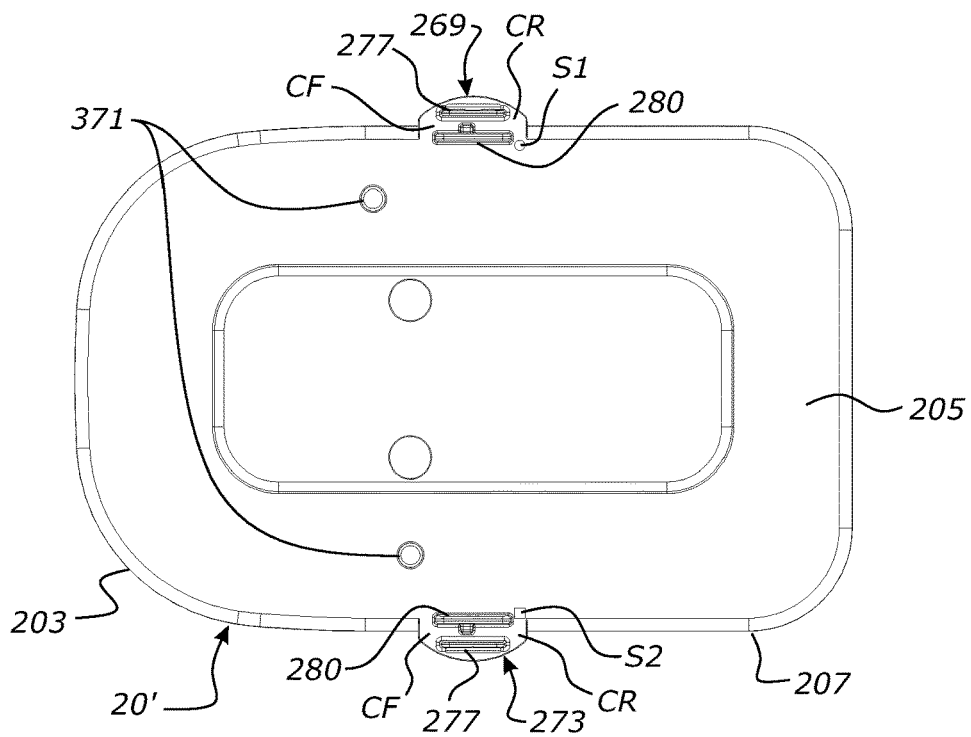
FIG. 20 is an overhead view of the base of the support apparatus.
Figure 21:
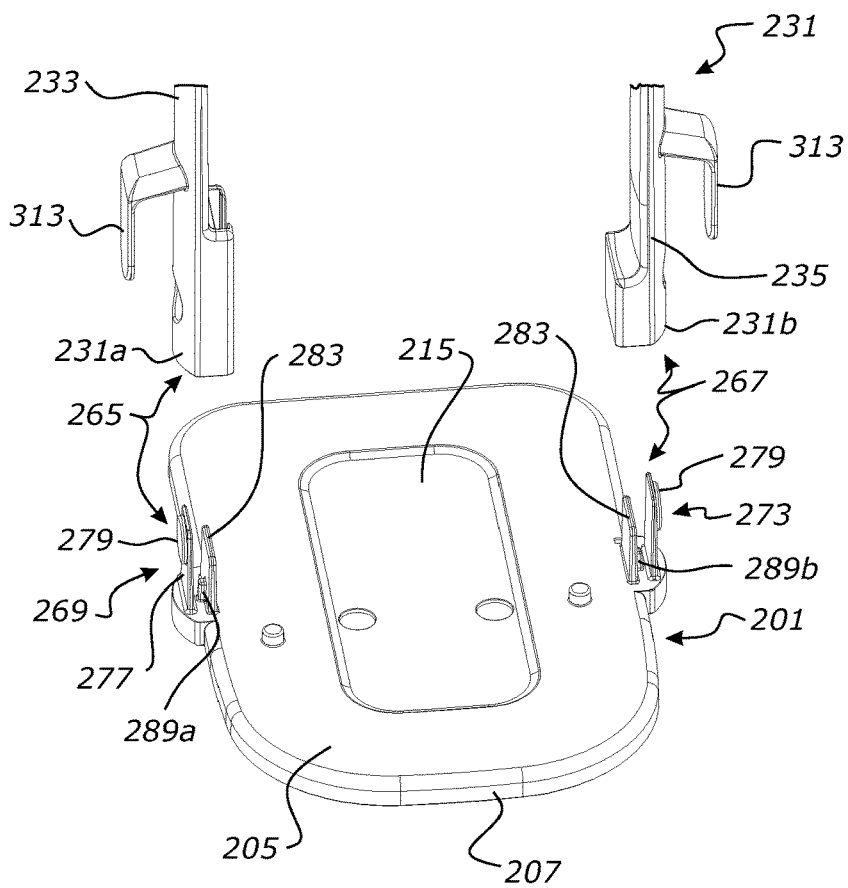
FIG. 21 is a left side/front overhead perspective exploded view of the base of the support apparatus and the lower ends of the arm of the support apparatus.
Figure 22:
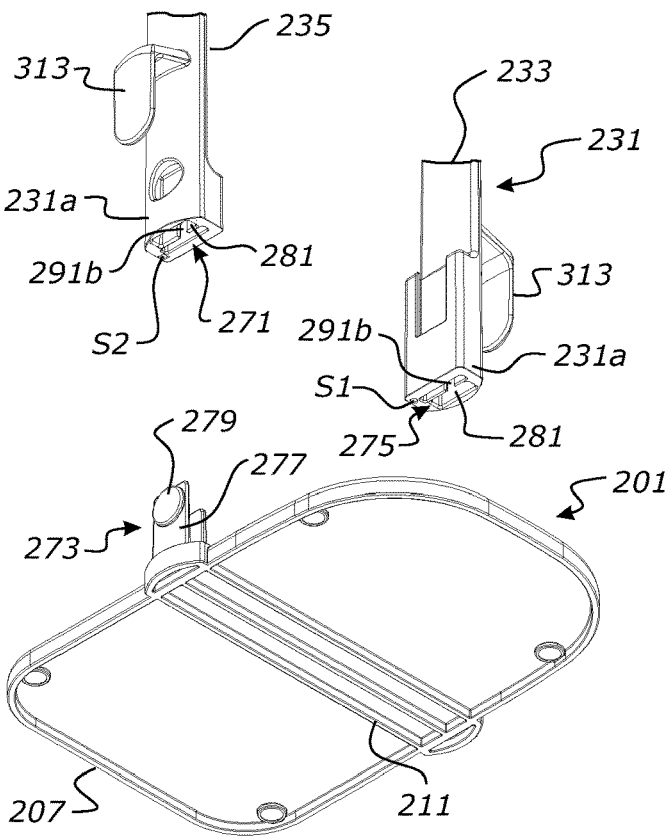
FIG. 22 is a left side/front underside perspective exploded view of the base of the support apparatus and the lower ends of the arm of the support apparatus.

The base 203 and upstanding members 233, 235 may also have indicators that indicate to a user which upstanding member 233, 235 connects to which side of the base 203. The indicator could take the form of a shape or symbol S1, S2 on the upstanding member and a similar or identical shape or symbol S1, S2 on the corresponding side of the base. Exemplary shapes or symbols are shown in FIGS. 19, 20, and 22.

To remove the upstanding members 233, 235 from the base 203, a user must first press on the exposed surface of the protrusions 279 in order to flex the resilient fingers to disengage the protrusions 279 from the apertures 283 (arrows C in FIG. 23) and move them into the interior recesses 281 to clear the edges of the apertures 283, while simultaneously applying an upward force (arrow D in FIG. 23) to pull the components apart.

The connectors of the first and second coupling arrangements 239, 241 cannot be engaged with the connectors of the third and fourth coupling arrangements 265, 267, so that the upper transverse connector component 237 cannot inadvertently be coupled directly to the base 203. The second and fourth connectors 245, 249 cannot connect to the fifth and seventh connectors 269, 273. This can, for example, be achieved by having the first and second coupling arrangements 239, 241 different to the third and fourth coupling arrangements 265,267, and/or by having the second, fourth, fifth, and seventh connectors all male or all female.

Figure 8:
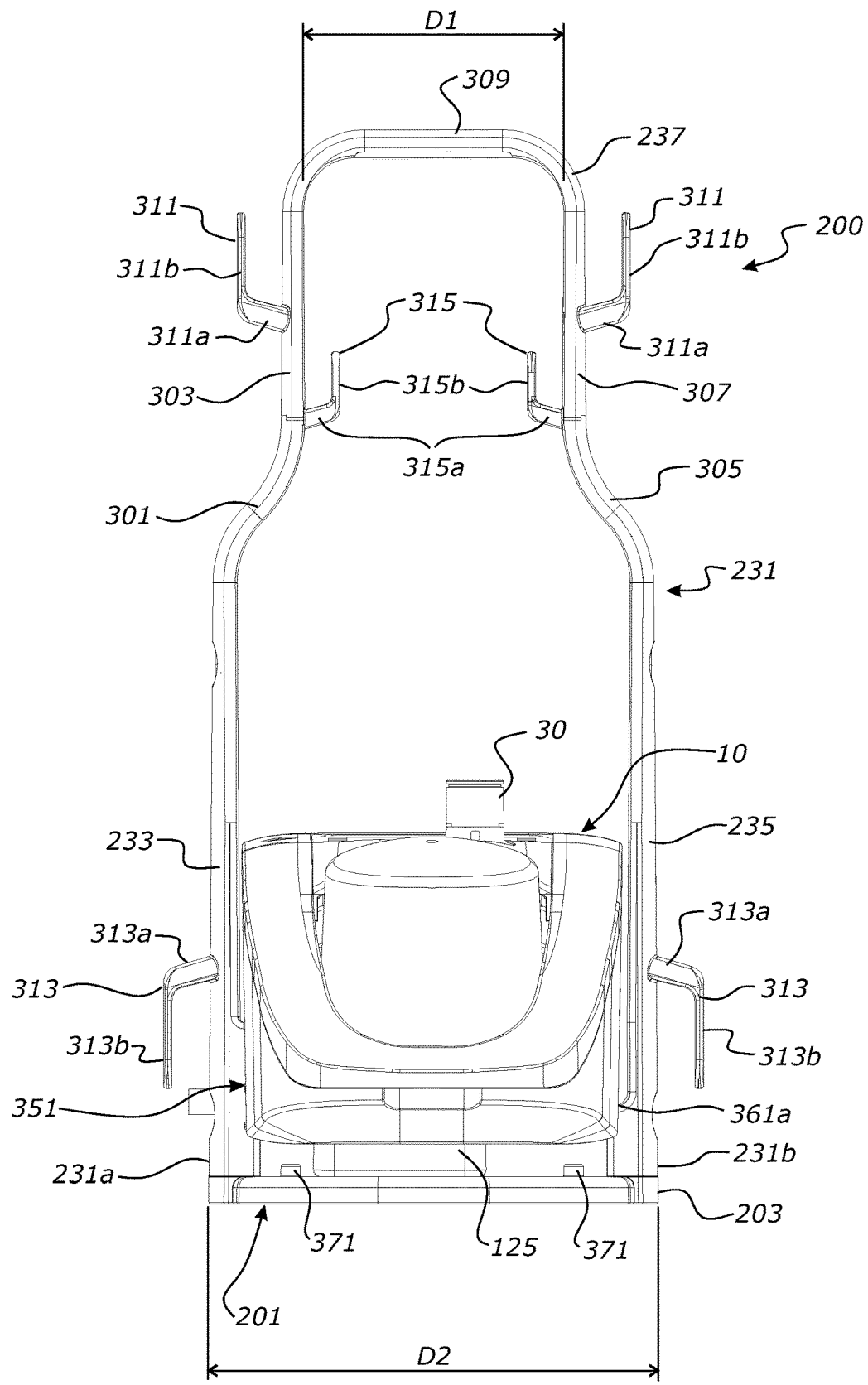
FIG. 8 is a front view of the support apparatus with a first configuration breathing assistance apparatus releasably coupled with the first mount of the support apparatus, with part of the breathing assistance apparatus not shown.
Figure 9:
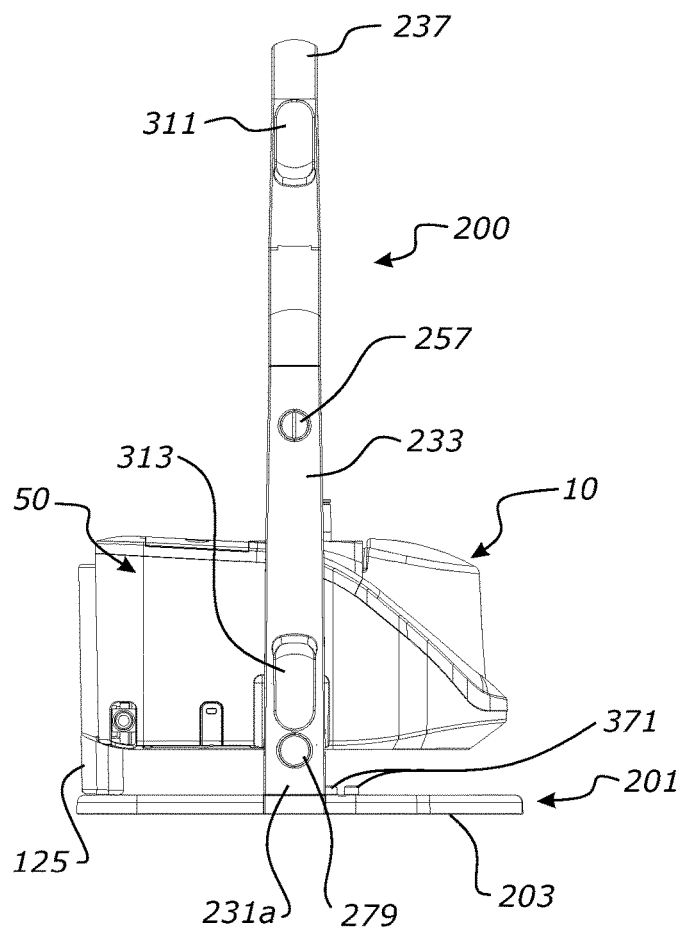
FIG. 9 is a left side view corresponding to FIG. 8.
Figure 10:
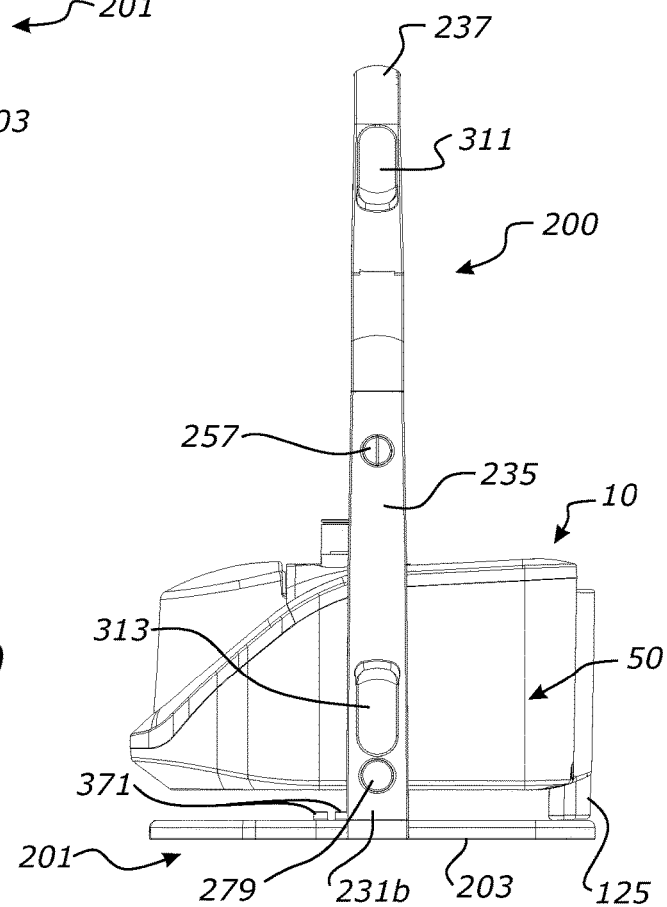
FIG. 10 is a right side view corresponding to FIG. 8.
Figure 11:
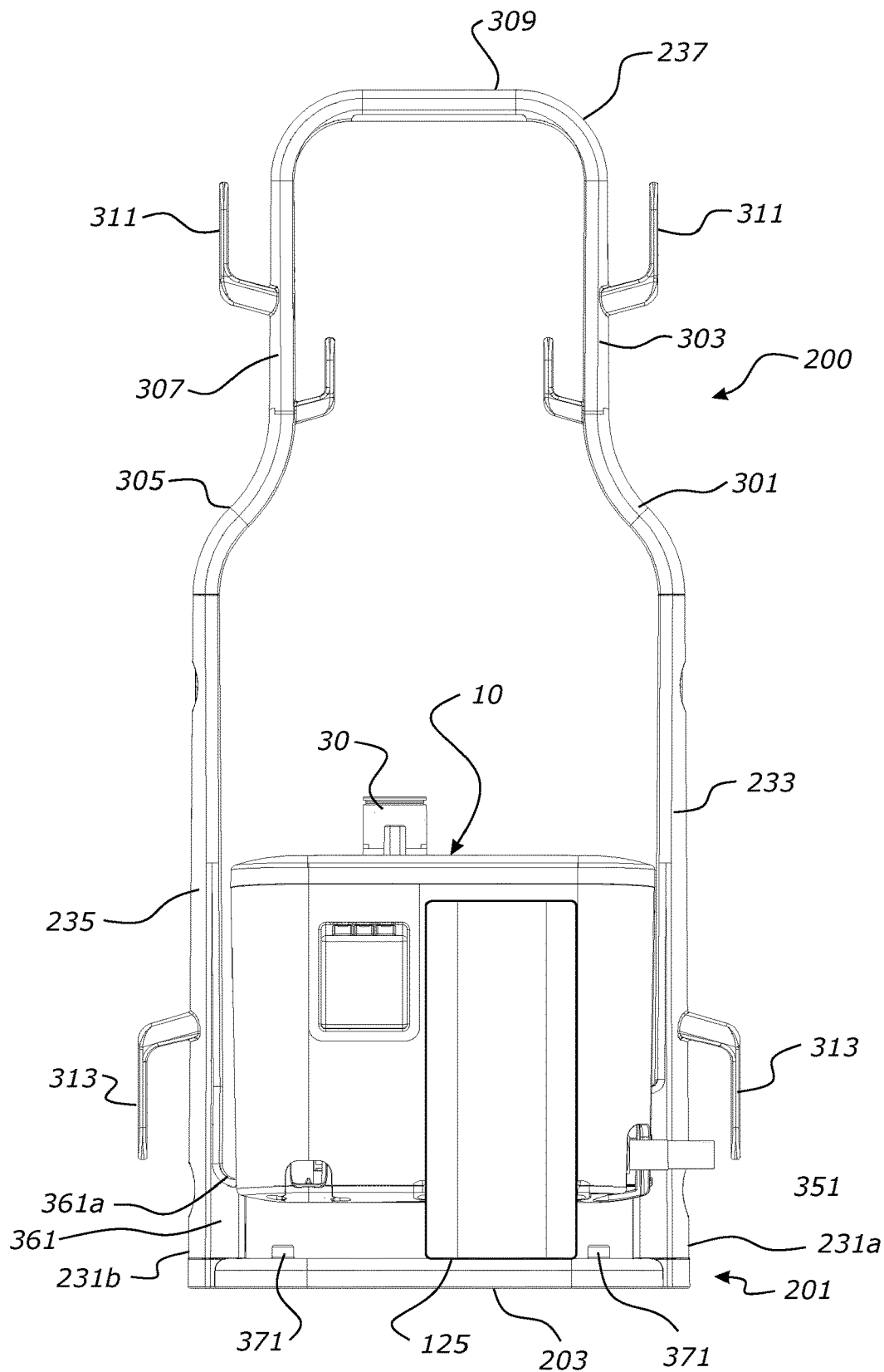
FIG. 11 is a rear view corresponding to FIG. 8.
Figure 12:
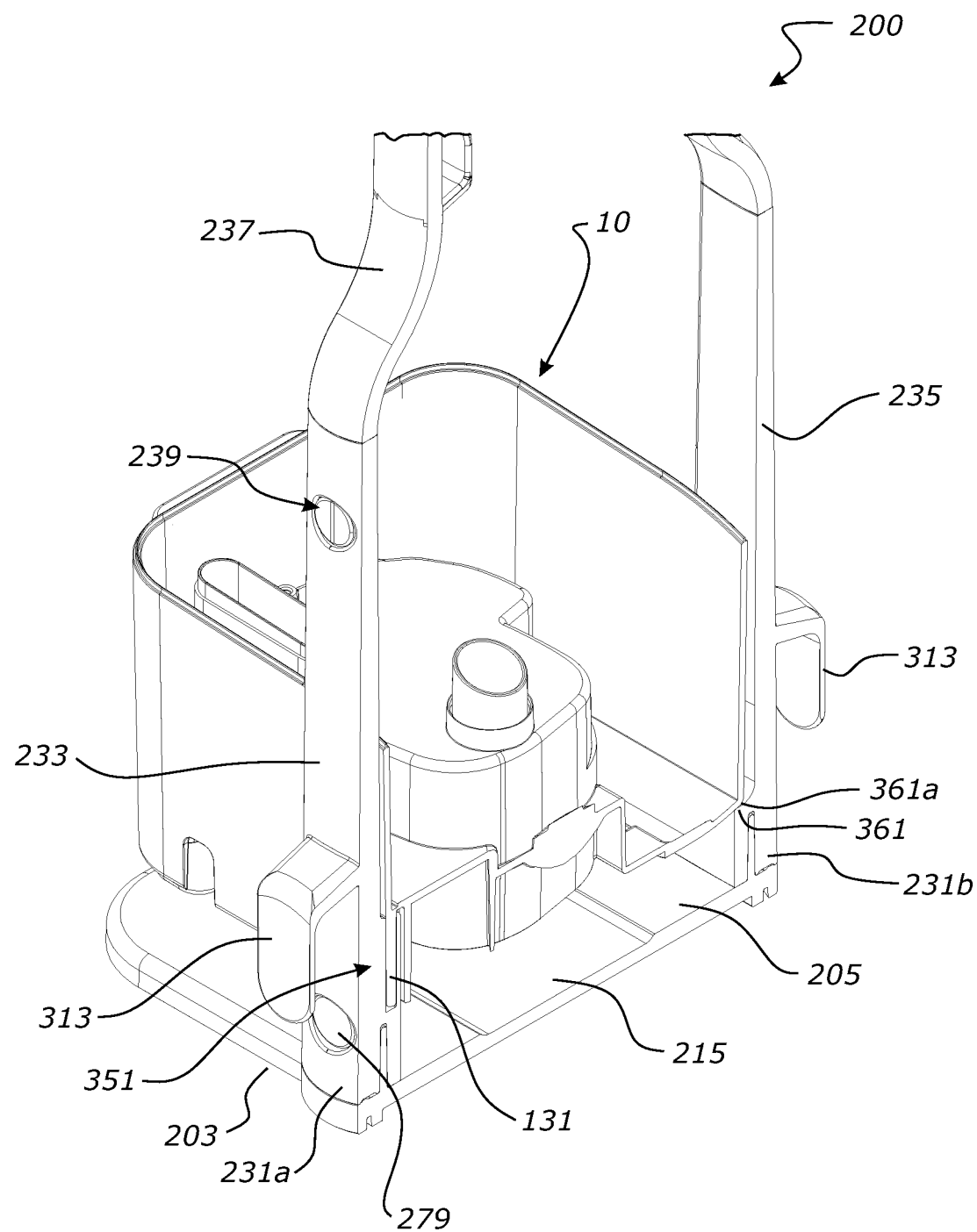
FIG. 12 is a left/front overhead perspective sectional view of the support apparatus releasably coupled with the first configuration breathing assistance apparatus, showing the engagement of the tongue of the breathing assistance apparatus with the first mount of the support apparatus.

Referring to FIG. 8, a first side of the upstanding holder 231 comprises the first upstanding member 233 at or adjacent the first side and which forms a lower upstanding member extending upwardly from the first end 231a of the holder, an intermediate connecting portion 301 at an upper end of the lower upstanding member 233, and an upper upstanding member 303 extending upwardly from the intermediate connecting portion 301. The upper upstanding member 303 is offset inwardly from the lower upstanding member 233. An opposite second side of the holder 231 comprises the second upstanding member 235 at or adjacent the second side and which forms a lower upstanding member extending upwardly from the second end 231b of the holder, an intermediate connecting portion 305 at an upper end of the lower upstanding member 235, and an upper upstanding member 307 extending upwardly from the intermediate connecting portion 205. The upper upstanding member 307 is offset inwardly from the lower upstanding member 235. Therefore, the upper upstanding members 303, 307 are spaced closer together than the lower upstanding members 233,235.

Because the holder 231 connects to the base 203 at two spaced apart locations, the rigidity of the holder is improved, thereby reducing the amount the holder 231 will bend when the holder is holding accessories of the breathing assistance apparatus 10, 10'. Having the holder extend from two separate locations on the base increases the space that is available for positioning mechanical features 311, 313, 315 for holding the accessories. The loop shape provided by the base and the holder provides better rigidity than if the lower upstanding members 233, 235 had free, unsupported upper ends.

In the form shown, the upper upstanding members 303, 307 are substantially parallel to the respective lower upstanding members 233, 235 along substantially their entire lengths.

In the form shown, the upper upstanding members 303, 307 and the lower upstanding members 233, 235 extend substantially vertically from the base 203, when the base is resting on a support surface.

The upper upstanding members 303, 307 and the lower upstanding members 233, 235 may be substantially straight to provide optimal stability and load support, or may have a different shape.

The intermediate connecting portions 301, 305 advantageously comprise curved sections to minimise stresses in the intermediate connecting portions.

In the form shown, the intermediate connecting portions 301, 305 and the upper upstanding members 303, 307 are provided as part of the upper transverse connecting member. In alternative configurations, the intermediate connecting portions 301, 305 and/or the upper upstanding members 303, 307 could be integrally formed with the lower upstanding members 233, 235.

The upper transverse connecting member 237 comprises an upper transverse member 309 that extends between and connects the upper ends of the upper upstanding members 303, 307. The upper transverse member 309 forms a handle that is configured to enable the support apparatus 200 and a releasably coupled breathing assistance apparatus 10, 10' to be lifted and carried by a user. In some configurations, the holder 231 may comprise a single upstanding member 233 with the handle 309 extending from that component. However, having the handle 309 connecting to two upstanding members divides the lifting force from the handle 309 evenly between the sides of the base 203. With a single upstanding member, the force would be applied to only one side of the base, introducing a large moment in the single upstanding member.

As shown in FIG. 8, the handle 309 has a length D1 that is shorter than the transverse outer dimension D2 of the base. The handle 309 is substantially parallel to the underside 209 of the base 203.

A centre of the handle 309 is aligned with a centre of mass of the support apparatus 200, and in the form shown is positioned higher than the centre of mass of the support apparatus 200. The support apparatus is configured so that a centre of mass of a releasably coupled breathing assistance apparatus 10, 10' is substantially aligned or coincident with the centre of mass of the support apparatus. As a result, the weight of the support apparatus 200 and the breathing assistance apparatus 10, 10' when lifted will be applied directly below the handle 309, such that the support apparatus remains level when lifted by the handle 309. This enables the support apparatus and breathing assistance apparatus to be easily carried with one hand.

The holder 231 comprises at least one mechanical feature for holding and supporting an accessory of a breathing assistance apparatus 10, 10', such as a conduit 16, 16' and/or patient interface 17 and/or liquid bag 101 and/or liquid container 600 and/or tube(s) 101a from the liquid bag or liquid container and/or power cord 103. The at least one mechanical feature has a shape that is complementary to the shape of the accessory. The accessories can be supported in any desired arrangement from the mechanical features 311, 313, 315 of the support apparatus, if the mechanical features do not have a configuration that is specific to a particular accessory.

In the form shown, the left side of the holder 231 has a first holder portion on an outer left side of the holder 231. The first holder portion comprises a first mechanical feature 311 on the upper upstanding member 303 and a second opposed mechanical feature 313 on the lower upstanding member 233. The first mechanical feature 311 extends in a first, upward, direction from the upper upstanding member. The second mechanical feature 313 extends in a second, downward, direction from the lower upstanding member 233. The second direction is substantially opposite to the first direction. The first mechanical feature 311 extends upwardly so that an accessory can be hung from the first mechanical feature without using the second mechanical feature 313.

Figure 13:
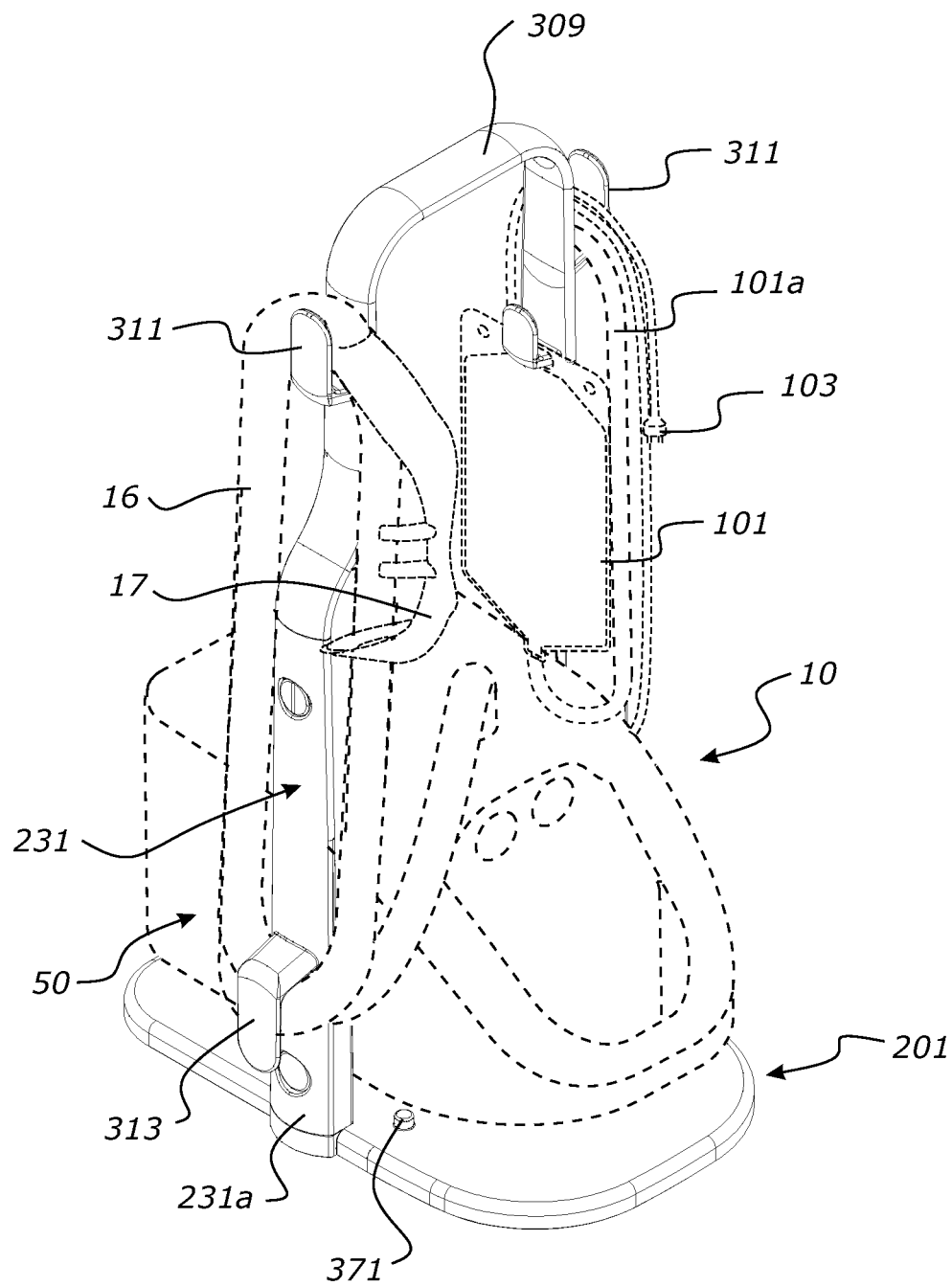
FIG. 13 is a right side/front perspective view of the first configuration breathing assistance apparatus mounted to the support apparatus, with an accessory of the breathing assistance apparatus wrapped around and supported by mechanical features.

The opposed mechanical features 311, 313 are configured so that an accessory can be wrapped around the mechanical features in loops, as shown schematically in FIG. 13. This provides a tension force in the accessory that helps prevent the accessory from coming loose, particularly when the support apparatus and accessory are being carried.

In an alternative configuration, the first and second mechanical features may be spaced horizontally and extend in a forward and rearward direction of the apparatus. However, the configuration shown in the figures provides a more compact arrangement on the holder 231.

The first and second mechanical features 311, 313 are configured as outer mechanical features, so that when the support apparatus is assembled the first and second mechanical features 311, 313 are located on the outer side of the loop formed by the holder 231 and the base 203. This configuration leaves the mechanical features 311, 313 unobstructed, which allows an accessory such as a conduit or power cord to be more easily wrapped around the opposing mechanical features.

In the configuration shown, the right side of the holder 231 has a second holder portion on an outer right side of the holder 231. The second holder portion comprises first and second mechanical features 311, 313, and the features and functionality of those features are as described above for the first holder portion.

Figure 42:
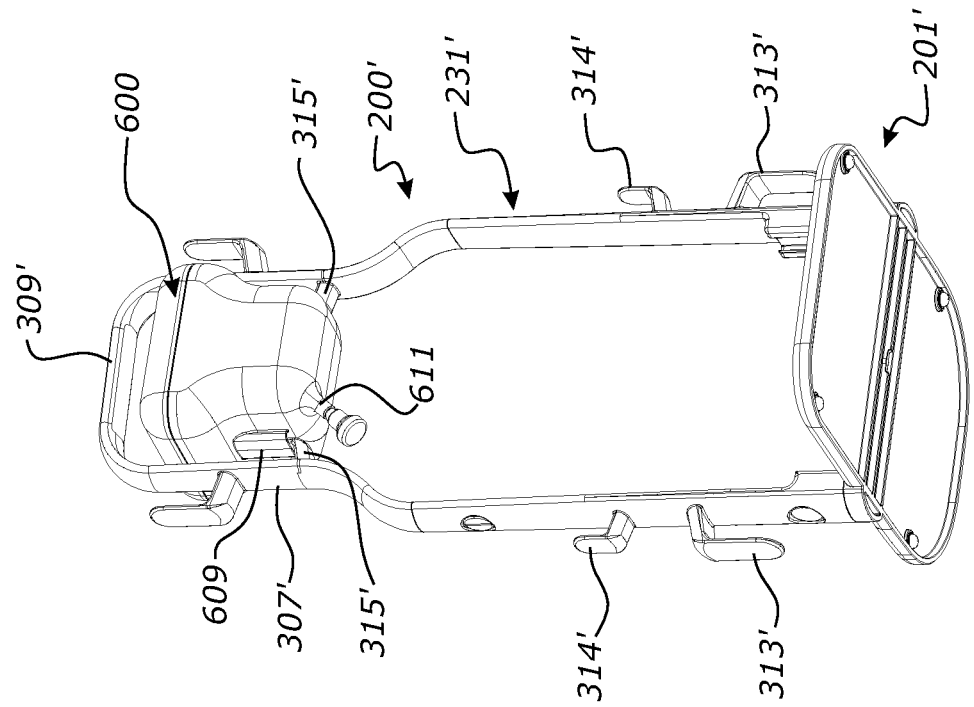
FIG. 42 is a view similar to FIG. 40 but with a liquid container coupled to the support apparatus.
Figure 41:
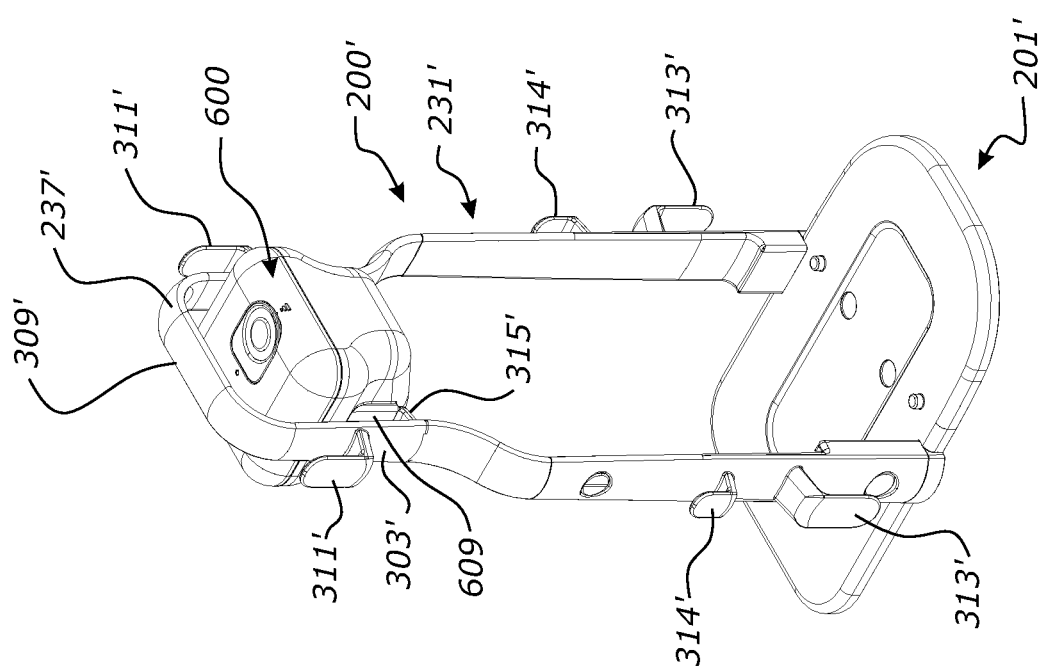
FIG. 41 is a view similar to FIG. 39 but with a liquid container coupled to the support apparatus.

Additional inner mechanical features 315 may be positioned on the opposite side of one or both of the upstanding members from the aforementioned mechanical features. When assembled, the inner mechanical features 315 sit on the inner side of the loop formed by the holder 231 and the base 203. This location makes the inner mechanical features suitable for supporting accessories that will be less frequently attached and detached. For example, as shown in FIG. 13, a liquid bag 101 could be hung from an inner mechanical feature 315, leaving the outer mechanical features 311, 313 free and unobstructed for attaching another accessory such as a conduit 16, 16', patient interface 17, tube(s) 101a from the liquid bag 101, and/or power cord 103. As another example, as shown in FIGS. 41 and 42, a liquid container 600 could be coupled to one or more inner mechanical features 315, leaving the outer mechanical features 311, 313 free and unobstructed for attaching another accessory such as a conduit 16, 16', patient interface 17, tube(s) from the liquid container 600, and/or power cord 103.

Referring to FIG. 8, in the form shown, each mechanical feature comprises a base portion 311a, 313a, 315a that extends from the respective upstanding member 303, 307, 233, 235, and a distal support portion 311b, 313b, 315b that is configured to support the accessory between the distal support portion and the respective upstanding member. The distal support portion 311b, 313b, 315b may be substantially parallel to the respective upstanding member 303, 307, 233, 235.

The distal support portion 311b, 313b, 315b is advantageously sufficiently long for each mechanical feature to accommodate a plurality of breathing assistance apparatus accessories. Alternatively, when the accessory is a conduit or power cord, the long distal support portion can allow the mechanical feature to accommodate multiple loops of the same accessory. This is beneficial in terms of making the system more compact and tidy. By way of example, the length of the distal support portion 311b, 313b, 315b may be at least 1.5 times the width of the slot formed between the distal support portion and the respective upstanding member 233, 235, 303, 307.

The first mechanical features 311 on the upper upstanding members 303, 307 are preferably positioned substantially directly above the lower upstanding members 233, 235. This means that the weight of the supported accessory does not produce a large moment in the lower upstanding members 233, 235, which is particularly useful for heavier accessories, such as a liquid bag.

When the support apparatus 200 is lifted by the handle 309, a tensile force is applied through the holder 231. This force is proportional to the weight of the system that is being supported. Any sections of the holder 231 that are above the mechanical features will also be supporting the weight of any accessories that are attached.

By placing the coupling arrangements 239, 241 below the mechanical features 311, 315, the coupling arrangements 239, 241 do not need to support tensile force related to the weight of the accessories that are supported by the mechanical features 311, 315. This is beneficial, because the narrow cross section of the resilient fingers 255, as well as the small contact area between the protrusions 257 and the apertures 261 will mean that the coupling arrangements 239, 241 would experience greater stress than a solid section of the holder 231 would under the same force.

In an alternative configuration of the holder 231, the first and second coupling arrangements 239, 241 could be positioned above the intermediate connecting portions 301, 305; however, that would mean the weight on the first mechanical features 311 will be offset from the coupling arrangements 239, 241, which would apply a moment to those coupling arrangements.

As discussed above, the intermediate connecting portions 301, 303 may, in one configuration, bend towards the centre of the support apparatus, such that the spacing between the two upper upstanding members 303, 307 is smaller than the spacing between the two lower upstanding members 233, 235. This results in the mechanical features 311, 313 being located on the outer walls of the upstanding members, so that a supported accessory does not obscure the top of the breathing assistance apparatus 10, 10', which may comprise a user interface. Additionally, the narrower spacing between the upper upstanding members 303, 307 results in a smaller handle 309, thereby urging a user to hold the support apparatus 200 by the central portion when carrying it. A wider handle may facilitate a user being able to lift the support apparatus by a portion of the handle 309 closer to the side, resulting the support apparatus 200 and breathing assistance apparatus 10, 10' being tipped when lifted. This is undesirable, particularly when the breathing assistance apparatus contains liquid in a humidification chamber, as the tipping could result in the liquid escaping the chamber.

The mechanical feature(s) 311, 313, 315 has/have a shape that is complementary to the shape of the conduit and/or patient interface such as a cannula to be held by the mechanical feature(s). The mechanical feature(s) could have any suitable configuration. For example, the mechanical feature(s) could comprise one or more of: a recess or groove; a clip; a hinge mechanism; a compliant sling or strap; a hook and loop fastener; or any other suitable configuration. In one configuration, the mechanical feature(s) comprise(s) two recesses, with one of the recesses configured to receive the conduit and the other of the recesses configured to receive the patient interface such as a cannula. In another configuration, the mechanical feature(s) comprise(s) one or more compliant slings. In another configuration, the mechanical feature(s) comprise(s) one or more clips. In another configuration, the mechanical feature(s) comprise(s) one or more hook and loop fasteners that is/are configured to secure around the conduit and/or patient interface such as a cannula to hold the conduit and/or patient interface such as a cannula in position.

When the holder has a plurality of mechanical features, different mechanical features could be used in combination.

As shown in FIGS. 35 to 38, the support apparatus 200 may be provided with an accessory support extension 500. The accessory support extension 500 couples to one or other of the first mechanical features 311. In some configurations, the accessory support extension 500 is configured to couple to either one of the first mechanical features 311 so the accessory support extension 500 could be used on either side of the support apparatus 200. In other configurations, the accessory support extension 500 is configured to couple to only one of the first mechanical features 311. The support apparatus 200 may be provided with one or two accessory support extensions 500.

Figure 38:
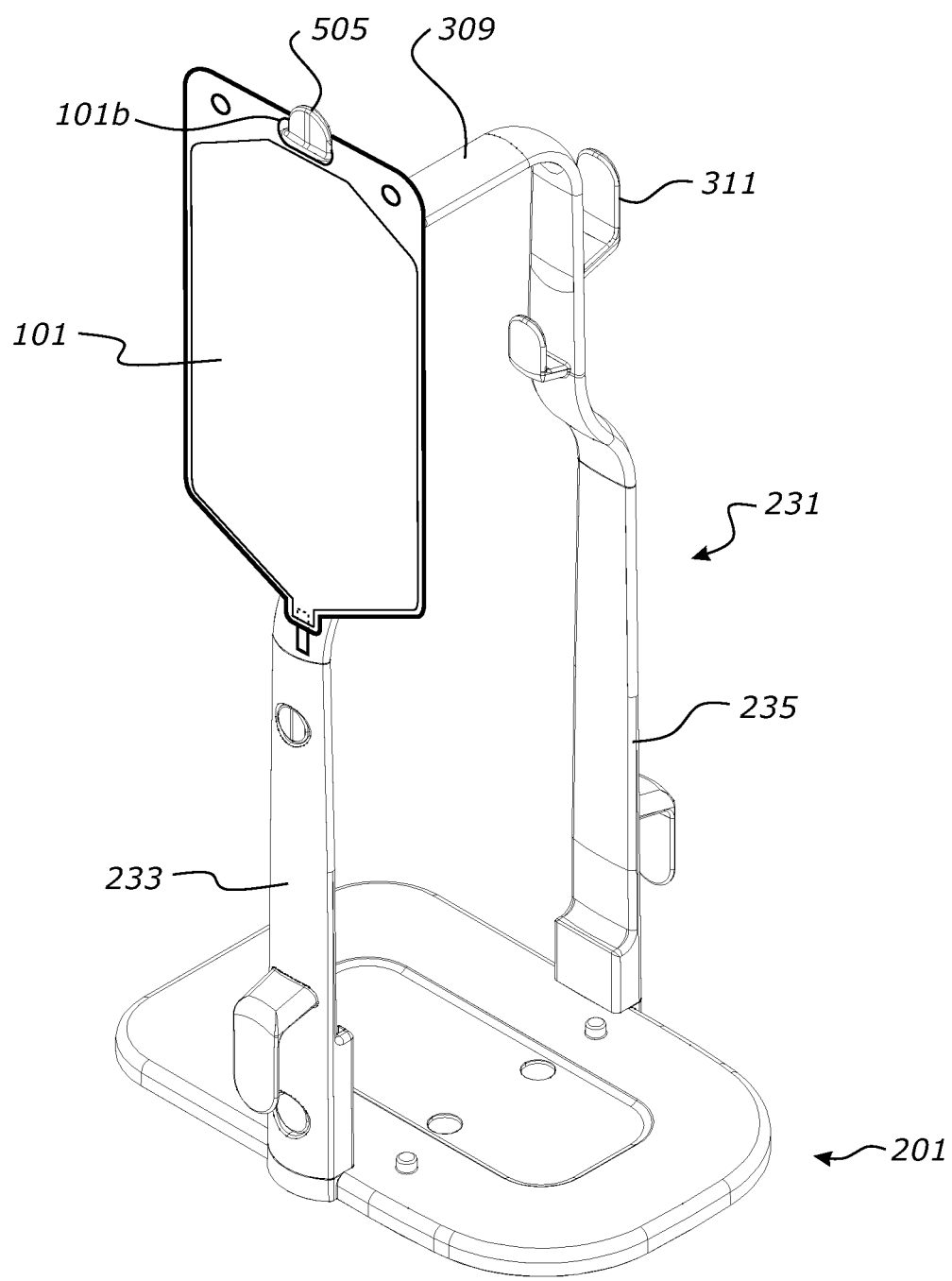
FIG. 38 is a front overhead perspective view of the support apparatus with accessory support extension, holding a liquid bag.

The accessory support extension 500 couples to the first mechanical feature 311 to provide a greater height holder for an accessory that would be provided by the mechanical features 311 in the absence of the accessory support extension 500. This enables a longer or taller accessory to be supported. Additionally or alternatively, in the case of a liquid bag 101 (as shown in FIG. 38 for example), the increased height of the liquid bag 101 above the stand 201 of the support apparatus provides an enhanced liquid delivery pressure from the liquid bag 101 to the liquid chamber 151 of the breathing assistance apparatus 10, 10'.

Figure 37:
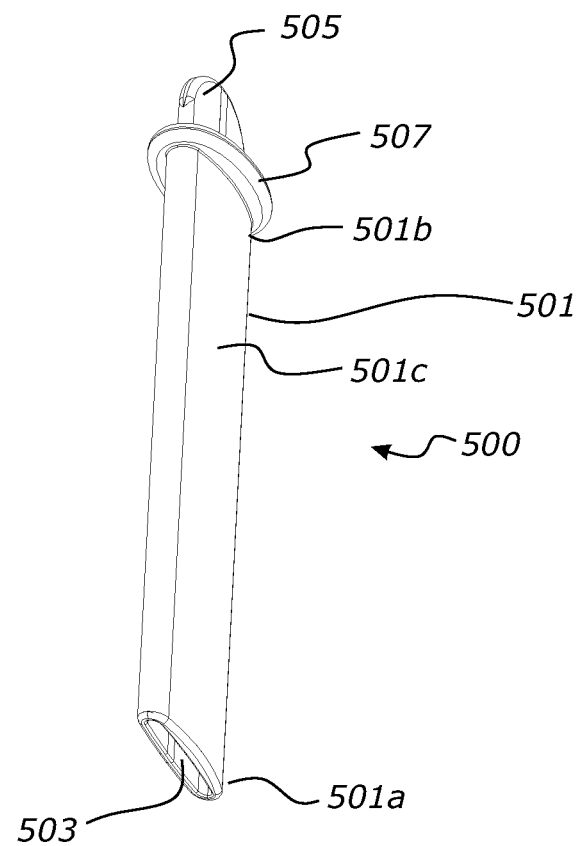
FIG. 37 is an underside perspective view of the accessory support extension.

A lower end of the accessory support extension 500 is configured to couple to the mechanical feature 311 and an upper end of the accessory support extension 500 is configured to support the accessory. Referring to FIG. 37, the accessory support extension 500 comprises an elongate generally cylindrical body portion 501. The body portion 501 could have any suitable cross-sectional shape, such as circular, oblong, or any other suitable shape.

A lower end 501a of the body portion 501 is configured to couple to the mechanical feature and comprises a coupling recess 503 that has an internal shape that is complementary to the shape of the distal support portion 311b of the first mechanical feature 311. The coupling recess 503 may removably engage with the distal support portion 311b by lowering the accessory support extension 500 onto the first mechanical feature 311.

A support feature 505 for supporting an accessory projects upwardly from an upper end 501b of the body portion 501. In the form shown, the support feature 505 has a shape corresponding to the shape of the distal support portion 311b of the upper mechanical feature, but could instead have a different shape. The support feature 505 will be configured to extend into or through a complementary receiver 101b on the accessory to be supported, such as a support ring, recess, or aperture for example. The support feature 505 may extend upwardly from the centre of the body portion 501, and the body portion 501 may be oriented substantially vertically when the accessory support extension 500 is coupled to the first mechanical feature 311. The support feature 505 is thereby positioned substantially directly above the lower upstanding members 233, 235. This means that the weight of the supported accessory does not produce a large moment in the lower upstanding members 233, 235, which is particularly useful for heavier accessories, such as a liquid bag 101.

A restriction feature 507 is provided between the upper end 501b of the body portion 501 and the lower end of the support feature 505 to restrict downward movement of a supported accessory relative to the accessory support extension 500. The restriction feature 507 projects transversely (relative to the elongate direction of the body portion 501) from the lower end of the support feature 505, and optionally transversely beyond the side walls 501c of the body portion 501, to restrict downward movement of the accessory. In the form shown, the restriction feature 507 comprises a flange that extends outwardly beyond the periphery of the body portion 501 around the entire body portion 501. However, the restriction feature 507 could have any other suitable configuration. For example, the support feature 507 could comprise one or more transversely extending projections that extend generally radially outwardly from the lower end of the support feature 505.

The upper end of the accessory support extension 500 could alternatively have a base portion and distal support portion similar to the base portion 311a and the distal support portion 311b of the first mechanical feature 311, to support an accessory.

The support apparatus 200 has a first mount 351 that is configured to releasably couple the support apparatus 200 with the mounting feature 127 of the first breathing assistance apparatus 10. The support apparatus 200 also has a second mount 371 that has a different configuration from the first mount 351 and that is configured to releasably couple the support apparatus 200 with a mounting feature of the second breathing assistance apparatus 10'. The second breathing assistance apparatus 10' has a different configuration from the first breathing assistance apparatus 10.

Figure 7:
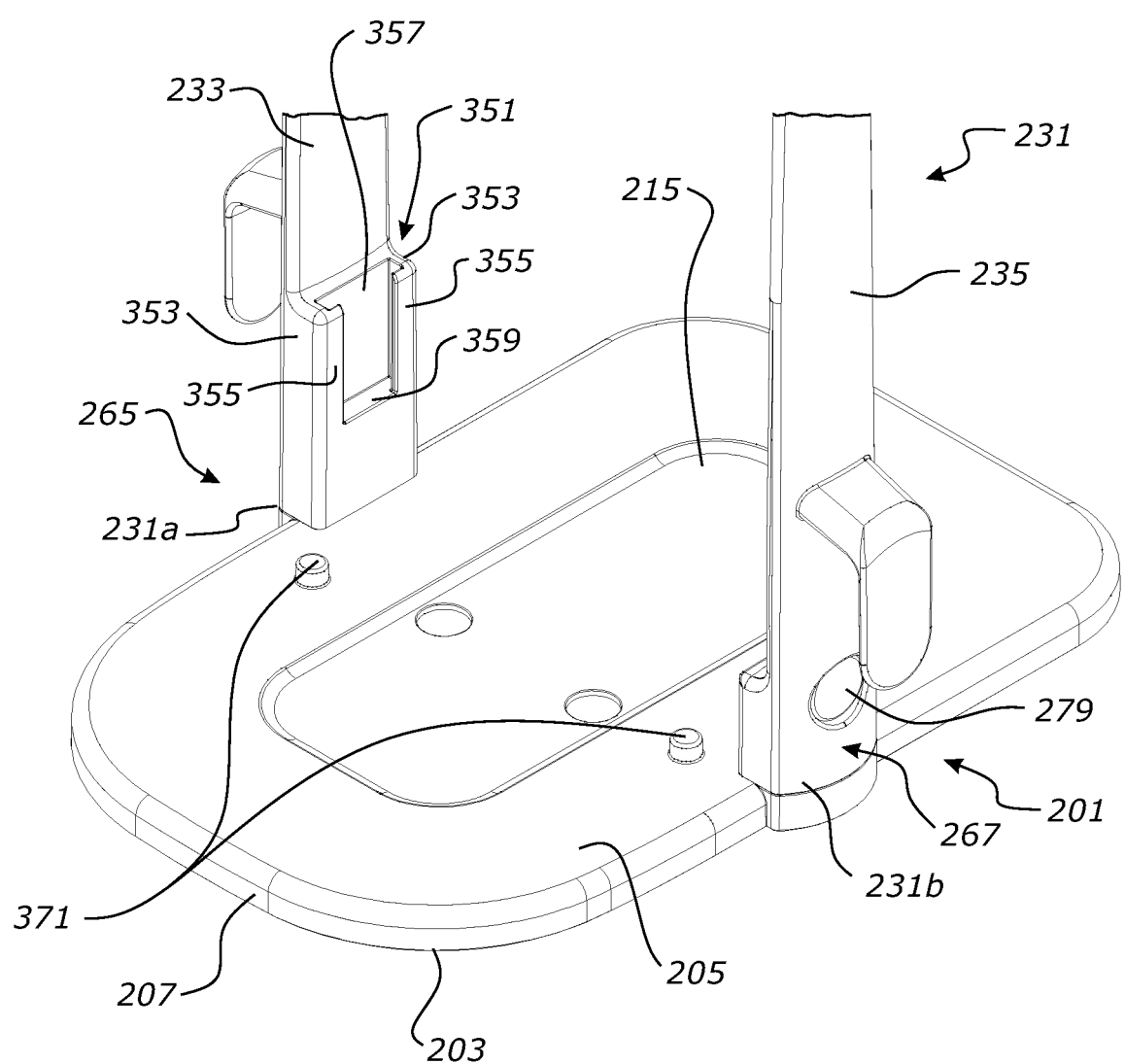
FIG. 7 is a right side/overhead perspective view of a lower region the support apparatus showing exemplary first and second mounts for releasably coupling the support apparatus with first and second configuration breathing assistance apparatuses.

In the form shown, the first mount 351 is on the holder 231. More particularly, the first mount 351 is provided at or adjacent the first end 231a of the holder 231 on the lower upstanding member 233. Referring to FIG. 7, the first mount 351 comprises a receptacle having opposed slots formed by side walls 353, relatively narrow front walls 355, and a rear wall 357 that extends between the side walls. The rear wall 357 is wider than the front walls 355, so that the front walls define an opening between the slots. The base of the receptacle is defined by a bottom wall 359.

The receptacle of the first mount 351 is arranged to receive the tongue 131 of the mounting feature 127 of the apparatus 10, by sliding the tongue downwardly in a generally vertical direction into the slots of the upper mount with the edges of the tongue received between the shortened front walls 355 and the rear wall 357 (by lowering the breathing assistance apparatus 10 relative to the first mount 351). The slots and the side walls 353 of the receptacle form alignment features to align the first mount 351 with the complementary mounting feature 127 of the breathing assistance apparatus. In alternative configurations, different alignment feature(s) may be used, such as one or more ribs, protrusions, and/or other features. The alignment feature(s) protect against horizontal movement or misalignment of the support apparatus 200 with the breathing assistance apparatus 10 and assist with controlling the insertion extent of the tongue 131 of the breathing assistance apparatus 10 into the receptacle. Additionally, or alternatively, one or more stops may be provided to limit the insertion extent of the tongue 131 into the receptacle.

The tongue 131 and/or the first mount 351 may comprise a connection feature to releasably fasten the support apparatus 200 to the breathing assistance apparatus 10, such as feature(s) that must pass one another by flexing the tongue 131 to enable the support apparatus and breathing assistance apparatus 10 to be releasably coupled or separated.

The holder 231 further comprises an optional support member 361 spaced from the first mount 351 to assist with supporting the first breathing assistance apparatus 10 when the first breathing assistance apparatus 10 is releasably coupled to the support apparatus 200. The first mount 351 is configured to support a first side of the breathing assistance apparatus, and the support member 361 is configured to support a second, opposite side of the breathing assistance apparatus 10. The support member 361 is positioned at or adjacent the second end 231b of the holder 231 on the second upstanding member 233. This configuration supports the first breathing assistance apparatus 10 substantially evenly across the support apparatus.

Instead of being part of the holder 231, the support member 361 could be provided elsewhere on the support apparatus. For example, the support member 361 could comprise, or could be part of, a separate upstanding component or part of the base 203.

In the form shown, the support member 361 comprises a shoulder that protrudes inwardly toward a centre of the support apparatus 200 from an inner face of the second upstanding member 235. Alternatively, any other suitable configuration member could be used, such as one or more inward projections for example. An upper surface 361a of the support member 361 is generally complementary to the underside of the housing 100 of the first breathing assistance apparatus 10, and may comprise an arcuate surface. The spacing between the first mount 351 and the support member 361 is smaller than the width of the housing 100 of the first breathing assistance apparatus so that the first mount 351 and the support member 361 support the first breathing assistance apparatus 10 and the first breathing assistance apparatus 10, cannot contact the base 203 when the holder 231 is mounted to the base 203. This will prevent the first breathing assistance apparatus 10 from contacting the second mount 371.

The first mount 351, and optionally the support member 361, is/are configured to support the breathing assistance apparatus such that an underside 115 of the breathing assistance apparatus 10 is positioned with a spacing above a top surface 205, 215 of the base 203, when the breathing assistance apparatus 10 is coupled with the support apparatus 200. The spacing between the top surface 205, 215 of the base and the underside 115 of the breathing assistance apparatus 10 will advantageously be sufficient to provide a storage space for accessories of the breathing assistance apparatus when they are not in use. For example, a liquid bag and tubes for delivering liquid to the liquid chamber 151, breathing conduit, and/or the power cord of the breathing assistance apparatus 10. A bottom edge of the battery 125 of the breathing assistance apparatus 10 may rest on the upper surface of the base 203. The bottom edge of the battery 125 may assist with supporting the breathing assistance apparatus 10. Alternatively, a shorter battery 125 that does not extend past the underside of the breathing assistance apparatus 10 may be provided. By supporting the breathing assistance apparatus 10 above the stand, a larger battery can be accommodated.

In some configurations, the spacing between the upper surface of the receptacle 215 and the underside 115 of the breathing assistance apparatus 10 may be between about 50 mm and about 150 mm, or may be between about 50 mm and about 100 mm, or may be between about 70 mm and about 90 mm, or may be about 80 mm, for example. If a receptacle 215 is not provided, that may be the spacing between the upper surface 205 of the base and the underside 115 of the apparatus 10.

FIGS. 8-13 show the first breathing assistance apparatus 10 supported by the first mount 351 and the support member 361, with the first breathing assistance apparatus 10 positioned between the first upstanding member 233 and the second upstanding member 235. The first upstanding member 233 and the second upstanding member 235 may be spaced apart to be in close proximity to, or contact, the side walls 109, 111 of the first breathing assistance apparatus 10 when it is releasably coupled to the first mount 351, to minimise lateral movement of the first breathing assistance apparatus 10 and/or provide a retaining force of the first breathing assistance apparatus 10 on the support apparatus 200. However, the retaining force may not be required, because the support apparatus 200 and releasably coupled first breathing assistance apparatus 10 can be lifted by the handle 309 of the support apparatus rather than by lifting the first breathing assistance apparatus 10. Because the first breathing assistance apparatus 10 is lowered into the mount 351, the breathing assistance apparatus 10 is held in the mount 351 by its own weight and lateral movement can be prevented by the mount 351, minimising the likelihood of the breathing assistance apparatus 10 falling off the mount 351 when being carried.

The second mount 371 that has a different configuration from the first mount 351 and is configured to releasably couple the support apparatus with a mounting feature of the second breathing assistance apparatus 10', is provided on the base 203 of the breathing assistance apparatus. In the form shown, the second mount 371 comprises one or more upstanding projections that extend upwardly from the upper surface 205 of the base 203. The projection(s) 371 is/are configured to engage with complementary recess(es) 143' (FIG. 17) in an underside of the second breathing assistance apparatus 10'.

Figure 16:
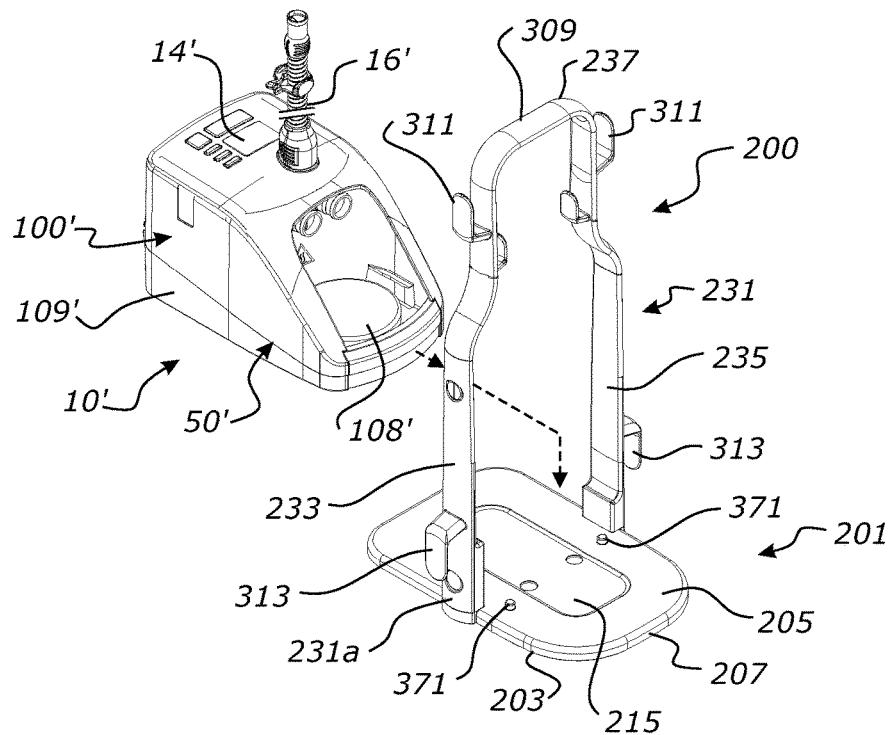
FIG. 16 left side/front overhead perspective view of the support apparatus showing the insertion of the second configuration breathing assistance apparatus into the support apparatus.
Figure 17:
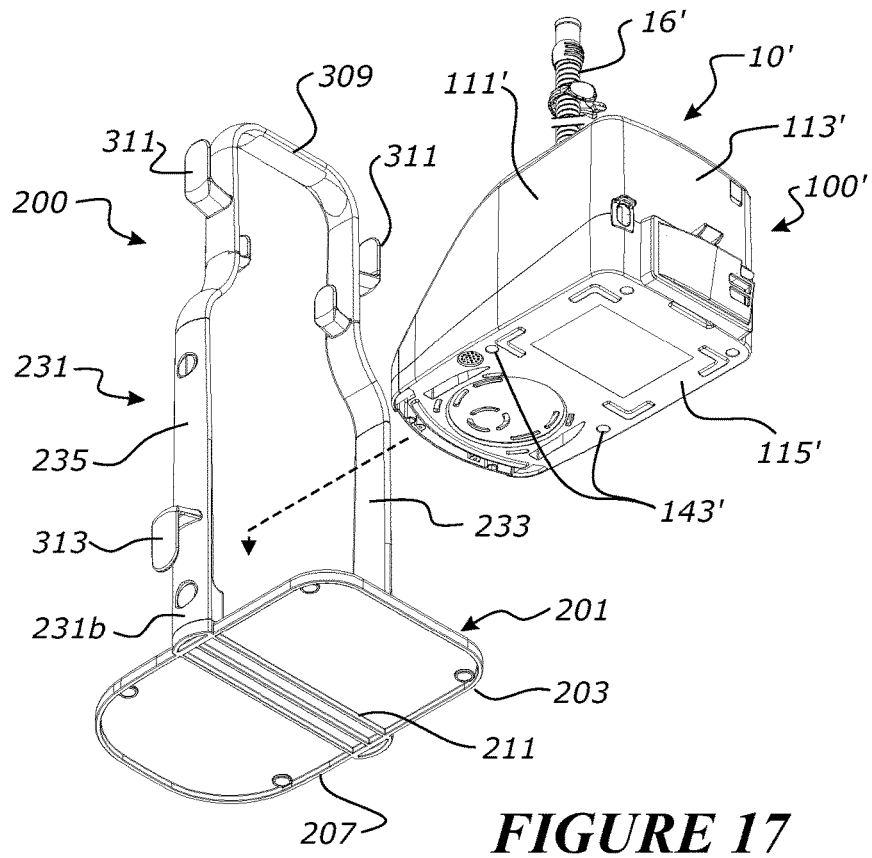
FIG. 17 is a right side/rear underside perspective view corresponding to FIG. 16.
Figure 18:
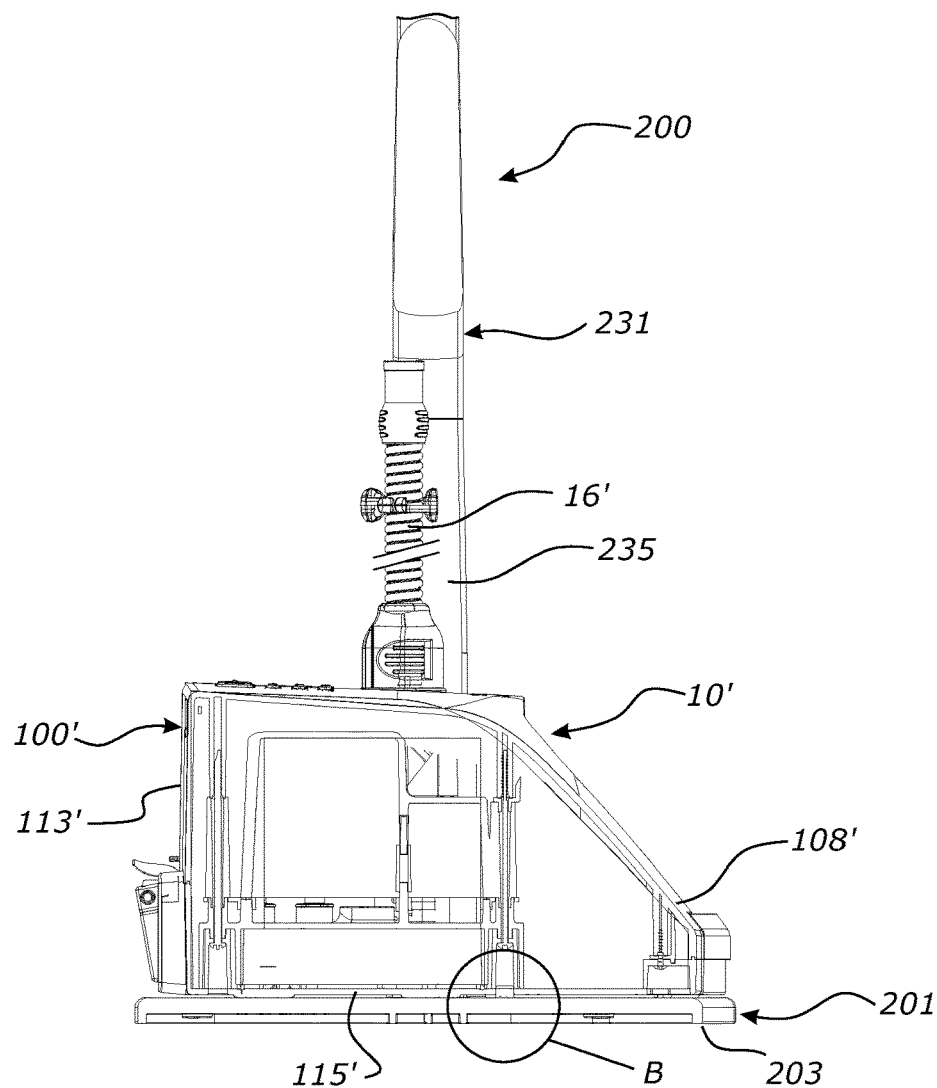
FIG. 18 is a left side sectional view of the support apparatus releasably coupled with the second configuration breathing assistance apparatus, showing the engagement of the projections of the second mount with complementary recesses in the bottom of the breathing assistance apparatus.
Figure 18A:
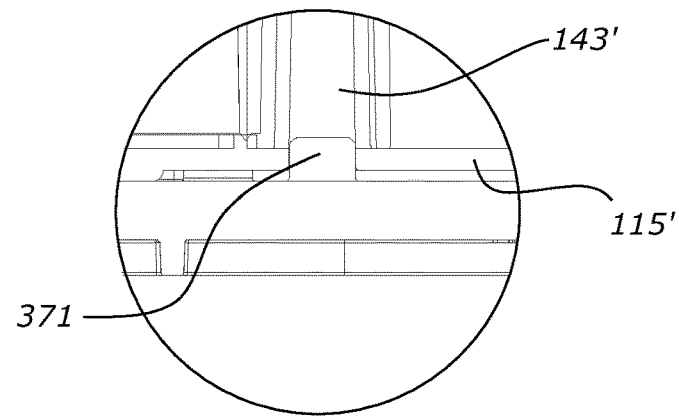
FIG. 18A is a side view of detail B of FIG. 18.

As shown in FIGS. 16 and 17, the second breathing assistance apparatus can be releasably coupled to the second mount by inserting the second breathing assistance apparatus 10' between the holder 231 and the base 203, and lowering the second breathing assistance apparatus 10' onto the base 203 so that the projections 371 are received in the recesses 143'.

Figure 14:
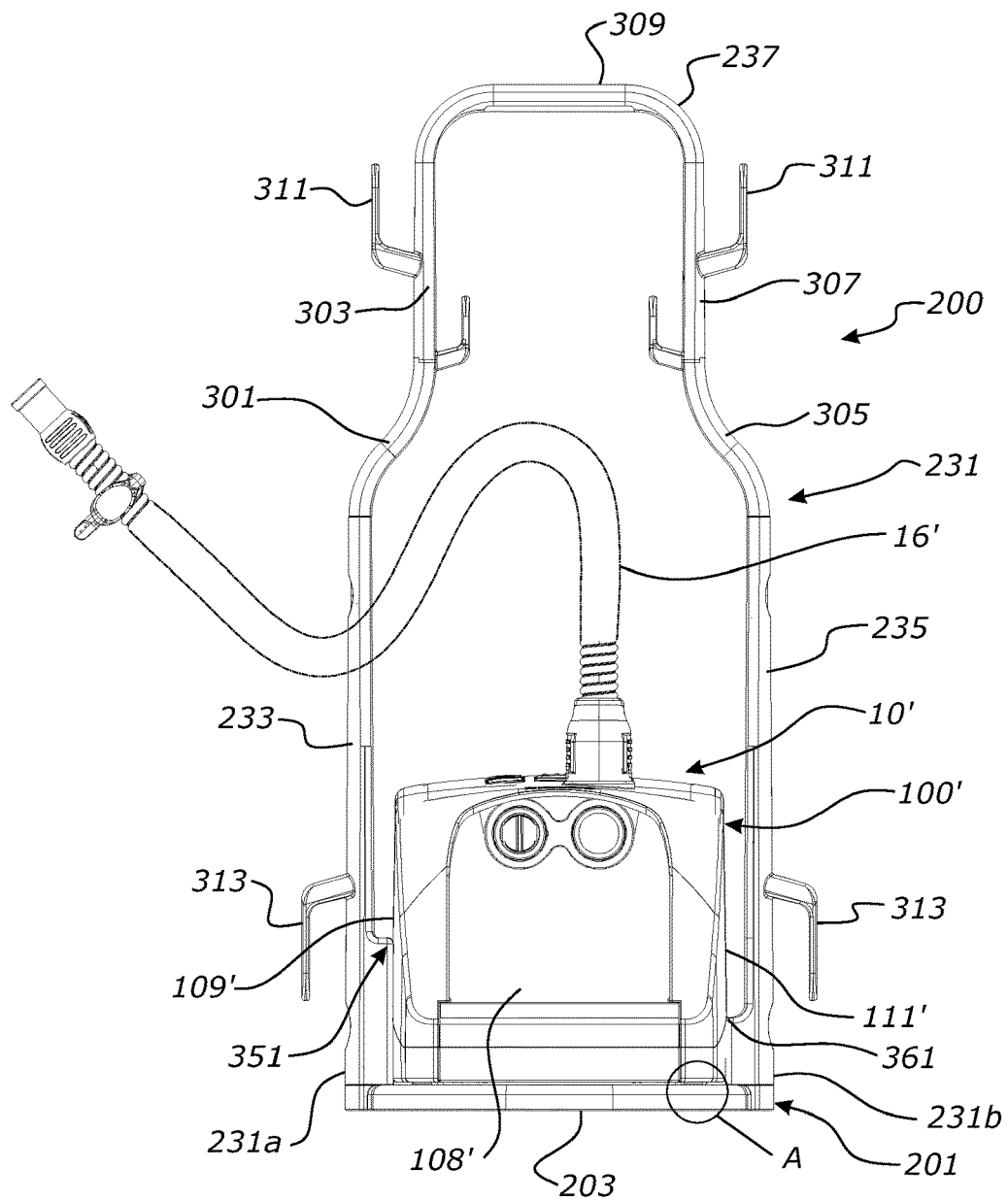
FIG. 14 is a front view of the support apparatus with a second configuration breathing assistance apparatus releasably coupled with the second mount of the support apparatus.
Figure 14A:
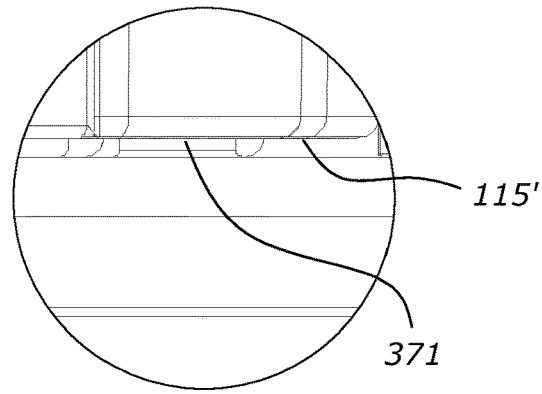
FIG. 14A is a front view of detail A of FIG. 14.
Figure 15:
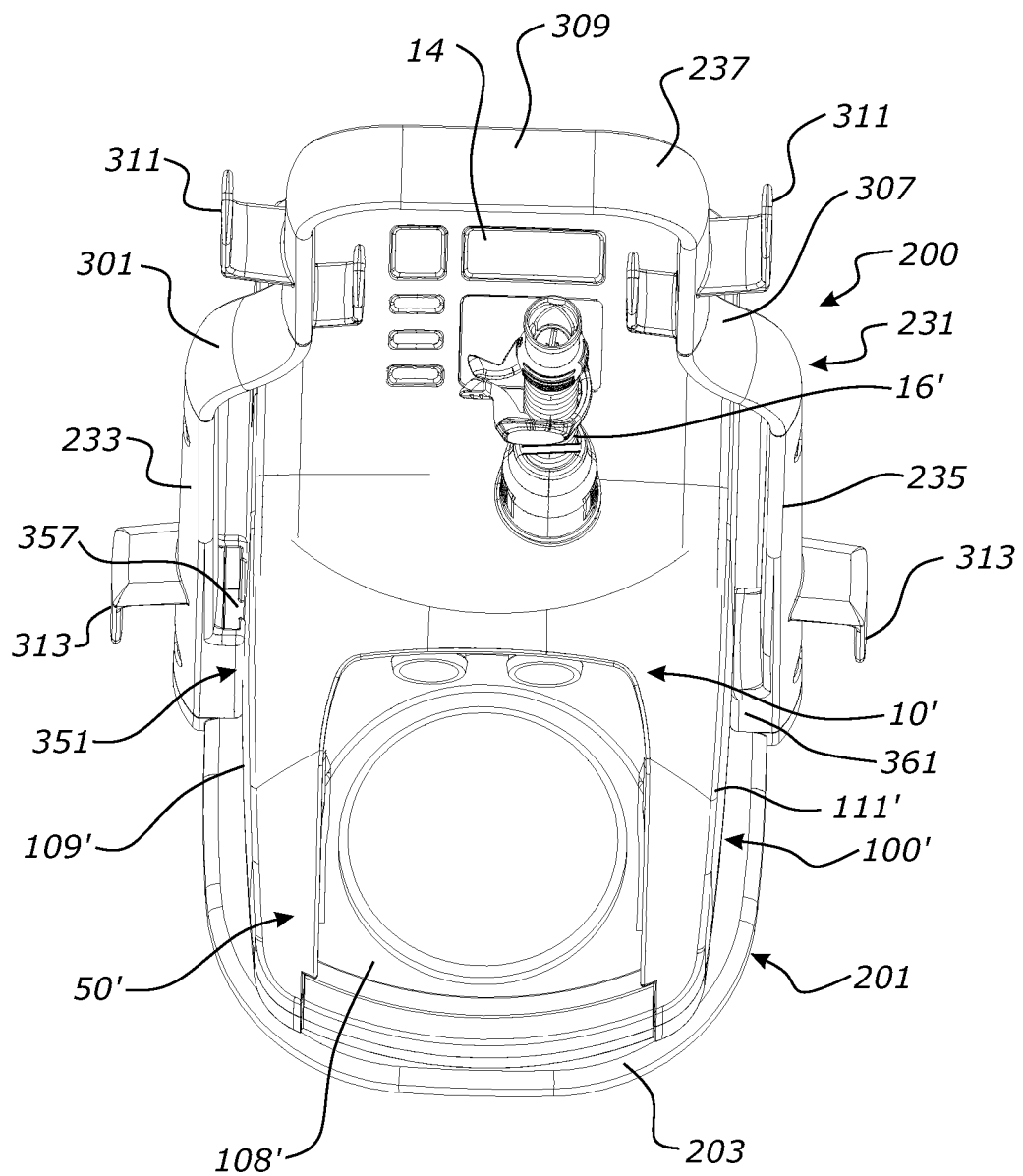
FIG. 15 is an overhead perspective view corresponding to FIG. 14.

The lateral width of the housing 100' of the second breathing assistance apparatus 10' is smaller than that of the first breathing assistance apparatus 10. Therefore, the second breathing assistance apparatus 10' can fit between the first mount 351 and the support member 361 and rest on the base 203 of the support apparatus 200. As shown in FIGS. 14 and 15, the first mount 351 and the support member 361 may be configured to be in close proximity to, or contact with, the side walls 109', 111' of the second breathing assistance apparatus 10' when the second breathing assistance apparatus 10' is releasably coupled with the second mount 371, to minimise lateral movement of the second breathing assistance apparatus 10' and/or provide a retaining force of the second breathing assistance apparatus 10' with the support apparatus 200. In a configuration without a support member 361 or where the support member 361 is provided elsewhere on the support apparatus 200, the first mount 351 and a portion of the holder 231 (such as an opposing end of the holder from the first mount for example), may be configured to be in close proximity to, or contact with, the second breathing assistance apparatus when the second breathing assistance apparatus is releasably coupled with the second mount. However, the retaining force may not be required, because the support apparatus 200 and releasably coupled second breathing assistance apparatus 10' can be lifted by the handle 309 of the support apparatus rather than by lifting the second breathing assistance apparatus 10'. Because the second breathing assistance apparatus 10' is lowered into the mount 371, the breathing assistance apparatus 10' is held in the mount 371 by its own weight and lateral movement can be prevented by the mount 371, minimising the likelihood of the breathing assistance apparatus 10' falling off the mount 371 when being carried.

The first mount 351 and the second mount 371 are configured so that only one of the first breathing assistance apparatus 10 and the second breathing assistance apparatus 10' can be releasably coupled to the support apparatus 200 at a time.

Because the second breathing assistance apparatus 10' does not have a tongue 131, the second breathing assistance apparatus 10' cannot mount to the first mount 351. Because the underside of the first breathing assistance apparatus 10 has a different configuration of recesses 143 from the recesses 143' of the second breathing assistance apparatus 10' and/or because the housing 100 of the first breathing assistance apparatus 10 cannot pass between the first mount 351 and the support 361, the first breathing assistance apparatus 10 cannot mount to the second mount 371, at least when the holder 231 is coupled to the base 203.

The described mounts 351, 371 are one exemplary configuration. Different configurations could be provided instead. For example, the second mount could have a different number or arrangement of projections. Alternatively, the second mount 371 could take a different form, such as a form similar to the first mount but at the opposite end of the arm, to mount with a suitable tongue on the right side of a second breathing assistance apparatus 10'. One or both of the mounts 351, 371 could be provided on the base 203 or on the holder 231. One or both of the mounts 351, 371 could instead comprise a hook and loop fastener between the respective surface of the support apparatus 200 and the breathing assistance apparatus 10, 10'. For example, the hook and loop fastener could be provided between the holder 231 and the first breathing assistance apparatus 10 and/or between the base 203 and the second breathing assistance apparatus 10'.

The first and second breathing assistance apparatuses 10, 10' are examples only, and the support apparatus could be configured to support different breathing assistance apparatuses with different configurations.

The support apparatus 200 may be made by an injection moulding process. Injection moulding can result in warping and other defects if the cross section of components is too thick. However, a thicker cross section for the holder 231 components allows for a more rigid structure, such that support apparatus is less likely to bend under the weight of the various accessories. A thicker cross section additionally makes the support apparatus more comfortable for a user to hold. Finally, a thicker cross section also provides more internal area for the coupling arrangements 239, 241, 265, 267 described above. In order to allow for a thicker cross section without producing defects, a material that produces low amounts of warping would be used. This material could be a thermoplastic containing a portion (e.g. 50%) of cellulose resin. The material could be reinforced nylon. Alternatively, a foamed thermoplastic such as polycarbonate, ABS, or a different foamed thermoplastic could be used. The material could alternatively be a non-foamed polycarbonate.

Referring to FIGS. 29-34, the support apparatus 200 may be provided with a removable shroud 400. The shroud 400 is arranged to cover a substantial part of the support apparatus 200 to protect and conceal the support apparatus 200, a releasably coupled breathing assistance apparatus 10, 10', and accessories. The shroud 400 will be used when the breathing assistance apparatus 10, 10' is not in use. The shroud 400 protects the breathing assistance apparatus 10, 10' and accessories from dust and other contaminants, particularly when the breathing assistance apparatus and accessories are not being used or are being stored for an extended period.

The shroud 400 may be flexible but capable of holding its general shape in the absence of external force. In an alternative configuration the shroud may be a hard material. The shroud 400 may comprise any suitable material, such as a plastic, fabric, or textile material. The shroud may be transparent, translucent, or opaque. Due to the flexible nature of the shroud 400, the shroud 400 can be folded and stored in the space between the base 203 and the underside of the first breathing assistance apparatus 10' when the shroud 400 is not in use.

In the form shown, the shroud 400 has a tapering configuration where the upper portion of the shroud 400 has a narrower width and a narrower forward-rearward dimension than the lower portion the shroud 400. The shroud 400 has opposed front and rear walls 401, 403 each having a trapezoidal shape. The lower edges of the front and rear walls 401, 403 are arranged to be adjacent to the front and rear edges of the outer perimeter of the base 203 when the shroud is placed on the support apparatus 200. Side walls 405, 407 extend between the front and rear walls 401, 403. The upper edges 405a, 407a of the side walls have a central height that is vertically higher than the outer edges 405b, 405c 407b, 407c that connect to the front and rear walls 401, 403, so that the upper edges 405a, 407a are arcuate. The lower edges of the side walls 405, 407 are arranged to be adjacent to the left and right edges of the outer perimeter of the base 203, and also adjacent to part of the front and rear edges of the outer perimeter of the base 203, when the shroud is placed on the support apparatus 200. The lower edges of the walls 401, 403, 405, 407 may extend to the bottom edge of the base 203, or may be positioned higher than the bottom edge so as to not contact a support surface (such as a floor) that the base is resting on.

A ceiling 409 of the shroud extends between the upper edges of the walls 401, 403, 405, 407, and has a convex curvature when viewed from above.

The described wall and ceiling configuration is one exemplary configuration. It will be understood that the shroud could have a different shape and configuration while still providing suitable coverage of the support apparatus 200, breathing assistance apparatus 10, 10', and accessories.

The ceiling 409 of the shroud comprises an opening 411 through which the handle 309 can pass as the shroud 400 is placed on the support apparatus 200, such that the handle 309 is accessible from an exterior of the shroud 400. The opening 411 may be sized so that the first mechanical features 311 are unable to pass through the opening 411. When placing the shroud over the support apparatus 200, the handle 309 passes through the opening 411 until the upper ends of the side walls 405, 407 or the ceiling 409 catches on the first mechanical features 311.

Figure 32:
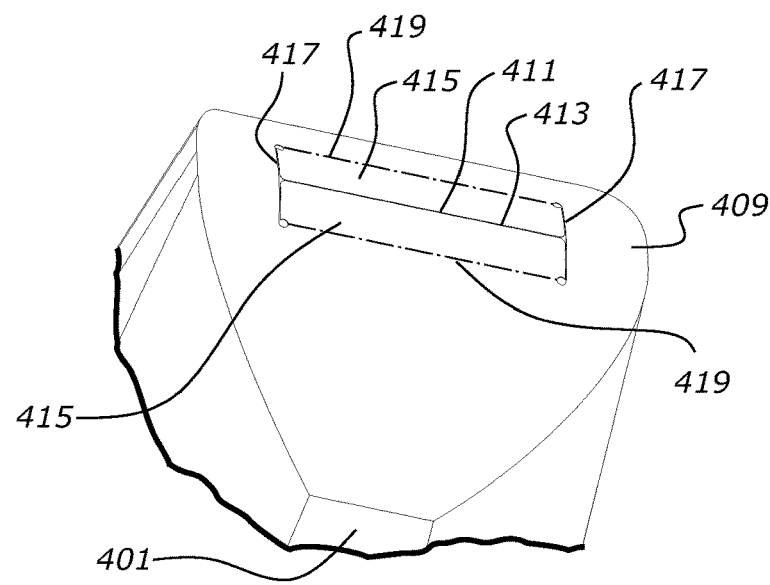
FIG. 32 is a front overhead perspective view of an upper portion of the shroud showing a first configuration of an opening in the shroud for receipt of the handle of the support.
Figure 33:
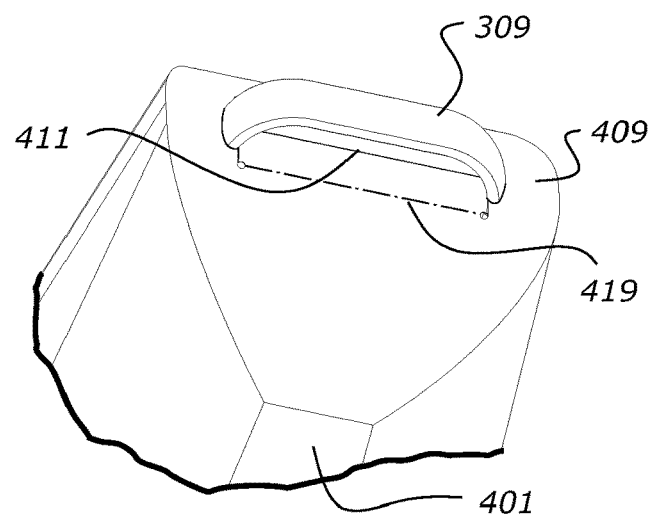
FIG. 33 is a view corresponding to FIG. 32, but with the handle extending through the opening.

Referring to FIGS. 32 and 33, in its closed configuration, the opening 411 may have a generally H-shaped configuration, with an elongate central portion 413 formed between two tabs 415 of the ceiling 409, and two end portions 417 that extend transversely to the central portion 413. The end portions 417 may be substantially parallel to each other. The central portion 413 of the opening may be a similar length to, or slightly longer than, the horizontal portion of the handle 309. The end portions 417 may be a similar length to, or slightly longer than, the forward-rearward depth of the upper upstanding members 303, 307. The tabs 415 can be lifted to open the opening, forming a substantially rectangular opening with a first elongated edge 419, a second elongated edge 419, and the two end portions 417.

The shroud 400 comprises at least one tab 415 to substantially cover the opening 411 when the shroud is in place on the support apparatus 200. The tab(s) may be flexible, or may be more rigid but flexible at their bases where they connect to the remainder of the shroud. In the form shown, the shroud comprises two opposed tabs 415 to substantially cover the opening. In the configuration with two tabs, each tab 415 extends across part of the opening from an elongated edge 419, and contact each other, or overlap, in the centre of the opening 411. The tab(s) will typically not match the length of the horizontal portion of the handle 309, but instead leave two gaps at the ends of the opening 411. These gaps will be roughly complementary to the shape and location of the upper upstanding members 303, 307 of the upper transverse connecting member 237. Alternatively, the shroud 400 may have a single tab 415 that extends at least substantially right across the opening 411 from one edge 419 to the other edge 419.

Figure 34:
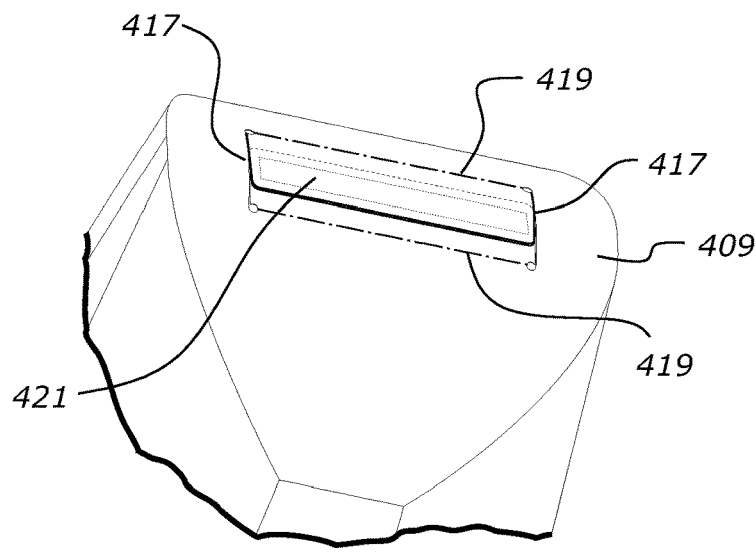
FIG. 34 is a front overhead perspective view of an upper portion of the shroud showing a second configuration of the opening for receipt of the handle of the support apparatus.
Figure 35:
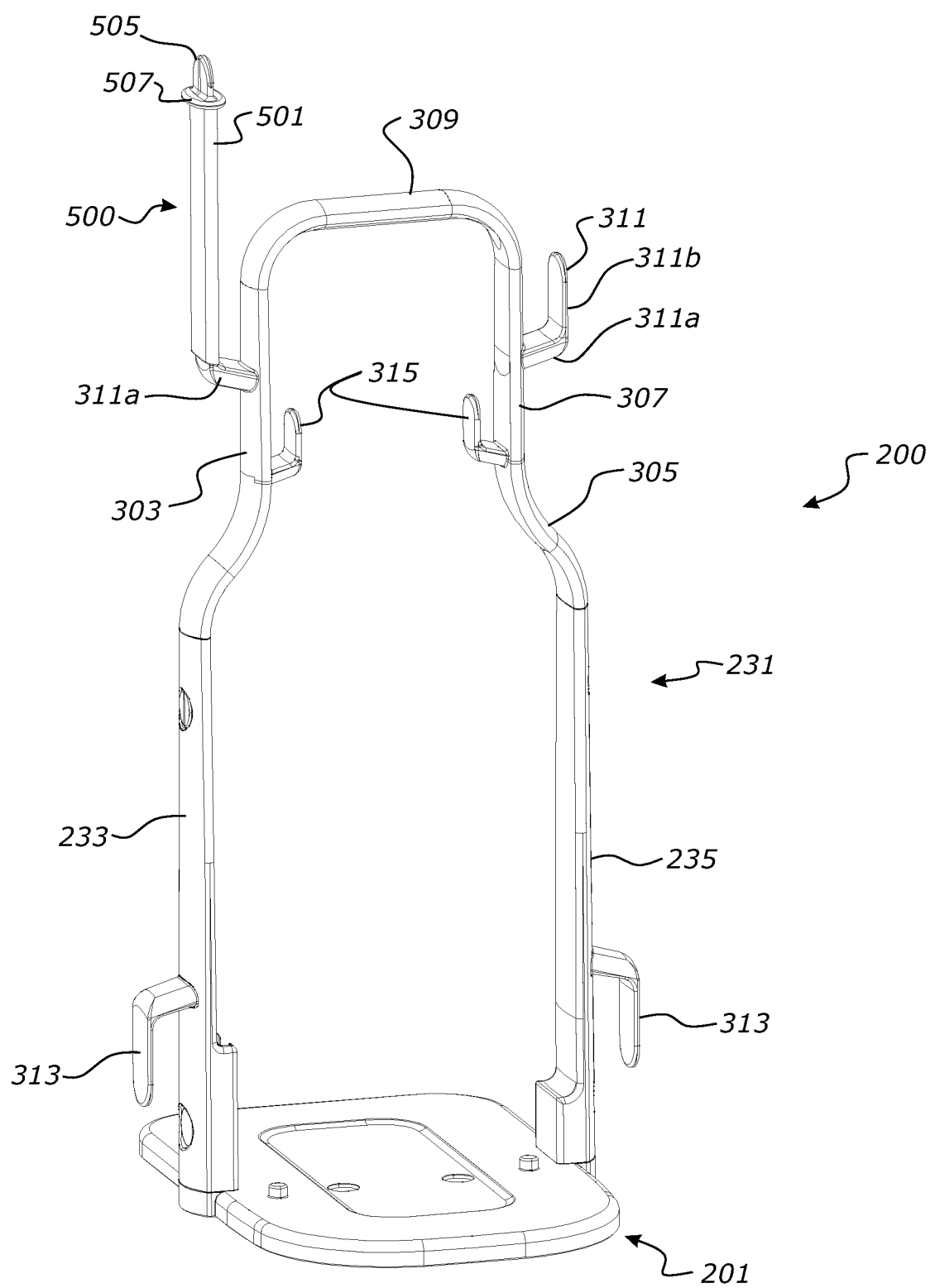
FIG. 35 is a front overhead perspective view of the support apparatus with a coupled accessory support extension.
Figure 36:
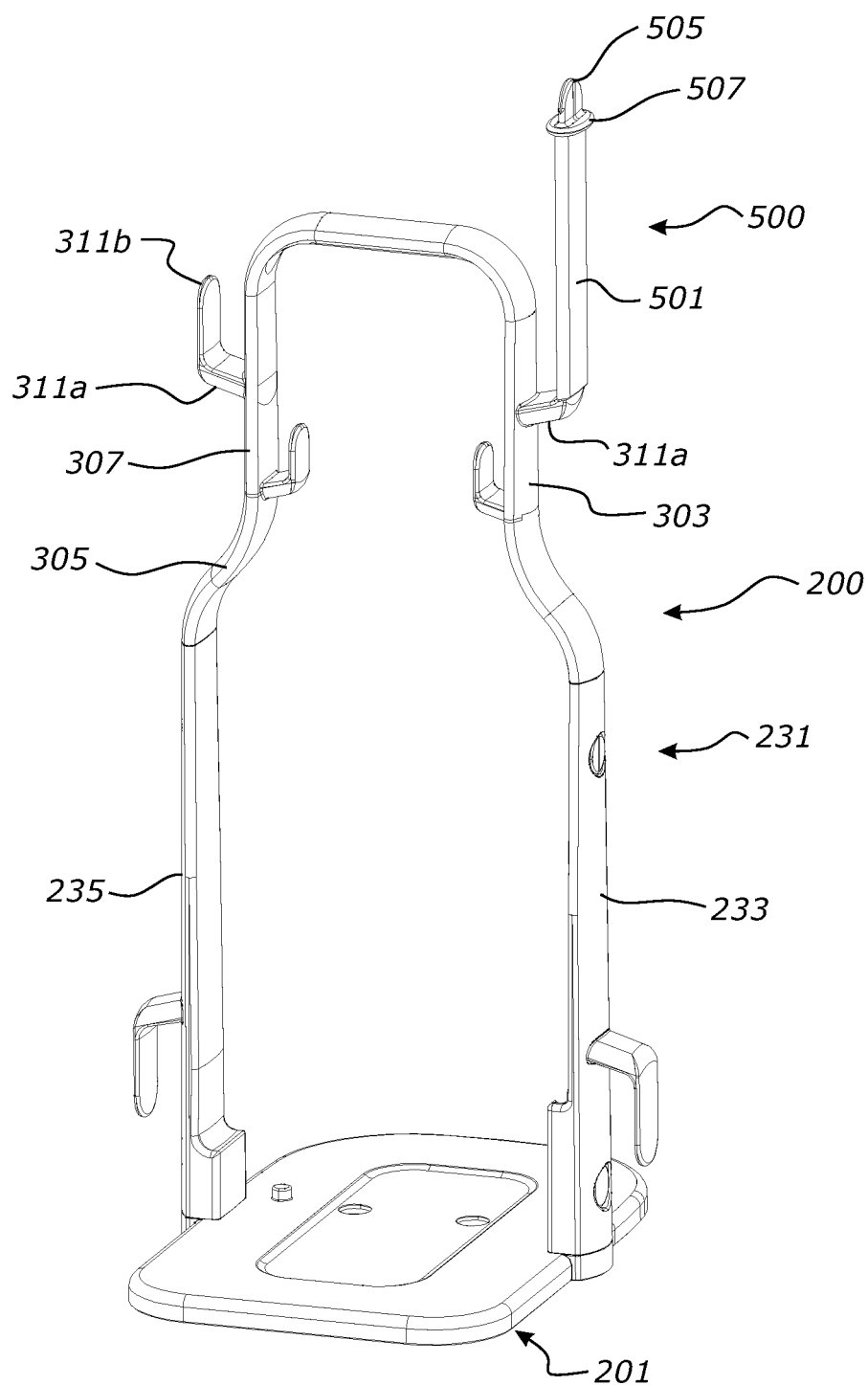
FIG. 36 is a rear overhead perspective view of the support apparatus with accessory support extension.

One tab 415 may optionally fasten to the other tab 415 to substantially close the opening 411. The cover may comprise a fastening arrangement for that purpose. As shown in FIG. 34, the fastening arrangement may comprise a hook and loop fastener 421 with complementary hooks and loops on facing surfaces of the tabs, which allows for easy attachment and detachment of the two tabs. Alternatively, when there is a single tab 415, the tab 415 and a portion of the ceiling 409 may comprise the hook and loop fasteners.

Figure 29:
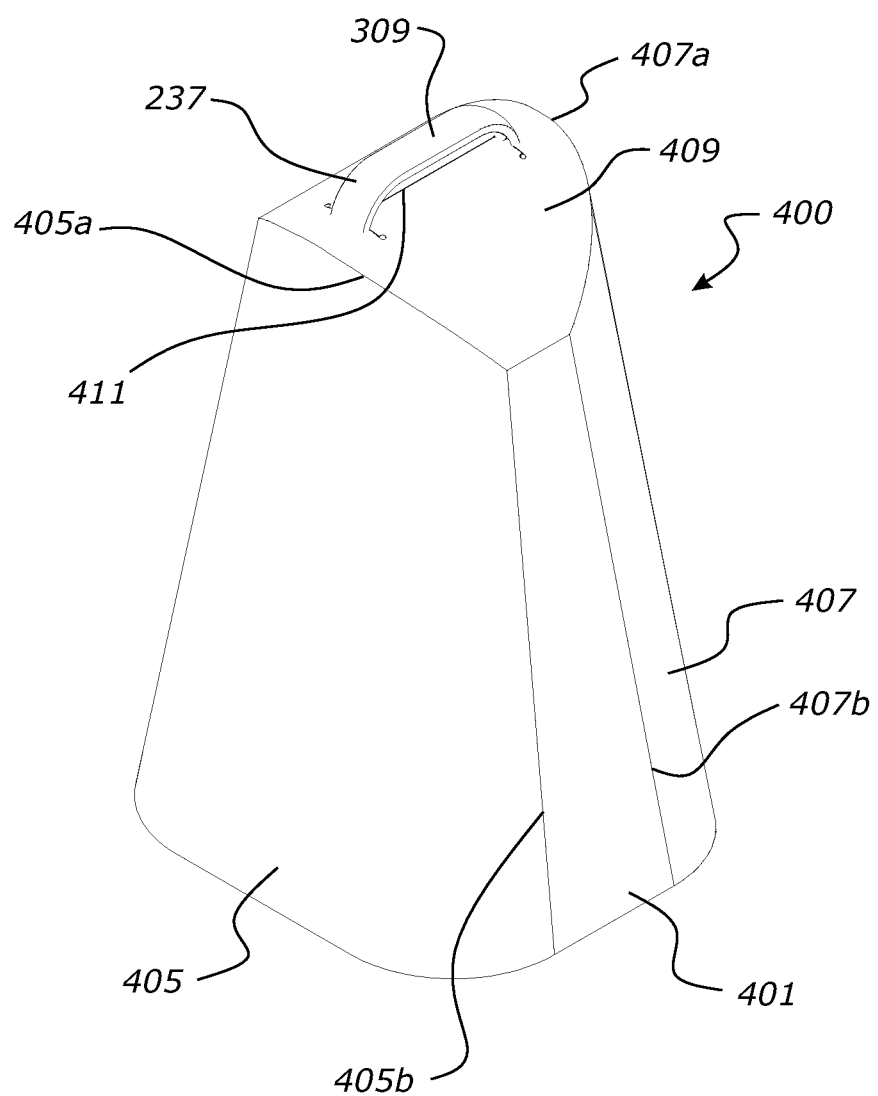
FIG. 29 is a left side/front overhead perspective view of the support apparatus with a removable shroud positioned on the support apparatus.
Figure 30:
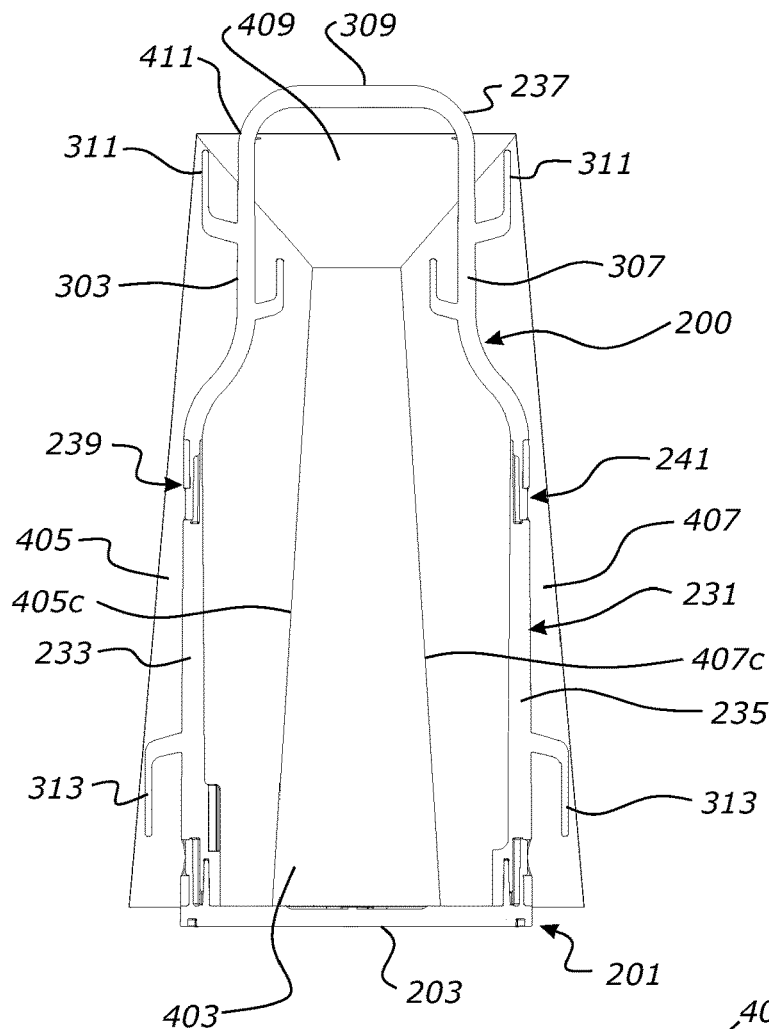
FIG. 30 is a front sectional view of the shroud on the support apparatus.
Figure 31:
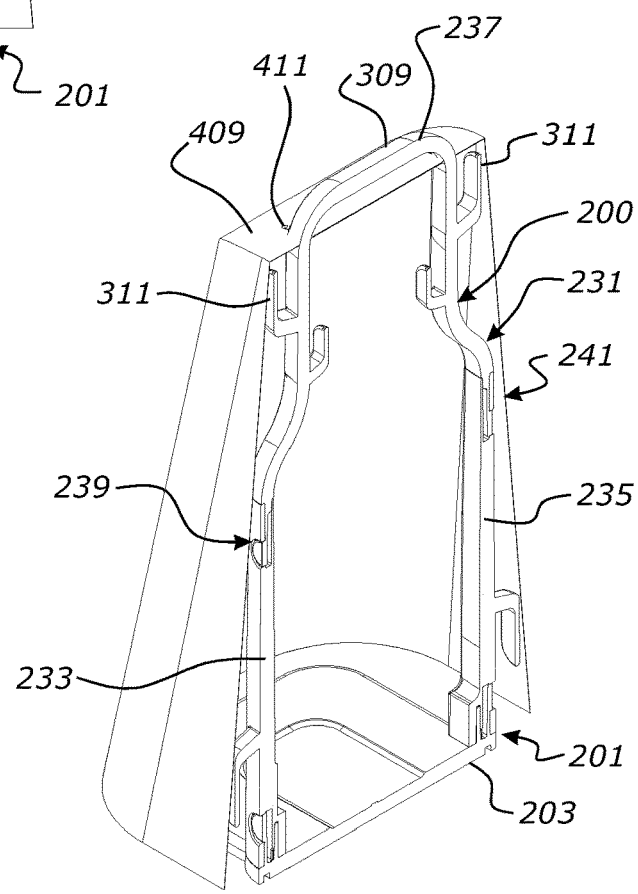
FIG. 31 is a left side/front overhead perspective sectional view of the shroud on the support apparatus.

When the cover is placed on the support apparatus 200 and the tab(s) 415 substantially cover the opening 411, the arrangement will have the appearance shown in FIG. 29. The breathing assistance apparatus 10, 10' and accessories will be obscured, and the support apparatus 200 almost entirely obscured, with the upper end of the upper transverse connecting member 237 including the handle 309 extending from the two remaining holes 417 at the end of the opening 411. This setup provides the benefits of protecting and obscuring the breathing assistance apparatus 10, 10' and accessories, minimising dust and other contaminants getting to the breathing assistance apparatus 10, 10' and accessories, while still exposing the handle 309 such that a user can easily carry the assembly. The cover may also visually conceal the breathing assistance apparatus, as home users may not want the apparatus to be seen.

Only one breathing assistance apparatus 10, 10' can be coupled with the support apparatus 200 at a time. The support apparatus 200 will be positioned on a support surface, either when the apparatus 10, 10' is in use or is not in use. When the apparatus 10, 10' is not in use, the conduit 16 and/or patient interface 17 such as a cannula will be held in place relative to the support apparatus 200 and the apparatus 10, and held above the support surface, by the mechanical feature(s) 311, 313, 315.

By enabling the support of different breathing assistance apparatuses 10, 10' and accessories, a user will not need to buy multiple support apparatuses for use with different breathing assistance apparatuses or when they change their breathing assistance apparatus.

The support apparatus 200 provides a portable arrangement that is easily placed on a support surface such as floor or table, and that keeps the conduit and/or patient interface such as a cannula and breathing assistance apparatus 10, 10' off the ground, even if the conduit and other accessories are long. This reduces dust and particulate ingress into the breathing assistance apparatus.

The handle 309 enables the support apparatus 200, breathing assistance apparatus 10, 10', and accessories to be lifted and carried by a user.

Figure 40:
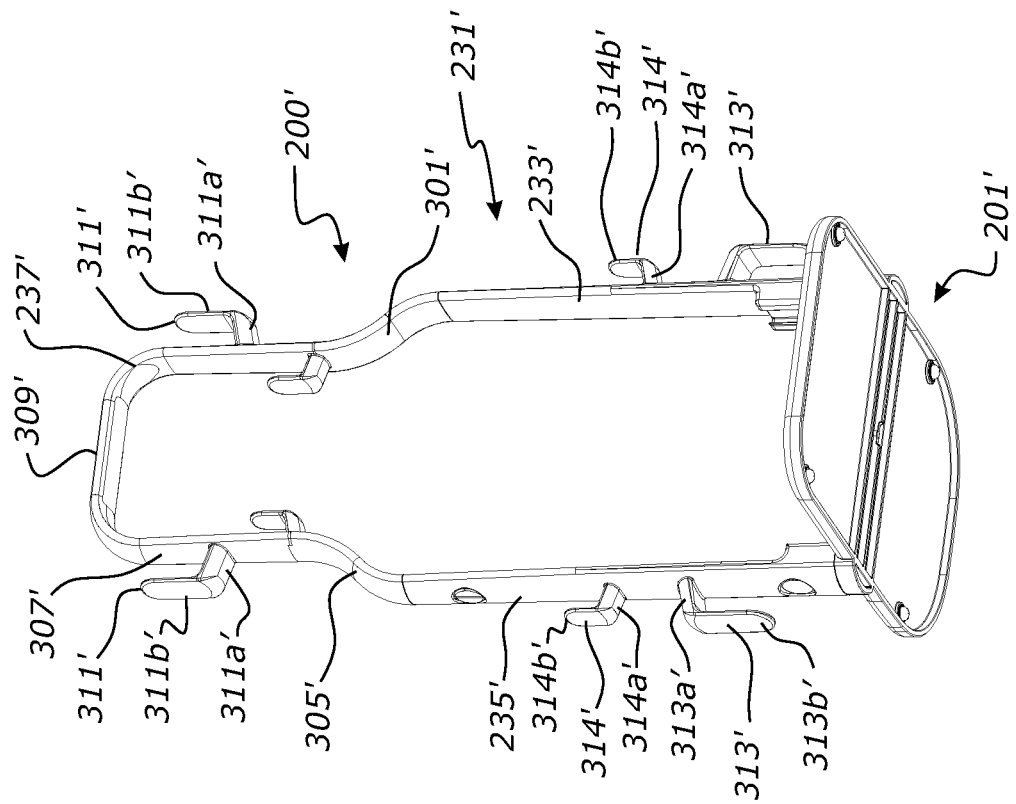
FIG. 40 is a right side/rear bottom perspective view of the support apparatus.
Figure 39:
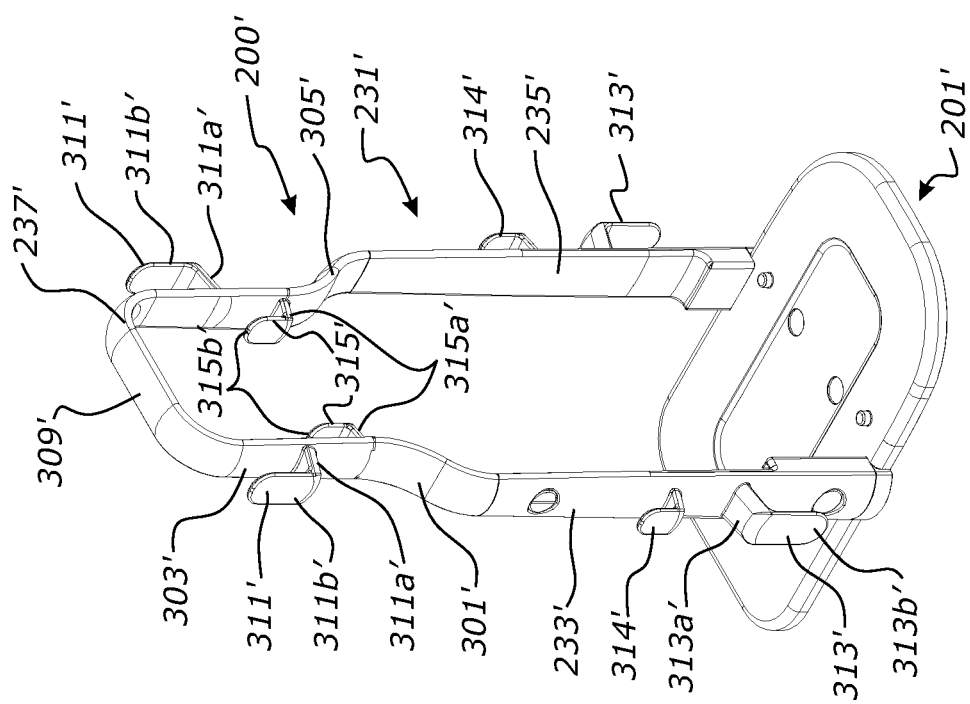
FIG. 39 is a left side/front overhead perspective view showing an alternative configuration support apparatus for the breathing assistance apparatus.

FIGS. 39 and 40 show a second configuration support apparatus/carrier 200'. Unless described below, the features and functionality of the second configuration support apparatus/carrier 200' are as described above with reference to support apparatus/carrier 200, and like reference numerals indicate like parts with the addition of a prime (').

In this configuration, the holder 231' of the support apparatus comprises at least one third outer mechanical feature 314' for holding and supporting an accessory of a breathing assistance apparatus 10, 10', such as a conduit 16, 16' and/or patient interface 17 and/or tube(s) 101a from a liquid bag or liquid container 600 and/or power cord 103.

The at least one third outer mechanical feature 314' has a shape that is complementary to the shape of the accessory. The accessories can be supported in any desired arrangement from the mechanical features 311', 313', 314', 315' of the support apparatus, if the mechanical features do not have a configuration that is specific to a particular accessory.

In the form shown, the first holder portion on the outer left side of the holder 231' has the first mechanical feature 311' on the upper upstanding member 303', the second opposed mechanical feature 313' on the lower upstanding member 233', and the third mechanical feature 314' on the lower upstanding member 233'. The third mechanical feature 314' is provided immediately above the second mechanical feature 313'.

The second mechanical feature 313' extends in a second, downward, direction from the lower upstanding member 233'. The third mechanical feature 314' extends in a first, upward, direction from the lower upstanding member 233'. The second direction is substantially opposite to the first direction. The third mechanical feature 314' extends upwardly so that an accessory can be hung from the third mechanical feature without using the second mechanical feature 313'.

The opposed mechanical feature 313', 314' are configured so that an accessory can be wrapped around the mechanical features in loops. This provides a tension force in the accessory that helps prevent the accessory from coming loose, particularly when the support apparatus and accessory are being carried.

A shorter accessory, such as a liquid conduit for an auto-refilling humidifier liquid chamber 151 for example, can be looped around opposed mechanical features 313', 314'. A longer accessory, such as a power cord or patient conduit, can be looped around opposed mechanical features 311', 313'.

Additionally or alternatively, a shorter accessory, such as a liquid conduit for an auto-refilling humidifier liquid chamber for example, can be hung from the third mechanical feature 314'. The liquid conduit may be shorter than a patient conduit 16, so the first mechanical features 311' may be located too high for supporting the liquid conduit.

In the configuration shown, the right side of the holder 231' has a second holder portion on an outer right side of the holder 231'. The second holder portion comprises first, second, and third mechanical features 311', 313', 314', and the features and functionality of those features are as described above for the first holder portion.

In the form shown, each mechanical feature comprises a base portion 311a', 313a', 314a', 315a' that extends from the respective upstanding member 303', 307', 233', 235', and a distal support portion 311b', 313b', 314b', 315b' that is configured to support the accessory between the distal support portion and the respective upstanding member. The distal support portion 311b', 313b', 314b', 315b' may be substantially parallel to the respective upstanding member 303', 307', 233', 235'. The distal support portions 311b', 314b', 315b' extend upwardly, and the distal support portions 313b' extend downwardly.

As shown in FIGS. 41 and 42, a liquid container 600 is provided for delivering liquid to the humidifier liquid chamber 151. For example, the container 600 may deliver water to an auto-refilling humidifier liquid chamber. The container 600 is configured to hold liquid. The container 600 is configured to couple to the support apparatus 200 or 200'.

Referring to FIGS. 43 to 50, the container 600 comprises a body 601 for holding liquid. The body comprises a top 603, a base 605, and a peripheral wall portion 607 extending between the top 603 and the base 605. In the form shown, the container 600 has a generally polygonal shape in top view, and the peripheral wall portion comprises a front wall 607a, a left side wall 607b, a rear wall 607c, and a right side wall 607d. However, the body could have any other suitable shape (e.g. circular or oblong) in top view, and the peripheral wall portion could be shaped accordingly.

In the form shown, the front wall 607a and rear wall 607c extend substantially vertically from the top 603 to the base 605. The side walls 607b, 607d have a generally tapered configuration in which lower portions of the side walls are positioned closer together than upper portions of the side walls. This provides clearance for first engagement feature(s) 609 which is/are configured to engage with complementary second engagement feature(s) 315, 315' of the support apparatus 200, 200' to couple the container with the support apparatus 200, 200' as described in more detail below.

In the form shown, the engagement features 609 are provided on the narrower lower portions of the side walls, which enables the upper portion of the body 601 to be larger, thereby maximising liquid volume in the container. Alternatively, the side walls could be parallel, and positioned closer together over their entire extent, but that would reduce the liquid volume in the container 600.

The body 601 has a fixed shape, whether or not the container is holding liquid. The body of the container has the same shape when the body of the container is full of liquid to a maximum fill level and when the body of the container is empty of liquid. That could be achieved by making the body of a rigid material, such as a rigid polymeric material. Exemplary materials are polypropylene or high density polyethylene (HDPE). In an alternate configuration, the body could comprise a more flexible material that is positioned within and held in shape by a rigid frame.

The container has a liquid outlet 611 for supplying liquid to the humidifier liquid chamber 151. The liquid outlet 611 is configured to be in liquid communication with the humidifier liquid chamber 151. The liquid outlet 611 is located at the base 605 of the body 601.

The liquid outlet 611 is non-centrally located in the base of the body 601.

The liquid outlet 611 is located at or adjacent a side of the body 601. In the form shown, the liquid outlet 611 is located at or adjacent the right side wall 607d of the body, but alternatively could be located or adjacent the left side wall 607b of the body.

The liquid outlet 611 is located at or adjacent a rear of the body 601.

The liquid outlet 611 is angled towards the side of the body 601 that the liquid outlet is positioned at or adjacent.

By positioning the liquid outlet at or adjacent the side of the body 601, and optionally at or adjacent the rear of the body 601 and/or optionally angled towards the side of the body 601, a liquid conduit that is in fluid connection with the liquid outlet 611 will not hang directly down from the centre of the container 600, and is less likely to interfere with, or obscure, a display 14, 14' of a breathing assistance apparatus 10, 10' when the liquid container 600 and the breathing assistance apparatus 10, 10' are coupled to the support apparatus 200, 200'. The position of the liquid outlet also allows any liquid dripping from the outlet to avoid falling on a centre of the breathing assistance apparatus 10, 10'. The centre of the breathing assistance apparatus 10, 10' may comprise sensitive electronic portions of the breathing assistance apparatus. The liquid conduit will advantageously be located behind the first engagement feature(s) 609.

Figure 58:
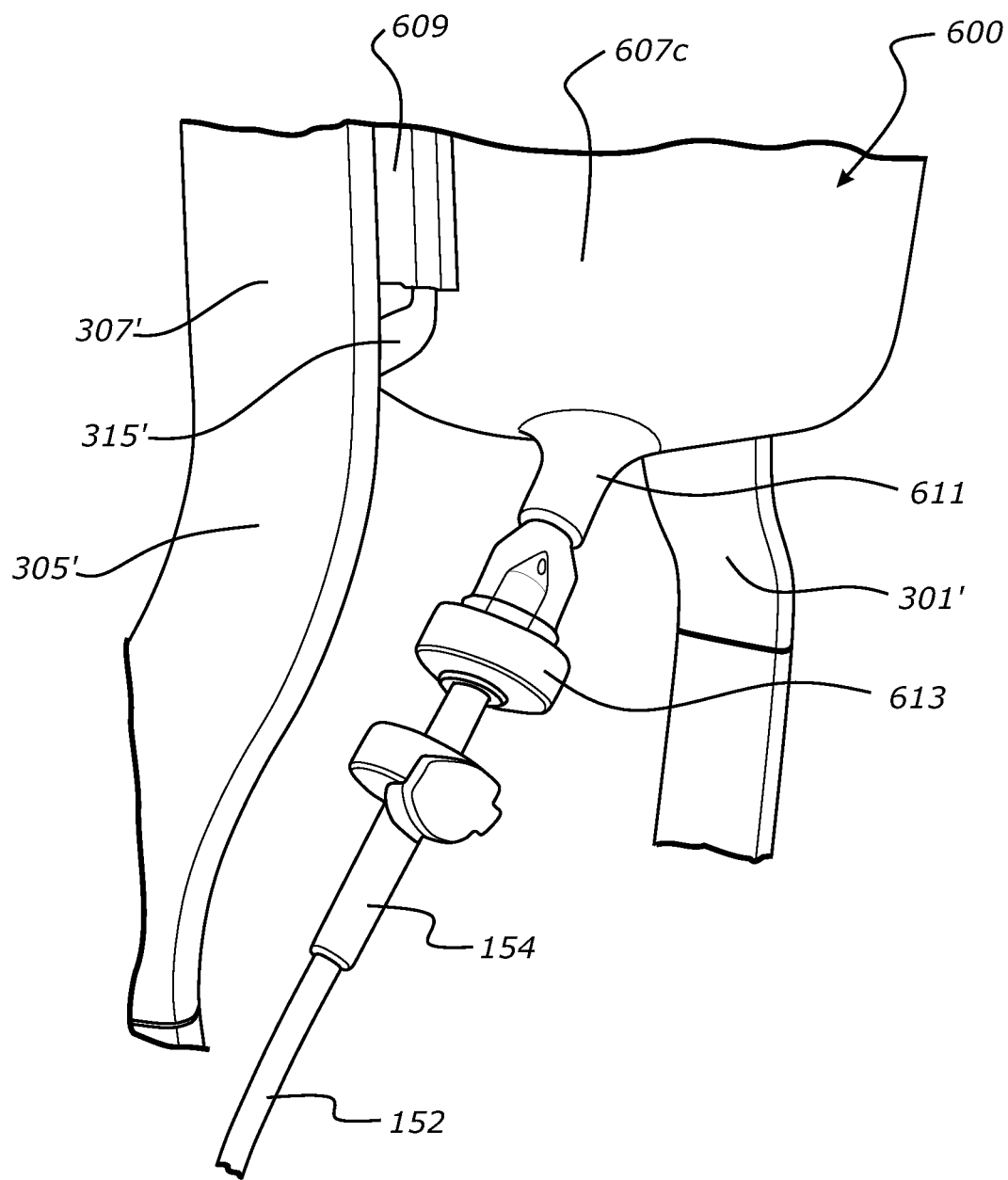
FIG. 58 is a partial right side/rear overhead perspective view showing a spike connector of a liquid conduit connected to the liquid conduit adapter.

The liquid outlet 611 comprises, or is configured to connect to, a liquid conduit adapter 613. The liquid conduit adapter is configured to connect to a liquid conduit 152 of the humidifier liquid chamber 151. The liquid conduit 152 may have a spike connector 154, and the liquid conduit adapter 613 is configured to connect to the spike connector (FIG. 58).

The liquid conduit adapter 613 may form an interference fit with the liquid outlet 611 to prevent any liquid from leaking out between the liquid outlet and the liquid conduit adapter. Additionally, or alternatively, the liquid conduit adapter 613 could be connected to the liquid outlet using an adhesive, to prevent the liquid conduit adapter from coming loose, as well as to prevent any liquid from leaking out. Additionally, or alternatively, a metal clip can be placed over region 614 (FIG. 56) of the portion of the liquid outlet 611 that receives the liquid conduit adapter 613.

The liquid conduit adapter 613 is configured to seal the liquid outlet 611 of the container 600 when not in use, while allowing liquid to be supplied to a liquid conduit for an auto-refilling liquid chamber 151 when in use.

Alternatively, the liquid conduit adapter may be configured to connect to a different type of liquid conduit connector.

A portion 605a of the base 605 of the body is sloped so as to be non-horizontal and non-vertical when the container is coupled to the support apparatus 200, 200'. That is, the sloped portion 605a is oriented at an angle above horizontal and less than vertical when the container 600 is in use. For example, the sloped portion may be oriented at an angle of between about 10-80 degrees above horizontal when the container 600 is in use. Exemplary angles are about 10-70 degrees, about 10-60 degrees, about 10-50 degrees, about 10-40 degrees, about 10-30 degrees, or about 10-20 degrees, about 20-80 degrees, about 20-70 degrees, about 20-60 degrees, about 20-50 degrees, about 20-40 degrees, about 20-30 degrees, about 30-80 degrees, about 30-70 degrees, about 30-60 degrees, about 30-50 degrees, about 30-40 degrees, about 40-80 degrees, about 40-70 degrees, about 40-60 degrees, about 40-50 degrees, about 50-80 degrees, about 50-70 degrees, about 50-60 degrees, about 60-80 degrees, about 60-70 degrees, or about 70-80 degrees above horizontal when the container 600 is in use. In the form shown, the sloped portion 605a is substantially planar and comprises a front portion of the base of the body. In the form shown, the sloped portion 605a extends over approximately a front half of the base 605 of the body 601. The sloped portion 605a could alternatively have a different configuration, such as arcuate, and could be a larger or smaller portion of the base 605.

The liquid outlet 611 is located at or adjacent a bottom of the sloped portion 605a. In the form shown, the remainder of the base 605 comprises a floor portion 605b that extends rearwardly from the bottom of the sloped portion 605a to the rear wall 607c. The floor portion has a flatter angle than the sloped portion 605a, and may be horizontal for example. The liquid outlet 611 is located at the floor portion of the base.

The sloped portion 605a helps funnel the liquid into the area 605b of the base 605 where the liquid outlet 611 is located, to allow a greater proportion of the liquid in the container to be fed to the liquid outlet 611, liquid conduit adapter 613, and liquid conduit before a container refill is required.

In an alternative configuration, the base 605 of the housing can be configured with the location of the liquid outlet 611 being the single lowest point on the base 605.

Figure 51:
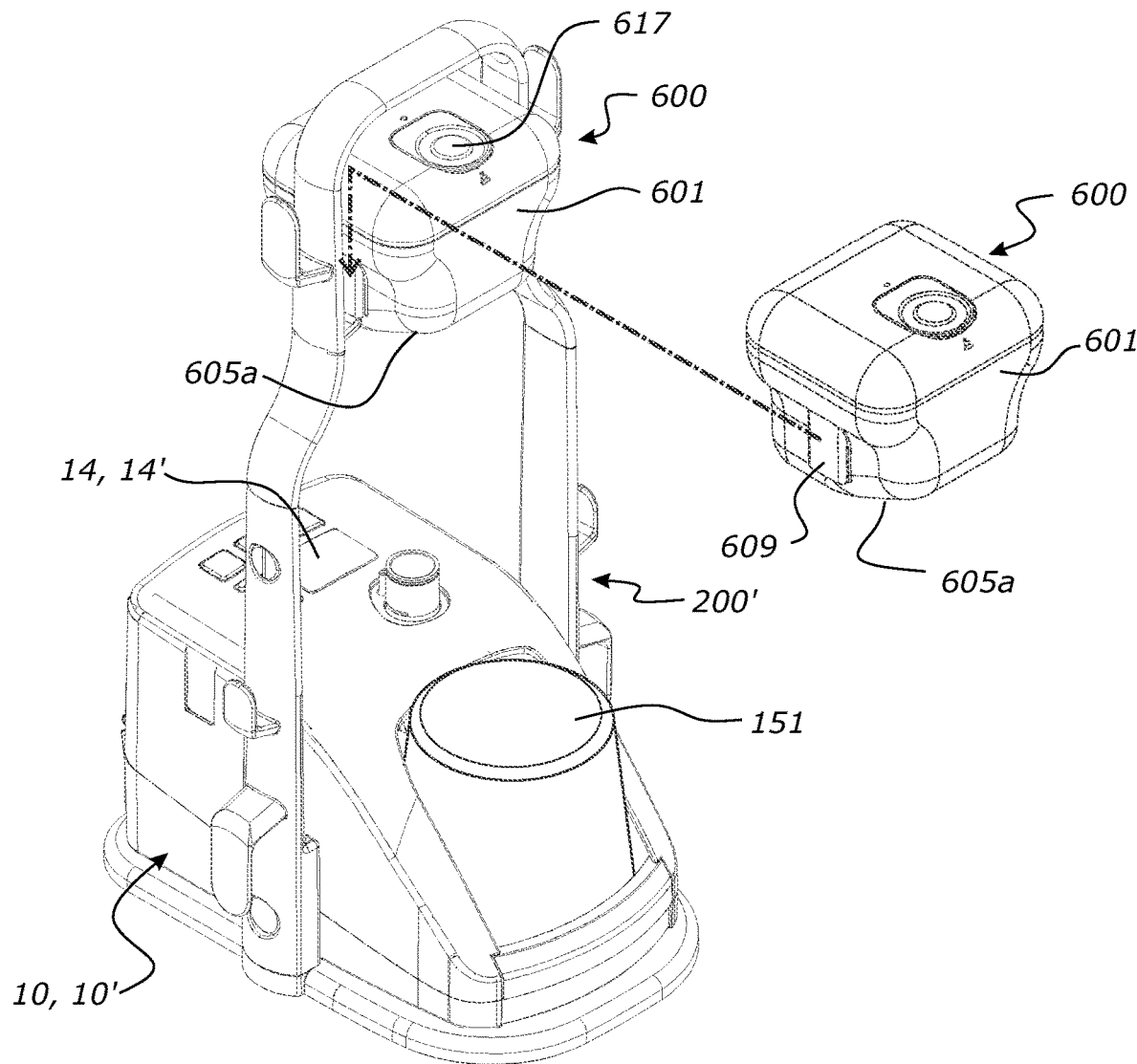
FIG. 51 is a front overhead perspective view showing installation directions of the liquid container onto the support apparatus.
Figure 52:
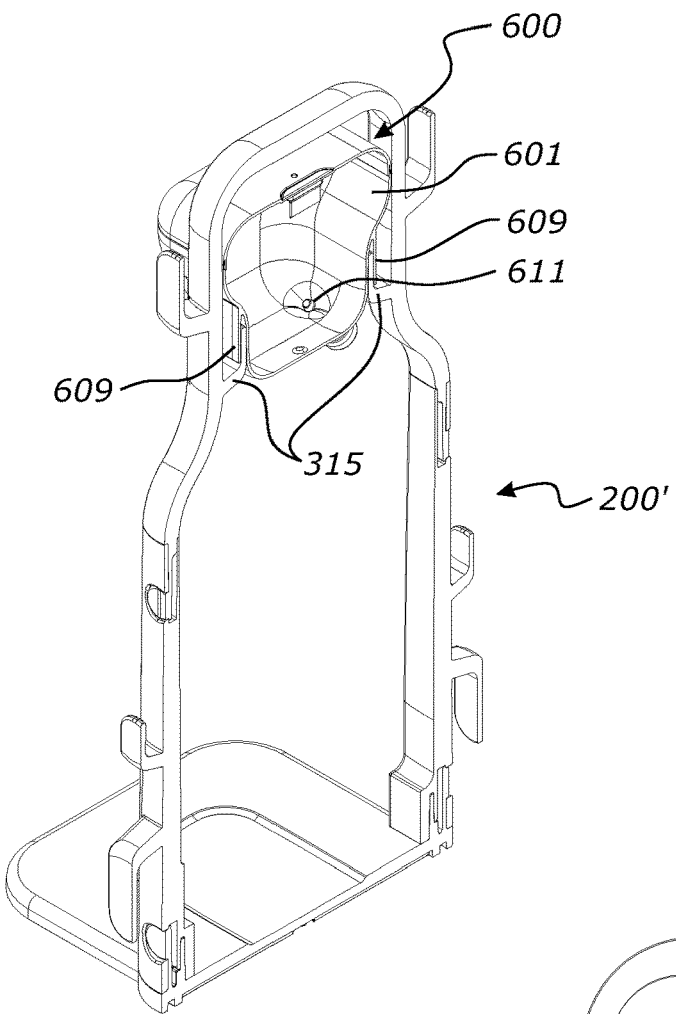
FIG. 52 is a sectional view showing the engagement features of the liquid container and the support apparatus.

When the breathing assistance apparatus 10, 10' having a display 14, 14' is coupled with the support apparatus and the container 600 is coupled with the support apparatus as shown in FIG. 51, a spacing is provided between the base 605 of the body and the display 14, 14' of the breathing assistance apparatus 10, 10'. The sloped portion 605a of the base is configured to minimise or avoid obstruction of the display 14, 14' by the container 600. Therefore, a user's view of the screen is unlikely to be obstructed by the base of the container, particularly when viewed from a high front-facing angle.

Figure 55:
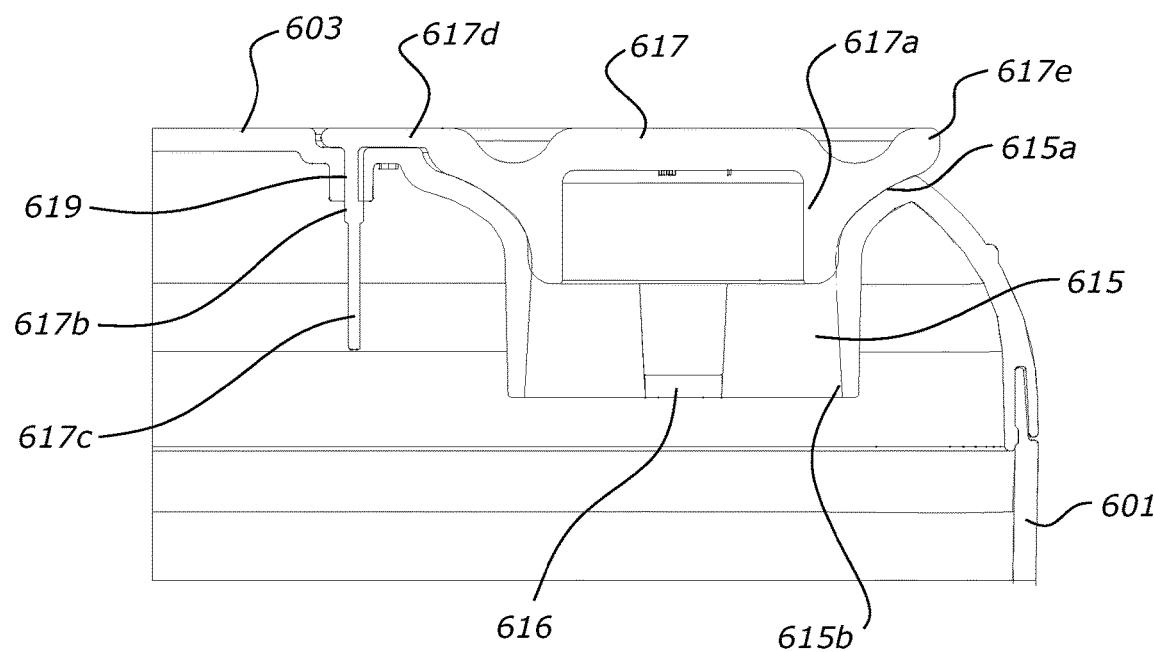
FIG. 55 is a left side sectional view showing the shape of the refilling aperture of the liquid container and showing the engagement of the lid with the refilling aperture.
Figure 56:
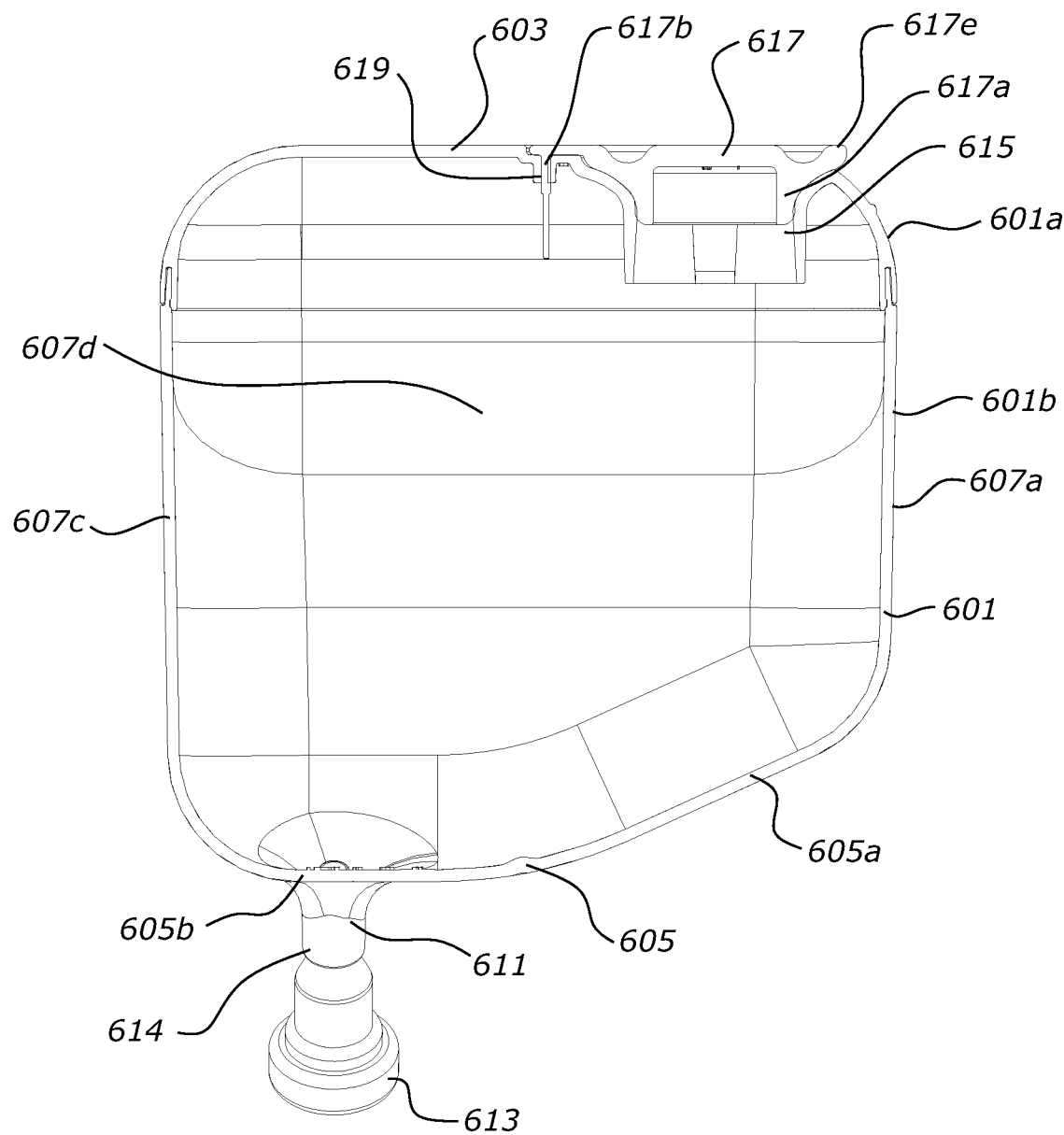
FIG. 56 is a left side sectional view showing the shape of the interior of the liquid container.

As shown in FIGS. 55 and 56, the container 600 comprises a liquid refilling aperture 615 to enable filling of the container body 601 with liquid. The liquid refilling aperture 615 is separate from the liquid outlet 611.

In the form shown, the liquid refilling aperture 615 is located in the top 603 of the body. In an alternative configuration, the liquid refiling aperture could be located in an upper portion of one of the walls of the peripheral wall portion 607.

The liquid refilling aperture 615 has a tapered shape in which an entrance 615a of the liquid refilling aperture has a larger dimension than an exit 615b of the liquid refilling aperture. That is, the liquid refilling aperture has a generally funnel-shaped configuration to aid with pouring liquid into the body 601.

The upper entrance 615a of the liquid refilling aperture 615 is the widest, providing a larger area for liquid to be poured into. The lower exit 615b is narrower, allowing for tight engagement with the bung portion 617a of the cover or lid 617 without requiring an excessively wide bung portion 617a.

The body 601 may be provided with an indicator to indicate a maximum refilling liquid volume of the body 601. In the form shown in FIG. 49, the indicator comprises a maximum fill tab 616 that extends across the lower exit 615b of the liquid refilling aperture 615. The maximum fill tab 616 is visible from above the liquid refilling aperture 615, and provides a visual indicator for a user to stop refilling the body 601 when the liquid in the body reaches the maximum fill tab 616.

The maximum fill tab 616 may be horizontal as shown. Alternatively, the maximum fill tab 616 could be sloped so as to be at a non-horizontal angle.

The maximum fill level could then be indicated by a maximum fill indicator on the maximum fill tab 616. This maximum fill indicator could be located at the top of the sloped maximum fill tab.

When refilling the container 600, the user may only be able to view the liquid from directly above the liquid refilling aperture 615, if the container 600 is sufficiently opaque. This can make it difficult to discern the exact level of the liquid in the container 600.

The body 601 of the container 600 can be made transparent or translucent, which may also allow the user to judge the liquid level while refilling the container 600. This approach could be an alternative to using a maximum fill tab 616.

The user may refill the container 600 while looking down on the container, and in this scenario may be unable to easily judge the liquid level by looking at the side of the container 600. As such, it could be beneficial to use a maximum fill tab 616 as well as a transparent or translucent material for the body 601 of the container 600.

Having a sloped maximum fill tab 616 would mean that the user could use the lateral position of the liquid against the maximum fill tab to determine how close the volume of liquid is to the maximum fill level. This could reduce the chance of the user overfilling the container 600.

The container 600 may have a minimum fill indicator (not shown) to indicate to a user that the container will need refilling. In some configurations, the minimum full indicator is a line or other marker on the body 601 of the container. This configuration may be suitable when the container body is transparent or translucent.

In some configurations, the minimum fill indicator is provided by a minimum fill tab in the body 601 of the container 600. This may be in addition to the maximum fill tab 616. Alternatively, the container may have a minimum fill tab but no maximum fill tab 616. The minimum fill tab may be used with an opaque, translucent, or transparent body 601.

Alternatively, the indicator may extend inwardly from a wall of the peripheral wall portion 607 of the body 601, so as to be positioned beneath the liquid refilling aperture 615.

The indicator may be provided with a visual prompt, such as suitable lettering, to remind a user that the maximum fill tab 616 represents the maximum liquid volume in the body 601.

The container 600 comprises a cover or lid 617 to engage with the liquid refilling aperture 615. The lid 617 may seal the liquid refiling aperture 615 or may simply substantially cover the liquid refilling aperture 615.

In the form shown, the lid 617 comprises a bung portion 617a that engages with the liquid refilling aperture 615, a connector portion comprising a larger dimension upper portion 617b and a smaller dimension lower portion 617c, and a resilient joiner portion 617d that joins the bung portion 617a to the connector portion.

The lid 617 is connected to or connectable to the body 601. That can be achieved by inserting the connector portion into a slot 619 in the body 601. The connector portion 617b, 617c acts as a vertical retention feature to retain the lid 617 in engagement with the body.

The smaller dimension lower portion 617c acts as a guiding portion to assist with inserting the connector portion into the slot 619. The larger dimension upper portion 617b may be a press fit in the slot 619 and/or may be adhered to the slot, to minimise the likelihood of removal from the slot 619. Additionally, or alternatively, the connector portion can be configured with a projection or flange that engages with an underside of the slot 619.

The lid 617 may be removably connected to the body 601.

The connector portion 617b, 617c may be formed as a flat tab, and the slot 619 may be formed as a complementary slot that extends transversely across and downwardly into the body 601. Other configurations could be provided. The connector portion and the slot may be configured to provide audible and/or haptic feedback to a user so they know that the connector portion has properly engaged in the slot.

The connector portion 617b, 617c acts to help align the bung portion 617a with the liquid refiling aperture 615.

The lid 617, and more specifically the bung portion 617a, is biased into engagement with the liquid refilling aperture. The lid 617 is connected to or connectable to the body 601 to be biased into engagement with the liquid refilling aperture.

At least the joiner portion 617d is resilient so as to flex when a user removes the bung portion 617a from the liquid refilling aperture 615 to expose the liquid refilling aperture 615 for filling. At least the joiner portion 617d provides the biasing force to return the bung portion 617a back into engagement with the liquid refilling aperture when the user removes force from the bung portion 617a. In some configurations, the entire lid 617 may be made of a resilient material.

The lid may be made from any suitable resilient material, such as an elastomeric material for example. Exemplary materials include silicone, a thermoplastic elastomer, or cork, for example.

In addition to, or as an alternative to, the biasing of the lid 617 into engagement with the liquid refilling aperture 615, the bung portion 617a may be an interference fit with the liquid refilling aperture 615.

By keeping the lid 617 connected to the body 601 while exposing the liquid refiling aperture 615, the likelihood of losing the lid 617 while refilling the container 600 is reduced.

As shown in FIG. 55, a protruding rim 617e of the lid 617 may be exposed from the body 601 of the container when the lid 617 is engaged with the liquid refiling aperture 615 to enable the user to easily grasp and move the lid.

A visual and/or tactile indicator 622 is located on the container 600 in front of the lid 617. The indicator 622 directs a user towards the portion of the seal (e.g. projecting rim portion 617e) that indicates where a user should attempt to lift the lid when attempting to refill the container 600. The indicator 622 directs the user toward the protruding rim 617e of the lid 617, which can be gripped to lift the lid 617. The indicator can be shaped as an arrow or similar shape that points towards that location. The indicator may comprise a protrusion or indentation, so that a user can locate the indicator by touch.

The lid 617 is lifted from the side opposite the connector portion, to enable the lid to flex backwards through the resilient joiner portion 617d to expose the refilling aperture 615 without detaching the lid 617 from the container body 600.

Figure 43:
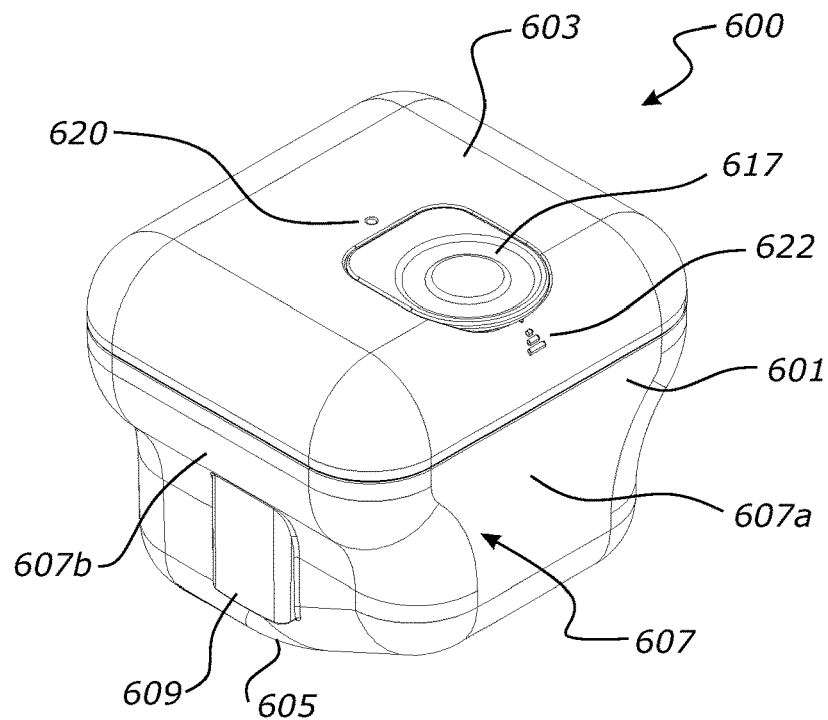
FIG. 43 is a left side/front overhead perspective view of the liquid container.
Figure 44:
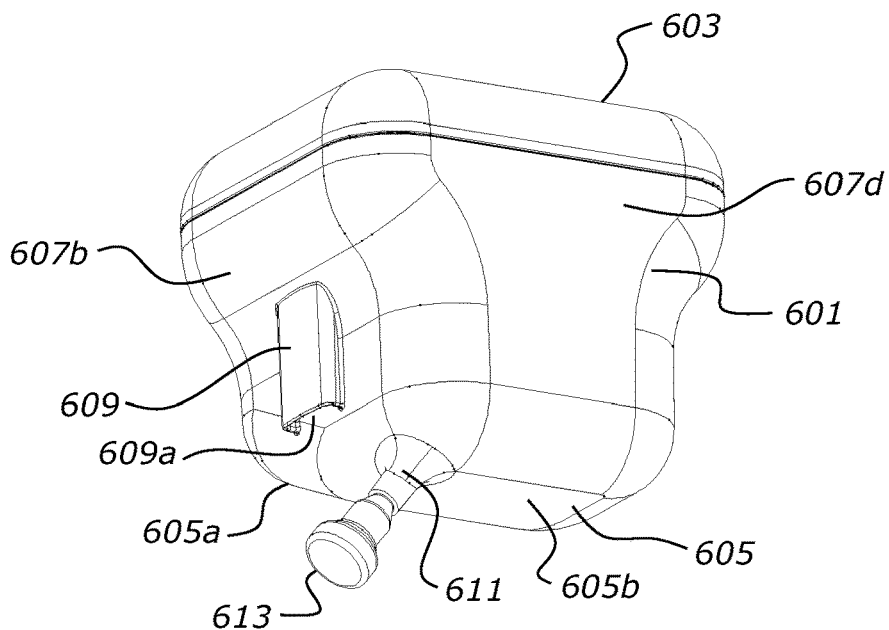
FIG. 44 is a right side/rear bottom perspective view of the liquid container.
Figure 45:
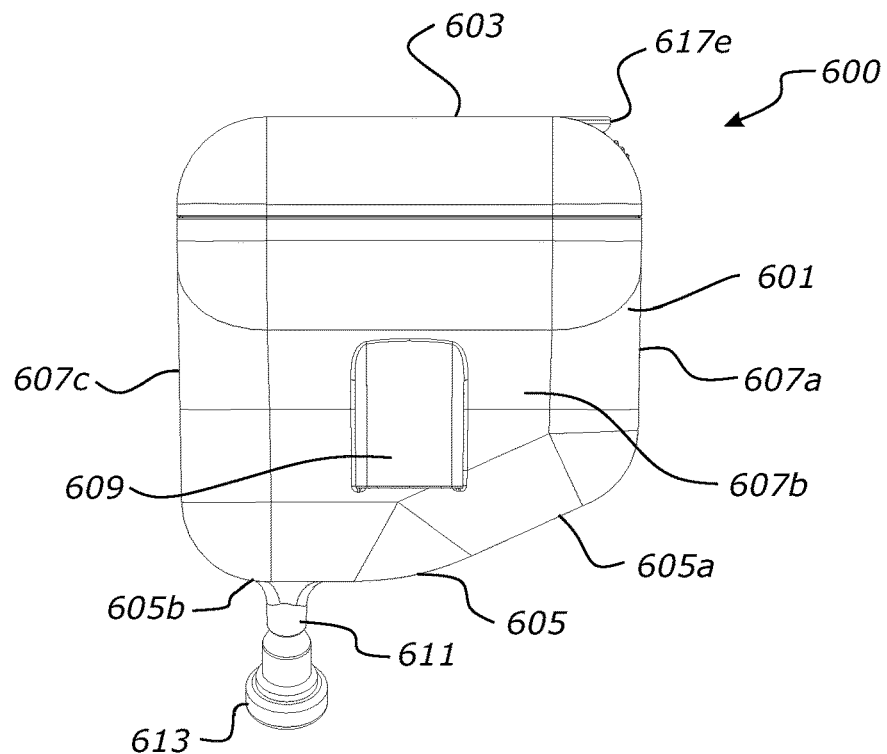
FIG. 45 is a left side view of the liquid container.
Figure 46:
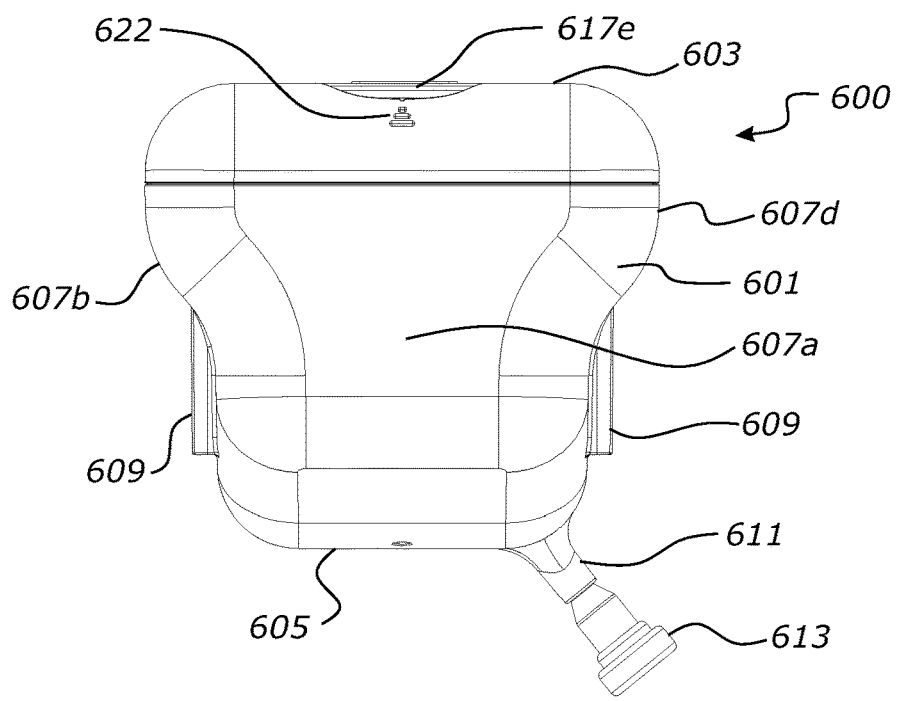
FIG. 46 is a front view of the liquid container.
Figure 47:
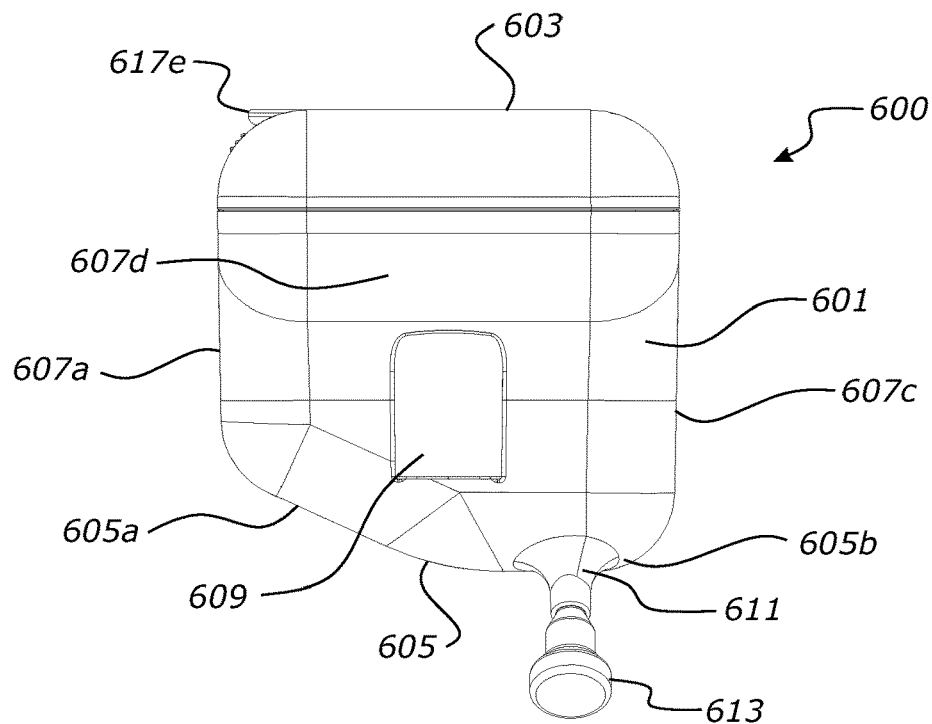
FIG. 47 is a right side view of the liquid container.
Figure 48:
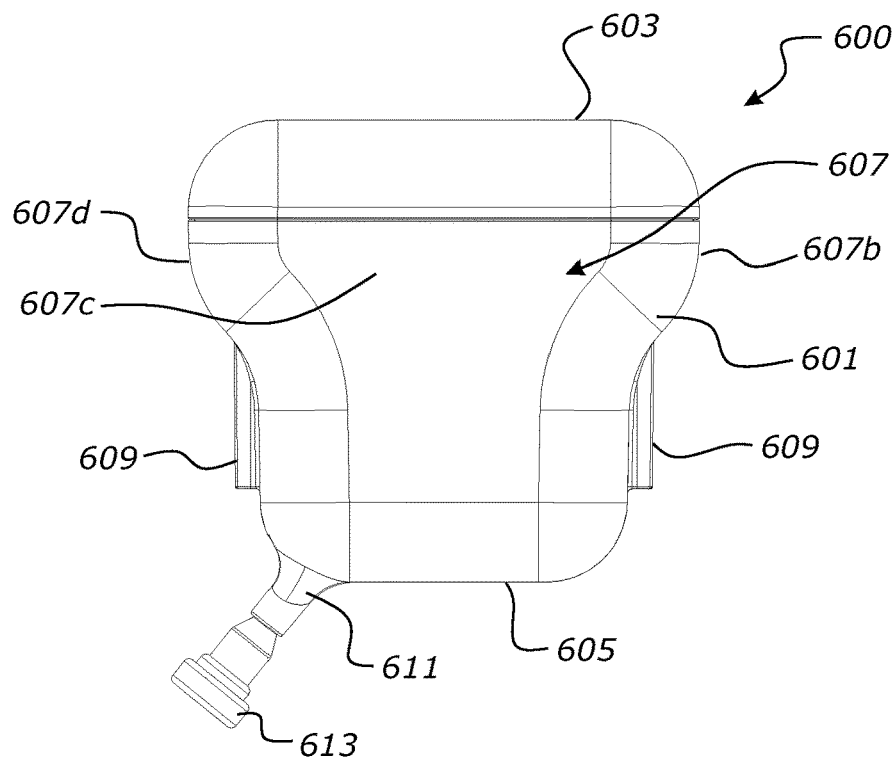
FIG. 48 is a rear view of the liquid container.
Figure 49:
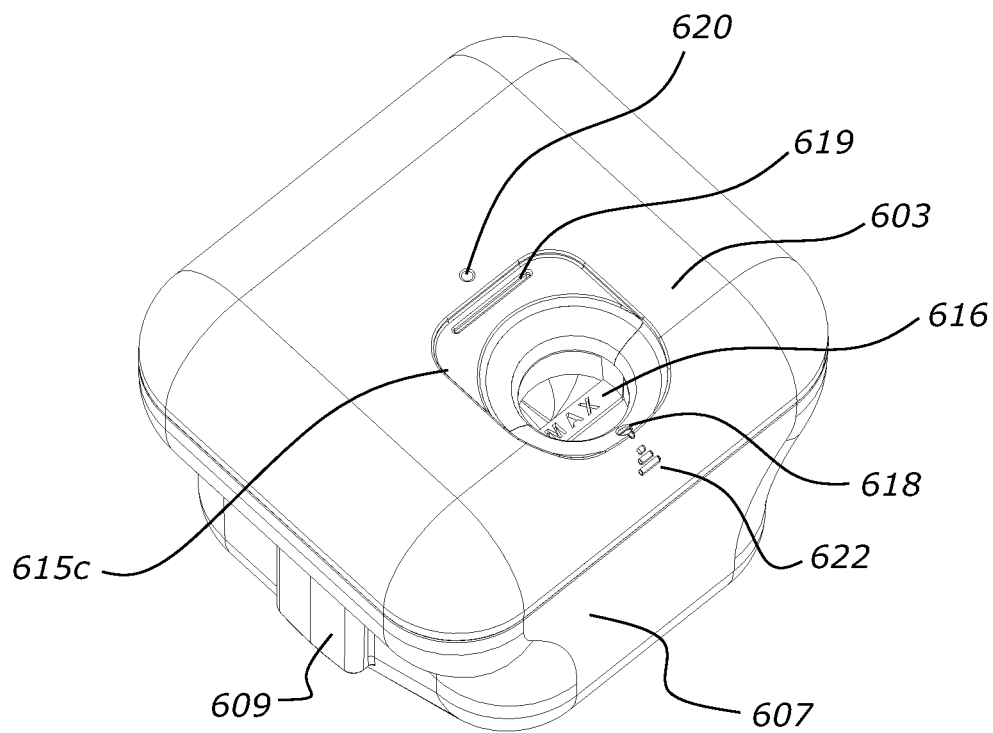
FIG. 49 is a left side/front overhead perspective view of the liquid container, with the lid not shown.
Figure 50:
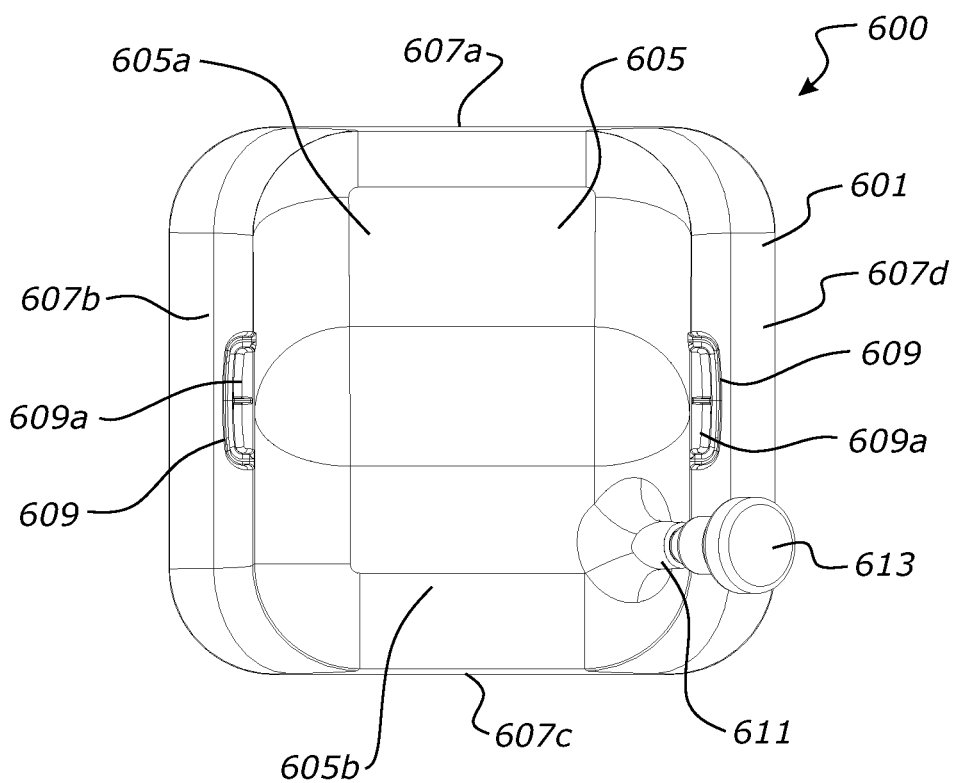
FIG. 50 is a bottom view of the liquid container.

With reference to FIGS. 43 and 49, the container is provided with a venting aperture 620 that is configured to allow ambient air to enter the container while liquid is exiting the container through the liquid outlet 611. This is advantageous when the body has a fixed shape, so cannot compress as liquid exits the liquid outlet 611. The venting aperture 620 assists with avoiding a vacuum in the container. Without a venting aperture, a full pneumatic seal could form when the lid 617 is engaged with the liquid refiling aperture 615. When liquid is exiting the container, a full pneumatic seal would cause negative pressure to be generated inside the body 601, which could in turn prevent further liquid from flowing out of the container.

The venting aperture 620 is located above any liquid volume in the container so as to remain unblocked when the body 601 contains a full volume of liquid.

The lid may substantially seal the liquid refilling aperture 615 when the lid 617 is engaged with the liquid refilling aperture. In that configuration, the venting aperture 620 may be an auxiliary aperture in the body 601. In the form shown, the venting aperture is shown in the top 603 of the body 601. Alternatively, the venting aperture may be located in an upper portion of one of the walls of the peripheral wall portion 607.

In an alternative configuration, the auxiliary venting aperture is provided in the lid 617, for example in the bung portion 617a.

In an alternative configuration, the lid 617 and the liquid refilling aperture 615 are configured such that the venting aperture is provided by a space between the lid 617 and the liquid refilling aperture 615 when the lid is engaged with the liquid refilling aperture. For example, the space may be between the bung portion 617a and the liquid refilling aperture 615.

The body 601 may comprise a drainage aperture 618 (FIG. 49) adjacent to the liquid refilling aperture 615. The drainage aperture 618 may be provided adjacent the front of the liquid refiling aperture 615 in a liquid refilling aperture recess 615c in the top 603 of the body. Alternatively, the drainage aperture 618 may be provided elsewhere in the recess 615c.

The purpose of the drainage aperture 618 is to allow a user to be able to empty substantially all of the liquid in the container 600. Without a drainage aperture 618, some liquid may become trapped around the liquid refilling aperture 615, preventing a user from fully draining the liquid container. The drainage aperture can also be partially blocked by the lid 617.

The drainage aperture 618 may also prevent a full pneumatic seal from forming when the lid 617 engages with the refilling aperture 615. Therefore, the drainage aperture can act as the venting aperture, and may be provided as an alternative to the venting aperture 620.

In an alternative configuration, the separate venting aperture 620 could be provided in addition to the drainage aperture 618. In this configuration, the drainage aperture 618 could be fully blocked by the lid 617 when the lid is engaged with the liquid refilling aperture 615.

Part of the lid 617 may be located in the liquid refilling aperture recess 615c, at least when the lid is engaged with the liquid refilling aperture. That enables the upper surface of the majority of the lid 617 to be substantially flush with the top 603 of the body 601.

The container 600 is configured to couple to the support apparatus 200 or 200', as shown in FIGS. 41, 42, 51, 52, and 53.

The container 600 has at least one first engagement feature 609 which is/are configured to engage with at least one complementary second engagement feature 315, 315' of the support apparatus 200, 200' to couple the container with the support apparatus 200, 200'. The container 600 and the support apparatus 200, 200' may have a plurality of engagement features. In the form shown, the container 600 and the support apparatus 200, 200' each have two engagement features. Alternatively, the container 600 and the support apparatus 200, 200' may have three or more engagement features.

The first engagement features 609 are located at or adjacent opposite sides 607b, 607d of the body 600.

The second engagement features 315, 315' are located on inner surfaces of the upper upstanding members 303', 307', and are located below the upper transverse connecting member 309, 309' that extends between and connects upper ends of the two upstanding members 303', 307'.

It will be understood that a single engagement feature could be provided on each of the container 600 and the support apparatus 200, 200'. For example, the support apparatus 200, 200' could have a single upstanding member with a second engagement feature 315, 315', rather than two spaced-apart upstanding members with respective engagement features.

In one configuration, the first engagement feature 609 comprises a slot or recess 609a to engage with a support portion 315b, 315b' of the second engagement feature 315, 315' that extends in a first, upward direction. Alternatively, the first engagement feature 609 of the container 600 comprises a support portion that extends in a second, downward direction (similar to the support portion 313b, 313b' of the second mechanical feature on the support apparatus 313, 313') to engage with a slot or recess of the second engagement feature on the support apparatus.

Figure 53:
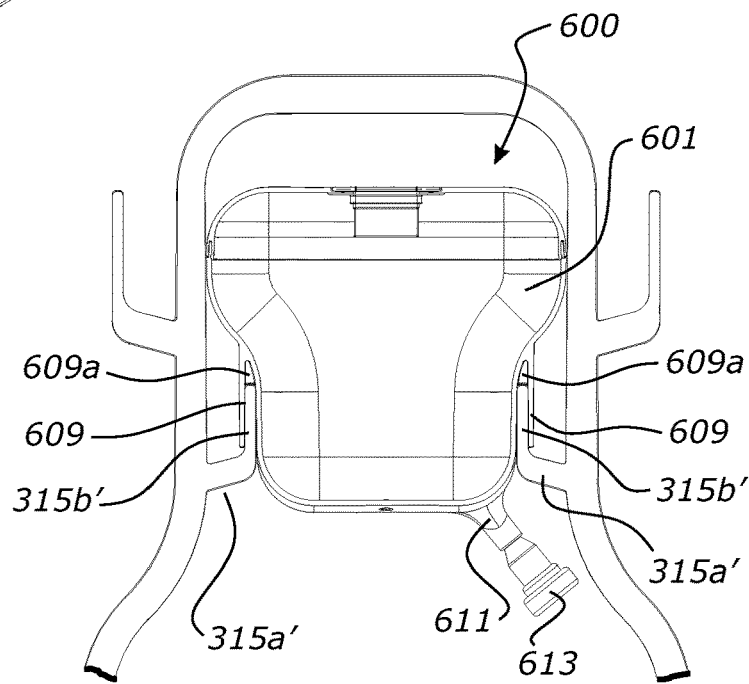
FIG. 53 is another sectional view showing the engagement features of the liquid container and the support apparatus.
Figure 54:
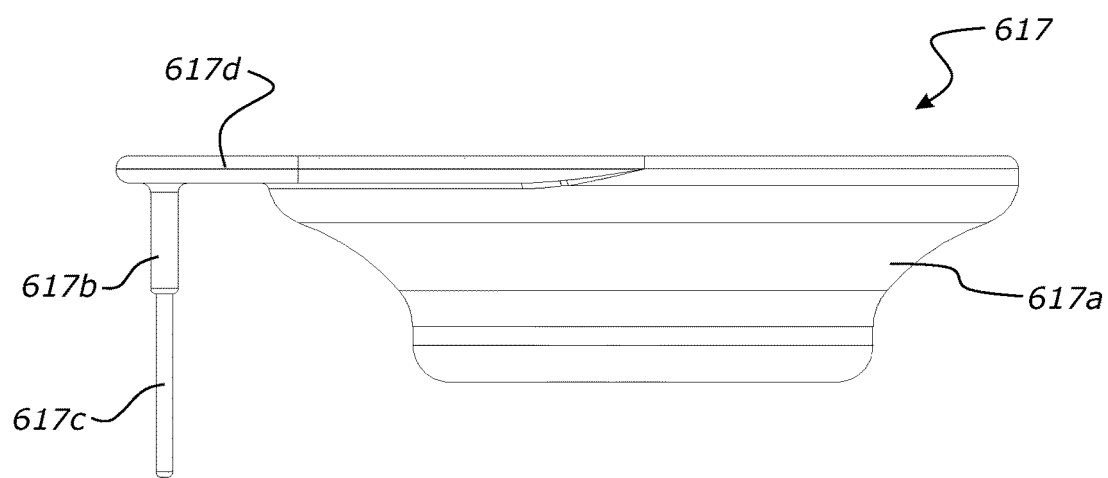
FIG. 54 is a left side view of the lid of the refilling aperture of the liquid container.

In the form shown, the first engagement feature 609 comprises a slot or recess 609a. As shown in FIG. 53, an upper portion of the slot or recess 609a is tapered with a reducing size, to define a maximum insertion depth of the support portion 315b, 315b' in the slot or recess 609a, while helping to prevent locking of the components together.

The upper transverse connecting member 309, 309' of the support apparatus 200, 200' forms a handle. The handle enables the support apparatus 200, 200', breathing assistance apparatus 10, 10', and container 600 to be lifted and carried.

The engagement features 609, 315, 315' are configured so that a space is provided between the upper transverse connecting member 309, 309' and the container 600 when the container is coupled to the support apparatus.

The container 600 is configured to couple with the support apparatus 200, 200' by moving the container 600 downwardly relative to the support apparatus 200, 200'.

As shown in FIG. 51, the container 600 is configured to initially be moved horizontally (either rearwardly if inserted from the front of the support apparatus or forwardly if inserted from the rear of the support apparatus) relative to the support apparatus 200, 200' until the first engagement feature(s) 609 is/are located directly above the second engagement feature(s) 315, 315', and then moved downwardly so that the first engagement feature(s) 609 engage with the second engagement feature(s) 315, 315' to couple the container with the support apparatus.

The container 600 can be removed from the support apparatus 200, 200' by reversing that movement.

When the container has two first engagement features 609 to engage with two complementary second engagement features 315, 315', different combinations of engagement features can be used. For example, either: the first engagement features 609 comprise slots or recesses to engage with respective support portions 315b, 315b' of the second engagement features 315 that extend in an upward direction from respective portions of the support apparatus; the first engagement features 609 comprise support portions that extend in a downward direction (similar to the support portions 313b, 313b' of the second mechanical features 313, 313' on the support apparatus) to engage with respective slots or recesses of the second engagement features; or one first engagement feature comprises a slot or recess to engage with a support portion of one second engagement feature that extends in an upward direction and another first engagement feature comprises a support portion that extends in a downward direction to engage with a slot or recess of another second engagement feature.

The latter configuration may be advantageous as it only allows the container 600 to be coupled to the support apparatus 200, 200' in a single orientation, which would ensure that the liquid outlet 611 is located adjacent the rear of the support apparatus rather than the front of the support apparatus.

The second engagement feature(s) may be provided by the inner mechanical feature(s) 315, 315' of the support apparatus 200, 200'. Alternatively, the second engagement feature(s) may be provided by different mechanical feature(s) on the support apparatus, which may be provided in addition to, or instead of, the inner mechanical features 315, 315'.

The positioning of the first engagement feature(s) 609 and the second engagement feature(s) 315, 315' is such that the container 600 is coupled to, and supported by, the support apparatus at a location adjacent to, but spaced beneath, the handle 309, 309' of the support apparatus 200, 200'. A user's fingers can fit between the handle 309, 309' and the container, so that the spacing between the handle 309 and the container 600 is such that the container will not interfere with the use of the handle 309.

The positioning of the engagement features enables the container to be suspended above the breathing assistance apparatus 10, 10' and humidifier liquid chamber 151 at a distance that provides adequate pressure for auto-refilling of the humidifier liquid chamber 151 to occur. Additionally, because the shape of the container 600 is fixed, the liquid outlet 611 of the container will remain at a desired height relative to the humidifier liquid chamber 151 irrespective of whether or not there is liquid in the container 600. That differs from a flexible liquid bag that has a higher liquid outlet position when the bag is full and expanded compared to when the bag is nearly empty and collapsed. That means that a liquid bag may not provide adequate pressure to empty the bag, unless it is positioned higher relative to the breathing assistance apparatus and/or humidifier liquid chamber.

Figure 57:
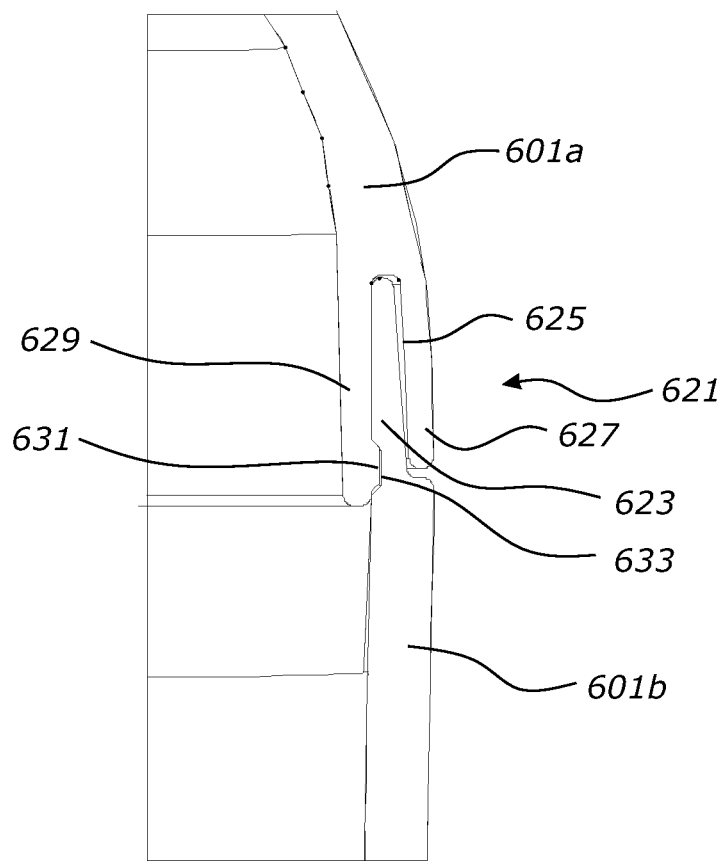
FIG. 57 is a sectional view showing the coupling of upper and lower housings of the liquid container.

As shown in FIGS. 56 and 57, the body 601 of the container 600 may comprise an upper housing 601a and a lower housing 601b that are coupled together.

The first engagement feature(s) 609 will advantageously be located on the lower housing 601b. In use, the weight of liquid in the container 600 creates a downward force that acts through contact points between the support apparatus 200, 200' and the lower housing 601b. If the first engagement feature(s) were on the upper housing 601a, that force would be applied through the connection between the upper and lower housings 601a, 601b. That may lead to a risk of the upper and lower housings becoming disconnected unexpectedly in use. In alternative configurations, the first engagement feature(s) may be provided on the upper housing 601a, and the upper and lower housing are configured to ensure they can't inadvertently separate. The upper and lower housings may comprise positive engagement features or may be fastened together using fasteners to prevent inadvertent separation.

In the form shown, the lower housing 601b forms the major part of the height of the container 600, and the upper housing 601a forms only a minor part of the height of the container.

The rims of the upper and lower housings 601a, 601b comprise a connector arrangement 621 to connect the two housings together. In the form shown, the connector arrangement extends around the peripheral wall portion 607 of the body 601. In other forms, the connector arrangement may extend around a portion of the peripheral wall portion 607 of the body 601.

The connector arrangement 621 may be configured to allow the upper and lower housings to be assembled simply by pushing the two housings together. The connector arrangement may be configured to provide audible and/or haptic feedback to a user so they know that the connector arrangement is fully engaged.

An exemplary connector arrangement is shown in FIG. 57. The lower portion of the connector arrangement 621 comprise an upstanding member 623 on the lower housing 601b that is configured to be received in a downwardly open recess 625 that is located between two downwardly extending members 627, 629 on the upper housing 601a.

One of the inner downwardly extending member 629 and the upstanding member 623 comprises a lateral projection 631 that engages with a complementary lateral recess 633 in the other of the inner downwardly extending member 629 and the upstanding member 623, to maintain the upper and lower housings 601*a*, 601*b* in engagement with each other.

One or more lateral projections 631 may be located on the inner surface of the downwardly open recess 625 to engage with one or more complementary lateral recesses 633 on the outer surface of the upstanding member 623.

Additionally, or alternatively, there can be one or more lateral protrusions located on the outer surface of the upstanding member 623 to engage with one or more complementary lateral recesses on the inner surface of the downwardly open recess 625.

Although the upstanding member 623 is shown as being located on the lower housing 601*b* and the downwardly open recess 625 located on the upper housing 601*a*, the configuration could be reversed with a downwardly extending member located on the upper housing 601*a* and an upwardly open recess located on the lower housing 601*b*.

The connector arrangement 621 may provide a one-time fit between the upper and lower housings 601*a*, 601*b*, so that the upper and lower housings 601*a*, 601*b* cannot be separated after assembly. Alternatively, the connector arrangement can be configured to separate under sufficient force, so that the upper and lower housings 601*a*, 601*b* can be disassembled in certain situations, such as if cleaning is required.

The connector arrangement 601 is advantageously configured to form a tortuous path between the inside and outside of the body 601. This helps prevent any liquid from leaking out of the container.

As shown in FIG. 57, inner surfaces of the recess 625 and the upstanding member 623 may contact each other over substantially their entire heights, to help prevent liquid from leaking out of the container.

Additionally, or alternatively, the container 600 can be configured so that the highest point of the lower housing 601*b* is located higher than a maximum fill volume of the body 600 indicated by the fill tab 616, to help prevent liquid from leaking out of the container.

In addition to, or as an alternative to, the connector arrangement 601, the upper and lower housings can be joined together using an adhesive. The adhesive will prevent the upper housing 601*a* and lower housing 601*b* from being disassembled. The adhesive can help prevent liquid from leaking out of the container.

Figure 59:
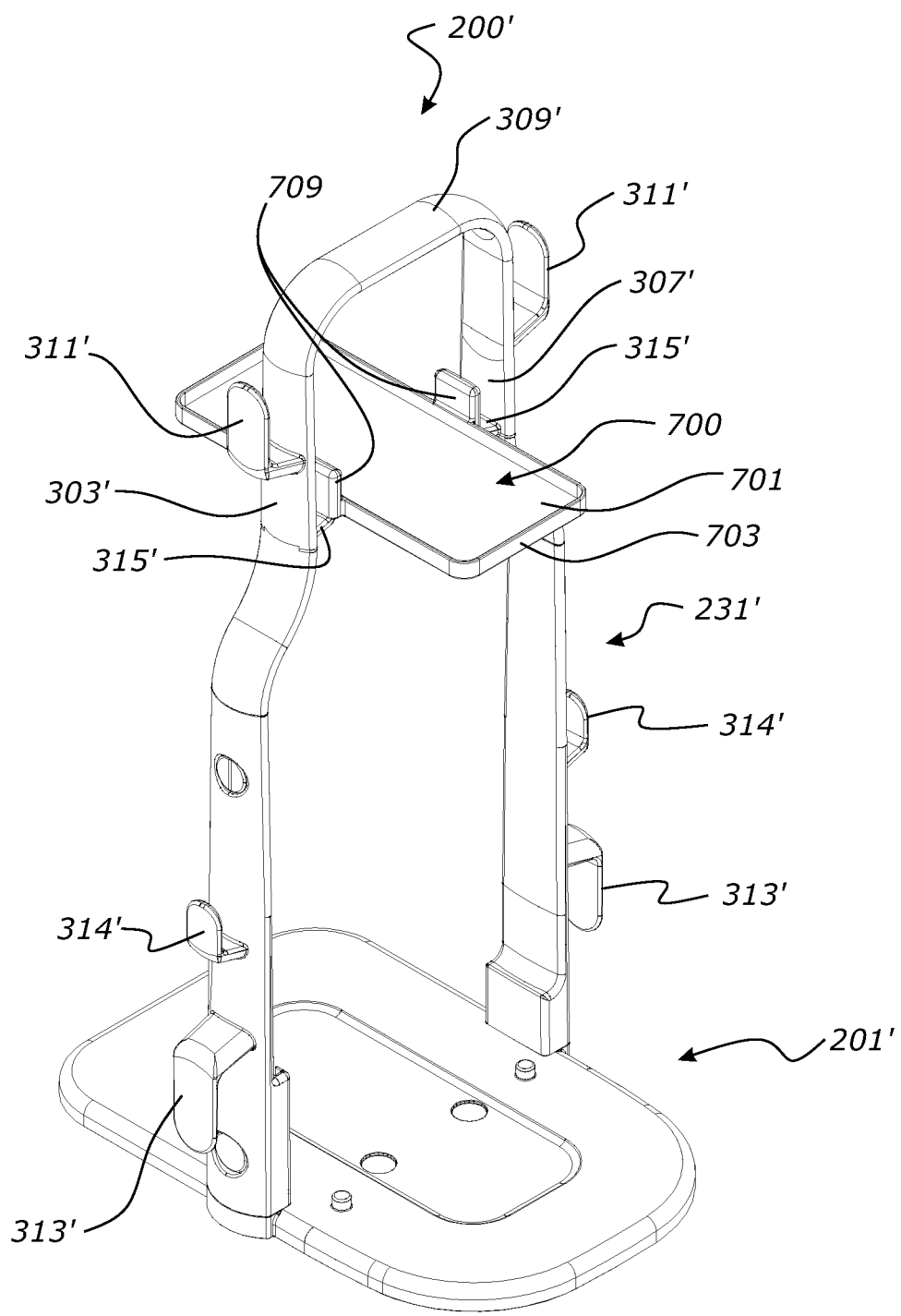
FIG. 59 is a left side/front overhead perspective view showing a tray coupled to a support apparatus.
Figure 60:
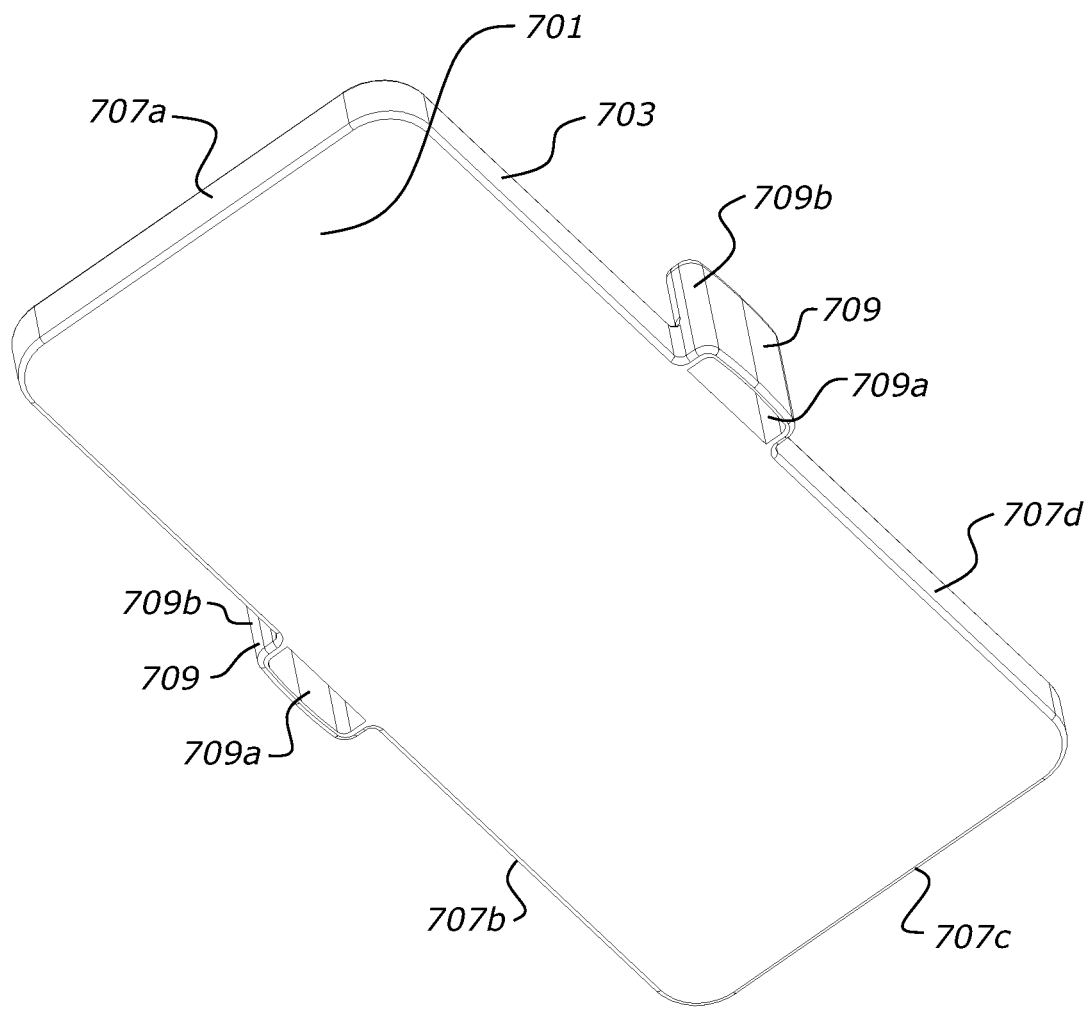
FIG. 60 right side/bottom perspective view of the tray.

FIGS. 59 and 60 show a tray 700 for supporting a liquid container or liquid bag for supplying liquid to the humidifier liquid chamber 151. For example, the liquid bag 101, the liquid container 600, or a different liquid container may be supported on the tray 700. The liquid bag or liquid container is provided for delivering liquid to the humidifier liquid chamber 151. A liquid outlet of the liquid bag or liquid container is configured to be in liquid communication with the humidifier liquid chamber.

The tray 700 has a tray body 701 that provides a support surface for the liquid bag or liquid container. The tray body 701 may have a substantially planar upper surface.

In the form shown, the tray body 701 is horizontally elongate in a forward-rearward direction of the tray body. Any other suitable configuration could be provided, depending on the shape of the support apparatus 200, 200' that the tray will be coupled to.

The tray 700 comprises an upwardly projecting rim 703 extending along at least part of the tray body 701, at or adjacent the periphery of the tray body 701. In the form shown, the upwardly projecting rim extends along substantially the entire front 707*a*, left side 707*b*, back 707*c*, and right side 707*d* of the tray body 701, so as to extend around substantially the entire tray body. In an alternative configuration, one or more projecting rims may extend along part or all of just the front side 707*a* and rear side 707*c* of the tray body 701, with the upstanding members 303, 303', 307, 307' of the support apparatus 200, 200' being positioned adjacent the sides of the tray body 701.

The upwardly projecting rim 703 and/or upstanding members 303, 303', 307, 307' assist with maintaining the liquid bag or liquid container in position on the tray 700 in use.

Additionally, or alternatively, the upper surface of the tray body 701 may be provided with a non-planar surface and/or a surface texture to provide frictional restraint to assist with maintaining the liquid bag or liquid container in position on the tray body 701.

The tray 700 is configured for coupling to a support apparatus 200, 200'. The tray 700 has at least one first engagement feature 709 which is/are configured to engage with at least one complementary second engagement feature 315, 315' of the support apparatus 200, 200' to couple the tray with the support apparatus 200, 200'. The method and detail for coupling the tray 700 to the support apparatus 200, 200' is the same as for coupling the container 600 to the support apparatus 200, 200'.

The tray 700 and the support apparatus 200, 200' may have a plurality of engagement features. In the form shown, the tray 700 and the support apparatus 200, 200' each have two engagement features. Alternatively, the tray 700 and the support apparatus 200, 200' may have three or more engagement features.

The first engagement features 709 are located at or adjacent opposite sides 707*b*, 707*d* of the tray body 700. The first engagement features are provided in upstanding housing members 709*b* that extend from the base of the tray 700 and project upwardly beyond the upper surface of the upwardly projecting rim 703.

The second engagement features 315, 315' are located on inner surfaces of the upper upstanding members 303, 303', 307, 307' of the support apparatus 200, 200', and are located below the upper transverse connecting member 309, 309' that extends between and connects upper ends of the two upstanding members 303, 303', 307, 307'.

It will be understood that a single engagement feature could be provided on each of the tray 700 and the support apparatus 200, 200'. For example, the support apparatus 200, 200' could have a single upstanding member with a second engagement feature 315, 315', rather than two spaced-apart upstanding members with respective engagement features. The upper transverse member may extend from an upper end of the upstanding member.

In one configuration, the first engagement feature 709 comprises a slot or recess 709*a* to engage with a support portion 315*b*, 315*b*' of the second engagement feature 315, 315' that extends in a first, upward direction. Alternatively, the first engagement feature 709' of the tray 700 comprises a support portion that extends in a second, downward direction (similar to the support portion 313*b*, 313*b*' of the second mechanical feature on the support apparatus 313, 313') to engage with a slot or recess of the second engagement feature on the support apparatus.

In the form shown, the first engagement feature 709 comprises a slot or recess 709*a*. As described in relation to slot or recess 609*a* of the container 600, an upper portion of the slot or recess 709*a* may be tapered with a reducing size. This may define a maximum insertion depth of the support portion 315*b*, 315*b*' in the slot or recess 709*a*, while helping to prevent locking of the components together. This may also act as a lead-in for guiding insertion of the support portion 315b, 315b' into the slot or recess 709a.

The upper transverse connecting member 309, 309' of the support apparatus 200, 200' forms a handle. The handle enables the support apparatus 200, 200', breathing assistance apparatus 10, 10', and tray 700 to be lifted and carried.

The engagement features 709, 315, 315' are configured so that a space is provided between the upper transverse connecting member 309, 309' and the tray 700 when the tray is coupled to the support apparatus 200, 200'.

The tray 700 is configured to couple with the support apparatus 200, 200' by moving the tray 700 downwardly relative to the support apparatus 200, 200', as described for container 600 and shown for container 600 in FIG. 51.

The tray 700 is configured to initially be moved horizontally (either rearwardly if inserted from the front of the support apparatus 200, 200' or forwardly if inserted from the rear of the support apparatus) relative to the support apparatus 200, 200' until the first engagement feature(s) 709 is/are located directly above the second engagement feature(s) 315, 315', and then moved downwardly so that the first engagement feature(s) 709 engage with the second engagement feature(s) 315, 315' to couple the tray with the support apparatus.

The tray 700 can be removed from the support apparatus 200, 200' by reversing that movement.

When the tray has two first engagement features 709 to engage with two complementary second engagement features 315, 315', different combinations of engagement features can be used. For example, either: the first engagement features 709 comprise slots or recesses to engage with respective support portions 315b, 315b' of the second engagement features 315 that extend in an upward direction from respective portions of the support apparatus; the first engagement features 609 comprise support portions that extend in a downward direction (similar to the support portions 313b, 313b' of the second mechanical features 313, 313' on the support apparatus) to engage with respective slots or recesses of the second engagement features; or one first engagement feature comprises a slot or recess to engage with a support portion of one second engagement feature that extends in an upward direction and another first engagement feature comprises a support portion that extends in a downward direction to engage with a slot or recess of another second engagement feature.

The second engagement feature(s) may be provided by the inner mechanical feature(s) 315, 315' of the support apparatus 200, 200'. Alternatively, the second engagement feature(s) may be provided by different mechanical feature(s) on the support apparatus, which may be provided in addition to, or instead of, the inner mechanical features 315, 315'.

The positioning of the first engagement feature(s) 709 and the second engagement feature(s) 315, 315' is such that the tray 700 is coupled to, and supported by, the support apparatus at a location adjacent to, but spaced beneath, the handle 309, 309' of the support apparatus 200, 200'. The spacing between the handle 309 and the tray 700 means that the tray and a supported liquid bag or liquid container will not interfere with the use of the handle 309.

The positioning of the engagement features enables the liquid bag or liquid container to be supported by the tray 700 above the breathing assistance apparatus 10, 10' and humidifier liquid chamber 151 at a distance that provides adequate pressure for auto-refilling of the humidifier liquid chamber 151 to occur.

A spacing is provided between the tray 700 and the display 14, 14' of the breathing assistance apparatus 10, 10' when the tray 700 and the breathing assistance apparatus 10, 10' are coupled to the support apparatus, so that the tray does not obscure the display.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Features from any of the described embodiments may be combined with each other and/or an apparatus may comprise one, more, or all of the features of the above described embodiments. Moreover, not all of the features, aspects and advantages are necessarily required to practice the present disclosure. Accordingly, the scope of the present disclosure is intended to be defined only by the claims that follow.

The various configurations described are exemplary configurations only. Any one or more features from any of the configurations may be used in combination with any one or more features from any of the other configurations.

For example, the support apparatus 200 is described as having a holder 231 and a stand 201 that can be releasably coupled together. In an alternative configuration, the holder and stand may be integrally formed.

The holder 231 could be configured to mount directly to a breathing assistance apparatus 10 and extend in an upstanding configuration from the breathing assistance apparatus, and could be provided without a stand 201.

In some configurations, the upstanding arm component that forms the holder 231 may not have mechanical feature(s) 311, 313, 315 for supporting accessories, and/or may not have a handle 309.

The holder 231 is described as extending from one side of the base 203 of the apparatus to the other side of the base 203. The holder 231, could alternatively extend from the front of the base 203 to the rear of the base 203.

In another configuration, the holder 231 may be provided without any mechanical features 311, 313, 315, but provided with the handle 309 to enable the support apparatus 200 and breathing assistance apparatus 10, 10' to be lifted and carried.

Rather than having a first mount 351 and a second mount 371, in some configurations the support apparatus 200 may have just the first mount 351 (and optionally the support member 361), or may have just the second mount 371.

The mounts 351, 371 may be integrally formed with the holder 231 and base 203, or may be formed separately but coupled to the holder 231 and base 203.

As another example, while the first mount 351 is described as engaging with the side of the housing of the breathing assistance apparatus 10, the support apparatus could engage with any suitable part of the housing, such as an upper part, lower part, side part, front part, or rear part.

The support apparatus 200 is described with reference to a breathing assistance apparatus that is capable of delivering heated and humidified gases to a patient or user. The apparatus may be suitable for treating chronic obstructive pulmonary disease (COPD). The apparatus may be configured to deliver gases to a patient interface at a high flow rate (high flow therapy), particularly nasal high flow therapy.

Alternatively, the support apparatus 200 may be used with an apparatus for a different purpose. The apparatus may be a high flow therapy apparatus, or may be a low flow therapy apparatus. For example, the support apparatus 200 may be used with an apparatus for providing continuous positive airway pressure (CPAP), which may deliver gases (humidified or otherwise) at lower flow rates, or may be used with a medical insufflation apparatus.

The support apparatus 200 may alternatively be used with a standalone humidifier that has a housing, a recess 108 for receipt of the liquid chamber 151, and a heater plate 140, but that doesn't have a motor unit. The standalone humidifier may receive gases from an external source.

The support apparatus may alternatively be used with an apparatus that does not require a humidifier and therefore does not require the liquid chamber 151 or chamber bay 108 features. The support apparatus has broad applications in other types of gas delivery apparatuses.

The support apparatus could be configured and used to support any suitable patient interface, such as the patient interfaces described in the Introduction section for example.

Reference to any prior art in this specification is not, and should not be taken as, an acknowledgement or any form of suggestion that the prior art forms part of the common general knowledge in the field of endeavour in any country in the world.

Where reference is used herein to directional terms such as 'up', 'down', 'forward', 'rearward', 'horizontal', 'vertical' etc, those terms refer to when the apparatus is in a typical in-use position and/or with reference to particular orientations shown in the figures, and are used to show and/or describe relative directions or orientations.

The invention claimed is:

1. A support apparatus for supporting an accessory of a breathing assistance apparatus, the support apparatus comprising:
a mount configured to couple with a portion of the breathing assistance apparatus;
a lower upstanding member extending upwardly from the mount, an intermediate connecting portion at an upper end of the lower upstanding member, and an upper upstanding member extending upwardly from the intermediate connecting portion, wherein the upper upstanding member is offset from the lower upstanding member and is substantially parallel to the lower upstanding member; and
a mechanical feature on the upper upstanding member for holding the accessory of the breathing assistance apparatus.

2. A support apparatus for supporting an accessory of a breathing assistance apparatus, the support apparatus comprising:
a mount that is configured to releasably couple the support apparatus with the breathing assistance apparatus;
an upstanding component extending upwardly from the mount, the upstanding component comprising a handle, the handle configured to enable the support apparatus and the breathing assistance apparatus to be lifted and carried by a user when the breathing assistance apparatus is releasably coupled with the support apparatus;
a first mechanical feature on the upstanding component, the first mechanical feature extending in a first direction;
a second mechanical feature on the upstanding component, the second mechanical feature extending in a second direction that is substantially opposite to the first direction; and
an accessory support extension that is configured to couple to the first mechanical feature;
wherein the first and second mechanical features are configured so that the accessory of the breathing assistance apparatus can be wrapped around the first and second mechanical features in a loop.

3. The support apparatus according to claim 2, wherein the first mechanical feature extends upwardly so that the accessory of the breathing assistance apparatus can be hung from the first mechanical feature without using the second mechanical feature.

4. The support apparatus according to claim 2, wherein at least one of the first and second mechanical features comprises a base portion that extends from the upstanding component and a distal support portion that is configured to support the accessory between the distal support portion and the upstanding component, wherein a length of the distal support portion is at least 1.5 times a width of a slot formed between the distal support portion and the upstanding component.

5. The support apparatus according to claim 2, wherein the upstanding component comprises a first lower upstanding member extending upwardly from the mount, a first intermediate connecting portion at an upper end of the first lower upstanding member, and a first upper upstanding member extending upwardly from the first intermediate connecting portion, and wherein the first upper upstanding member is offset from the first lower upstanding member and is substantially parallel to the first lower upstanding member.

6. The support apparatus according to claim 5, wherein the first mechanical feature extends from the first upper upstanding member, and wherein the first mechanical feature has a shape that is complementary to a shape of the accessory.

7. The support apparatus according to claim 6, wherein the first mechanical feature is positioned substantially directly above the first lower upstanding member.

8. The support apparatus according to claim 5, wherein the upstanding component further comprises a second lower upstanding member, a second intermediate connecting portion at an upper end of the second lower upstanding member, and a second upper upstanding member extending upwardly from the second intermediate connecting portion, wherein the second upper upstanding member is offset from the second lower upstanding member and is substantially parallel to the second lower upstanding member.

9. The support apparatus according to claim 2, further comprising a base having ends and a transverse outer dimension, wherein the handle has a length that is shorter than the transverse outer dimension of the base.

10. The support apparatus according to claim 9, wherein the upstanding component further comprises a first upstanding member that comprises a first end at or adjacent to a first side of the base, and a second upstanding member that comprises a second end at or adjacent a second side of the base that is opposite the first side of the base.

11. The support apparatus according to claim 10, wherein the upstanding component further comprises an upper transverse connecting member that extends between and connects upper ends of the first and second upstanding members, wherein the upper transverse connecting member forms the handle.

12. The support apparatus according to claim 10, wherein each of the first and second upstanding members of the upstanding component comprises a lower upstanding member extending upwardly from the base, an intermediate connecting portion at an upper end of the lower upstanding member, and an upper upstanding member extending upwardly from the intermediate connecting portion, wherein the upper upstanding member is offset from the lower upstanding member.

13. The support apparatus according to claim 12, wherein the upper upstanding members of the first and second upstanding members are spaced closer together than the lower upstanding members of the first and second upstanding members.

14. The support apparatus according to claim 12, wherein the lower upstanding members of the first and second upstanding members are removably coupled to the base.

15. The support apparatus according to claim 12, wherein the handle extends between and connects upper ends of the upper upstanding members of the first and second upstanding members.

16. The support apparatus according to claim 9, wherein the base is configured to rest on a support surface, and wherein the handle is substantially parallel to the base.

17. A system comprising the support apparatus according to claim 2 and further comprising the breathing assistance apparatus.

\* \* \* \* \*